US012797299B2

(12) United States Patent
Yamanaka et al.

(10) Patent No.: US 12,797,299 B2
(45) Date of Patent: Nov. 17, 2026

(54) MEDICATION SUPPORT DEVICE

(71) Applicants: Manabu Yamanaka, Kanagawa (JP); Hirotaka Hayashi, Kanagawa (JP); Hiroshi Fujie, Kanagawa (JP); Youhei Niitsuma, Kanagawa (JP); Yu Yamaya, Kanagawa (JP)

(72) Inventors: Manabu Yamanaka, Kanagawa (JP); Hirotaka Hayashi, Kanagawa (JP); Hiroshi Fujie, Kanagawa (JP); Youhei Niitsuma, Kanagawa (JP); Yu Yamaya, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 310 days.

(21) Appl. No.: 18/166,711

(22) Filed: Feb. 9, 2023

(65) Prior Publication Data

US 2023/0293391 A1 Sep. 21, 2023

(30) Foreign Application Priority Data

Mar. 17, 2022 (JP) ................................ 2022-042552
Dec. 16, 2022 (JP) ................................ 2022-201375

(51) Int. Cl.
*A61J 7/00* (2006.01)
*G16H 20/13* (2018.01)

(52) U.S. Cl.
CPC ............ *A61J 7/0084* (2013.01); *G16H 20/13* (2018.01)

(58) Field of Classification Search
CPC ............................... A61J 7/0084; G16H 20/13
See application file for complete search history.

(56) References Cited

U.S. PATENT DOCUMENTS

2006/0011646 A1* 1/2006 Chirnomas ......... G07F 11/1657
221/210
2021/0361532 A1 11/2021 Hayashi et al.

FOREIGN PATENT DOCUMENTS

JP 2017-192455 10/2017
JP 2021-185976 12/2021

* cited by examiner

*Primary Examiner* — Gene O Crawford
*Assistant Examiner* — Ayodeji H Ojofeitimi
(74) *Attorney, Agent, or Firm* — Harness, Dickey & Pierce, P.L.C.

(57) ABSTRACT

A medication support device includes a container that stores a plurality of medicine packs, a pickup device configured to pick up a specific one of the plurality of medicine packs from the container, a conveyor configured to convey the specific one of the plurality of medicine packs picked up by the pickup device, a medicine dispenser configured to arrange the specific one of the plurality of medicine packs conveyed by the conveyor, and a separator configured to make the specific one of the plurality of medicine packs picked up by the pickup device separate from the pickup device. In the medication support device, the plurality of medicine packs are stacked on top of each other in layers in the container, and the pickup device includes a suction device configured to pick up one of the plurality of medicine packs downward from the container.

20 Claims, 29 Drawing Sheets

MEDICATION SUPPORT DEVICE

CROSS-REFERENCE TO RELATED APPLICATIONS

This patent application is based on and claims priority pursuant to 35 U.S.C. § 119(a) to Japanese Patent Application Nos. 2022-042552 and 2022-201375, filed on Mar. 17, 2022, and Dec. 16, 2022, respectively, in the Japan Patent Office, the entire disclosures of which are hereby incorporated by reference herein.

BACKGROUND

Technical Field

Embodiments of the present disclosure relate to a medication support device.

Background Art

For the purposes of arranging a plurality of medicine packages for a plurality of people with reduced space with reduced space, some technologies have been proposed to arrange a plurality of containers or cartridges each of which stores a plurality of medicine packages and place the multiple medicine packages in vertical orientation in a predetermined one of a plurality of partitions of one of the multiple medicine dispensing trays. In other words, in such proposed technologies, the multiple medicine packages are placed such that the thickness direction of those medicine packages are substantially horizontal.

SUMMARY

Embodiments of the present disclosure described herein provide a medication support device includes a container that stores a plurality of medicine packs, a pickup device configured to pick up a specific one of the plurality of medicine packs from the container, a conveyor configured to convey the specific one of the plurality of medicine packs picked up by the pickup device, a medicine dispenser configured to arrange the specific one of the plurality of medicine packs conveyed by the conveyor, and a separator configured to make the specific one of the plurality of medicine packs picked up by the pickup device separate from the pickup device.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

FIG. 12A-1, FIG. 12A-2, FIG. 12A-3, FIG. 12A-4, FIG. 12A-5, FIG. 12A-6, FIG. 12B, and FIG. 12C are schematic diagrams each illustrating an overall operation flow of the medication support device illustrated in FIG. 1, according to an embodiment of the present disclosure.

Figure 1B:
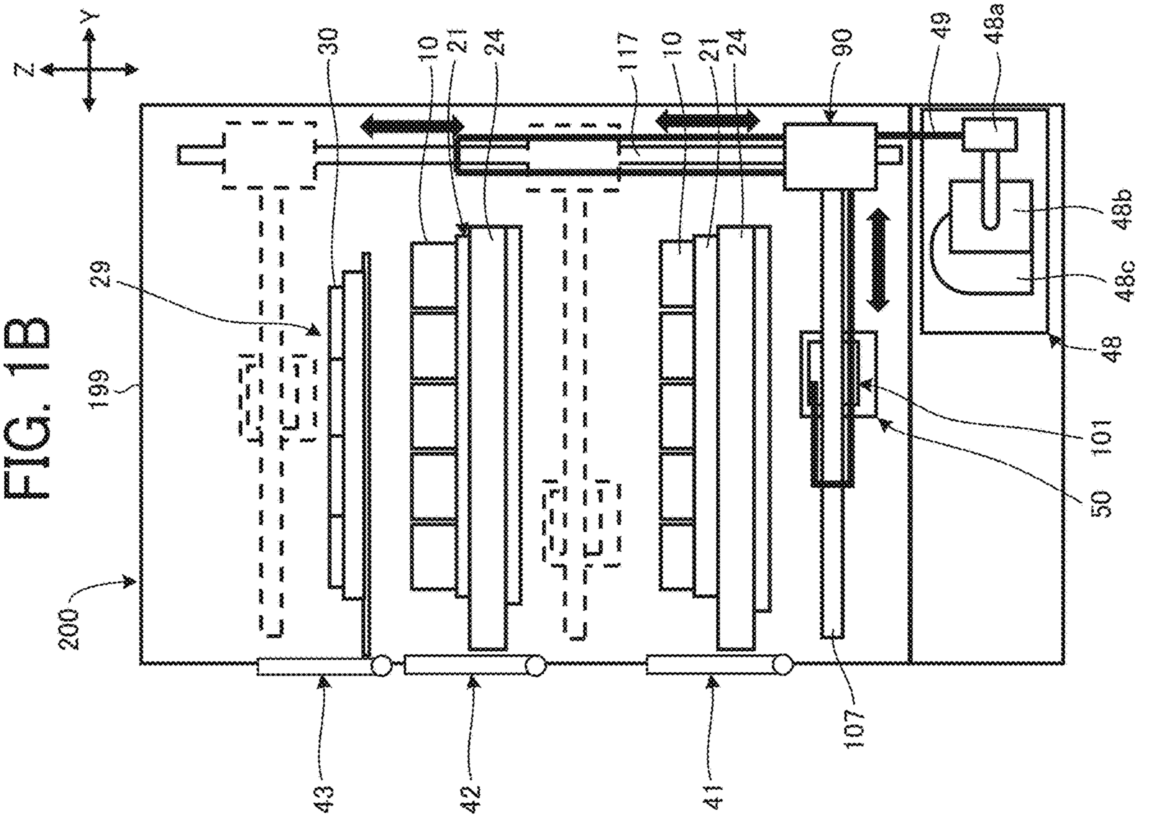
FIG. 1B is a side view the medication support device of FIG. 1A in its entirety, according to an embodiment of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

Embodiments of the present disclosure are described below in detail with reference to the accompanying drawings. In the drawings and the description of the embodiments and examples of the present disclosure, like reference signs denote like elements such as members or components of similar shapes or similar functionality, and overlapping description may be omitted where appropriate unless there is concern about the possibility of confusion.

A basic and overall configuration or structure of a medication support device 200 according to a control sample of embodiments of the present disclosure is described with reference to FIG. 1A and FIG. 1B.

Figure 1A:
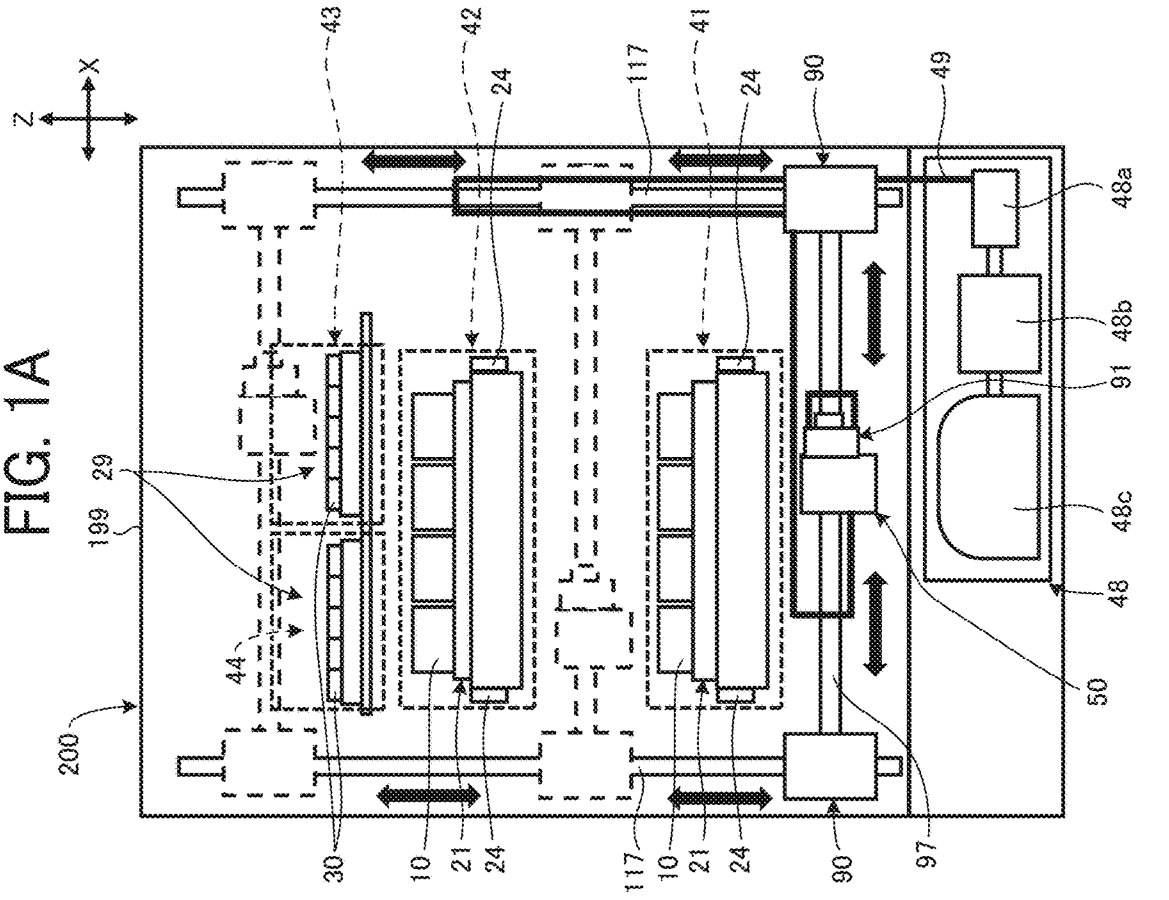
FIG. 1A is a front view of a medication support device in its entirety, according to an embodiment of the present disclosure.

FIG. 1A is a schematic front view of the medication support device 200 in its entirety according to the control sample of the embodiments of the present disclosure.

FIG. 1B is a schematic side view of the medication support device 200 of FIG. 1A, according to the present control sample of the embodiments of the present disclosure.

As illustrated in FIG. 1A and FIG. 1B, a medication support device 200 according to a control sample of the embodiments of the present disclosure includes a plurality of cartridges 10 each of which is also referred to as a container, a plurality of medicine dispensing trays 30, a pickup unit 50, a conveyance unit 90, a first gate 41, a second gate 42, a third gate 43, and a fourth gate 44.

In FIG. 1A and FIG. 1B, the horizontal direction or the right and left directions of the medication support device 200 is defined as an X-direction, where the horizontal direction or the right and left directions of the medication support device 200 is also referred to as the width direction of the medication support device 200, and the front-rear direction or the depth direction of the medication support device 200 is defined as a Y-direction. In FIG. 1A and FIG. 1B, the up and down directions or the orthogonal direction of the medication support device 200 is defined as a Z-direction, where the up and down directions or the orthogonal direction of the medication support device 200 is also referred to as the vertical direction.

Each one of the multiple cartridges 10 serves as a container in which a plurality of medicine packages 2 packing a several kinds of medicines 3 as will be described later are stored upon being stacked on top of each other in layers. The medicine package 2 according to the present embodiment may be referred to simply as a pack or a medicine pack in the following description. The multiple cartridges 10 are arranged at the uppermost portion and a lower portion of a housing 199 of the medication support device 200. The expression "stored upon being stacked on top of each other in layers" in the present disclosure indicates keeping the packs horizontally in such a manner that the front face is viewable.

Each one of the multiple medicine dispensing trays 30 serves as a medicine dispenser in which the prescribed packs conveyed by the conveyance unit 90 are arranged. As illustrated in FIG. 1A, four medicine dispensing trays 30 are positioned between an uppermost group of multiple cartridges 10 and a lower group of multiple cartridges 10. Hereinafter, the position of each one of the multiple medicine dispensing trays 30 where the packs are passed to the medicine dispensing tray 30 for automatic medicine dispensing is referred to as a medicine dispending position 29.

The pickup unit 50 according to the present control sample of the embodiments of the present disclosure serves as a pickup device that picks up a specific pack from one of the multiple cartridges 10. The conveyance unit 90 according to the present control sample of the embodiments of the present disclosure serves as a conveyor that conveys the pack picked up from one of the multiple cartridges 10 by the pickup unit 50.

Each one of the first gate 41 and the second gate 42 according to the present control sample of the embodiments of the present disclosure serve as an entrance and exit gate for the container, which allows one of the multiple cartridges 10 to enter and exit the housing 199. The multiple cartridges 10 are inserted and set in the housing 199 through each one of the first gate 41 and the second gate 42. The open and close door of one of the first gate 41 and the second gate 42 are opened, and the drawer 21 in which the multiple cartridges 10 are aligned is drawn out to the front side. By so doing, the multiple cartridges 10 is inserted or withdrawn.

The third gate 43 and the fourth gate 44 according to the present control sample of the embodiments of the present disclosure serve as a pair of entrance and exit gates for the medicine dispenser, which allow the multiple medicine dispensing trays 30 that are arranged in two rows at the uppermost stage of the medication support device 200 to enter and exit the main structural frame 199. The third gate 43 and the fourth gate 44 are arranged such that the packs can be taken out immediately after the packs (2) are set or inserted into the medicine dispensing tray 30.

In the medication support device 200 according to the present embodiment, two medicine dispensing trays 30 are arranged as illustrated in FIG. 1A. For example, a plurality of medicine dispensing trays are arranged for each time of medication such as a timing in the morning, a timing during the daytime, a timing in the evening, and a timing before going to bed.

The second gate 42 and the third gate 43 for the medicine dispensing tray are also arranged for each one of the medicine dispensing trays 30. Due to such a configuration, another different one of the medicine dispensing trays 30 can be taken out even when the medicine dispersing operation is performed on a particular one of the multiple medicine dispensing trays 30.

The drawers 21 of the multiple cartridges 10 as illustrated in FIG. 1A are arranged in two stages on the upper and lower sides under the pair of medicine dispensing trays 30. However, no limitation is intended thereby, and the drawers 21 may be arranged in two stages on the upper and lower sides with the pair of medicine dispensing trays 30 interposed therebetween. Alternatively, all the drawers 21 may collectively be arranged on an upper side of the pair of medicine dispensing trays 30. Depending on the number of persons in the day-care center or nursing home or day-care center, the multiple cartridges 10 may be arranged in three stages. Such an alternative embodiment may be adopted without affecting the effects to be achieved by the embodiments of the present disclosure.

An outline of the medicine package 2 according to the present embodiment is described below with reference to FIG. 2A, FIG. 2B, FIG. 2C, and FIG. 2D.

Figure 2A:
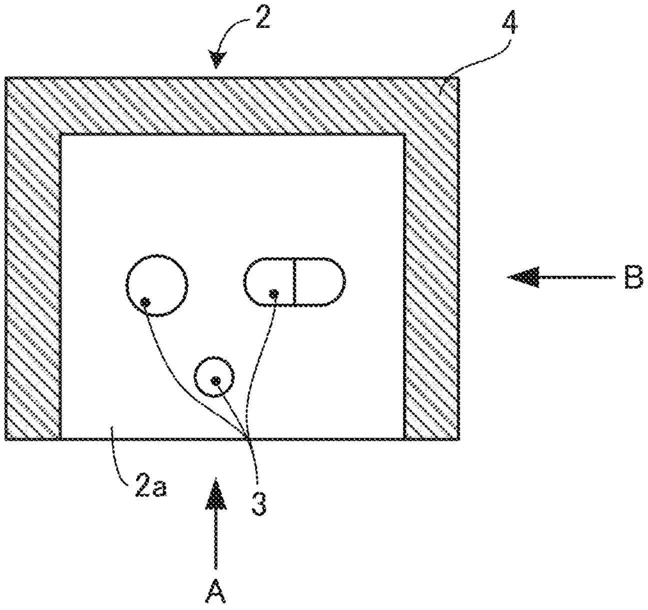
FIG. 2A is a typical plan view of a single medicine package according to an embodiment of the present disclosure.

FIG. 2A is a typical plan view of a single medicine package 2 according to the present embodiment.

Figure 2B:
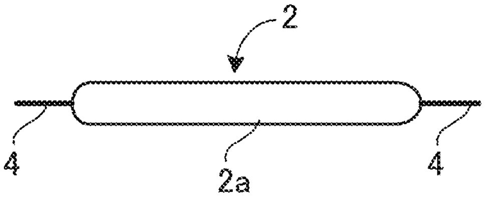
FIG. 2B a side view of the single medicine package of FIG. 2A viewed in a direction indicated by an arrow A, according to an embodiment of the present disclosure.

FIG. 2B a side view of the single medicine package 2 of FIG. 2A viewed in a direction indicated by an arrow A, according to the present embodiment.

Figure 2C:
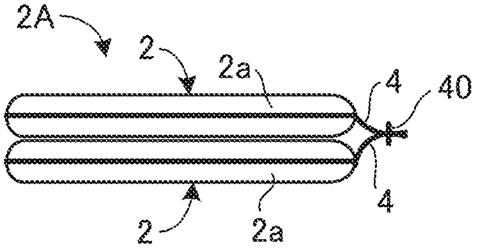
FIG. 2C is a side view of bound medicine packages viewed in a direction indicated by an arrow B, according to an embodiment of the present disclosure.

FIG. 2C is a side view of bound medicine packages 2A viewed in a direction indicated by an arrow B, according to the present embodiment, where such bound medicine packages 2A are obtained by binding the multiple medicine packages 2.

Figure 2D:
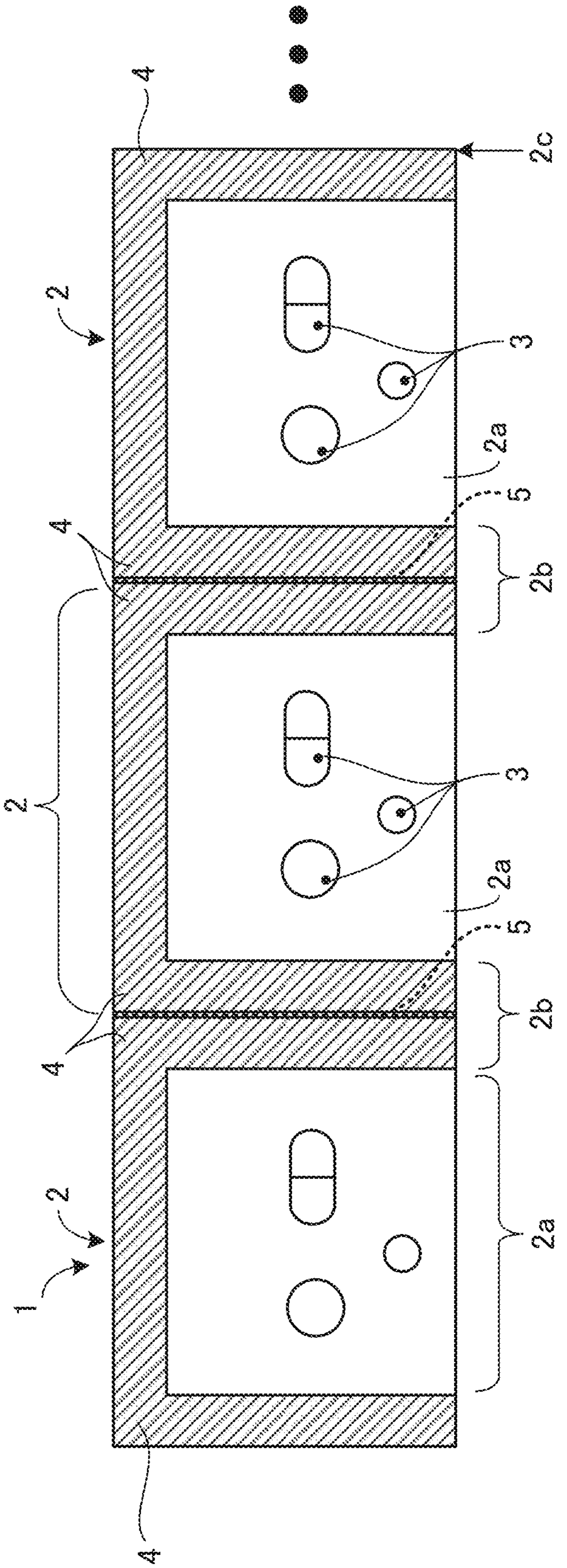
FIG. 2D is a view of a typical form of continuous packs according to an embodiment of the present disclosure.

FIG. 2D is a view of a typical form of continuous packs according to the present embodiment.

In FIG. 2B and FIG. 2C, the medicine package 2 and the bound medicine packages 2A are schematically illustrated.

The medicine pack according to the present embodiment includes the single medicine package 2 and bound medicine packages 2A in which a plurality of medicine packages 2 are stacked on top of each other in layers and bound by a stapler or the like. In FIG. 2C, two medicine packages 2 are bound as the bound medicine packages 2A. The bound medicine packages 2A according to the present embodiment may be referred to simply as bound packages 2A in the following description. Except for FIG. 2A, FIG. 2B, FIG. 2C, and FIG. 2D, a single medicine package 2 is illustrated. However, as a matter of course, the bound packages 2A is also included even when only a single medicine package 2 is illustrated.

As illustrated in FIG. 2A, one medicine package 2 is formed of, for example, a resin film, and a plurality of medicines 3 such as capsules or tablets are packed in small quantities. The medicine package 2 includes a bag 2*a* that covers the medicines 3 and a pressure-bonded portion 4 in which three sides of the bag 2*a* are pressure-bonded or welded. The pressure-bonded portion 4 is hatched in FIG. 2A and FIG. 2D. Typically, the side of the medicine package 2 on the bag 2*a* side is folded into two, and the medicines 3 are packed therebetween. The pressure-bonded portion 4 forms a leakage preventing portion that prevents the medicines 3 from slipping out from the bag 2*a*. Typically, the medicines 3 in one medicine package 2 is a one-time dosage for a patient who takes medicines.

The medicine package 2 is prepared by a drug-dispensing machine installed in a pharmacy or the like. The dispensing sheets that are used for dispending the medicines are rolled long-length sheets, and are perforated between packs. The dispensing sheets are rolled in an overlapping manner, and the medicines 3 to be taken are packed in the space between the sheets. The medicines 3 for a required number of doses are divided in small quantities, and packed into the multiple medicine packages 2 that form a continuous sheet. The three sides other than the folded portion of each one of the multiple medicine packages 2 around the medicines 3 for a single dose are sealed in turn by the pressure-bonded portion 4. The multiple medicine packages 2 that form such a continuous sheet may be referred to as continuous packs 1 in the following description. In the continuous packs 1 that are described with reference to FIG. 2D, the multiple medicine packages 2 are coupled to each other and laid like a belt. In the present embodiment described with reference to FIG. 2D, the medicines 3 for three doses are illustrated. The continuous packs 1 are typical form of drug or medicine that is given or sold at a pharmacy or the like to, for example, a user such as a person who actually takes the medicine 3 in the medicine package 2 and a personal care attendant or assistant who helps or assists the user to take medication, or a staff or the like including a pharmacist, a nurse practitioner, a care manager, or a medication assistant of, for example, various kinds of day-care center, nursing home, or medical institution. For the sake of explanatory convenience, each one of the packs is filled with the medicines 3 of the same form in the following description of the present disclosure. In FIG. 2D, by way of example, each one of the packs is filled with the same capsule and the same tablets. However, no limitation is indicated thereby. As a matter of course, each one of the packs may be filled with different type of medicines depending on, for example, the usage or purposes of the medication.

In the present embodiment described with reference to FIG. 2A, FIG. 2B, FIG. 2C, and FIG. 2D, the medicine package 2 has a rectangular shape in a plan view, and a packaging method in which three sides are crimped and sealed as in the present embodiment is called three-sided packaging in the related art. Most of the drug-dispensing machines available on the market make packs using the three-sided packaging method.

The pressure-bonded portion 4 has a band-like width of about 10 to 15 millimeters (mm), and has higher rigidity than the portion of the bag 2*a* that is a transparent or semitransparent film where the medicines 3 can be visually recognized therethrough. A boundary portion 2*b* that is implemented by perforation 5 is formed in the center of the pressure-bonded portion 4 between a pair of the multiple medicine packages 2 making up the continuous packs 1. The multiple medicine packages 2 are adjacent to each other in an upstream-to-downstream direction. For example, a user who is not handicapped in the hand can obtain one medicine package 2 by tearing off at the perforation 5 by hand or by cutting near the perforation 5 with scissors or a dedicated cutter.

As illustrated in FIG. 2C, bound packages 2A may be used. The bound packages 2A are formed by fastening a plurality of medicine packages 2 at the center of the three sides of the pressure-bonded portions 4 by stapling or the like. In FIG. 2C, two medicine packages 2 are fastened together.

Figure 3:
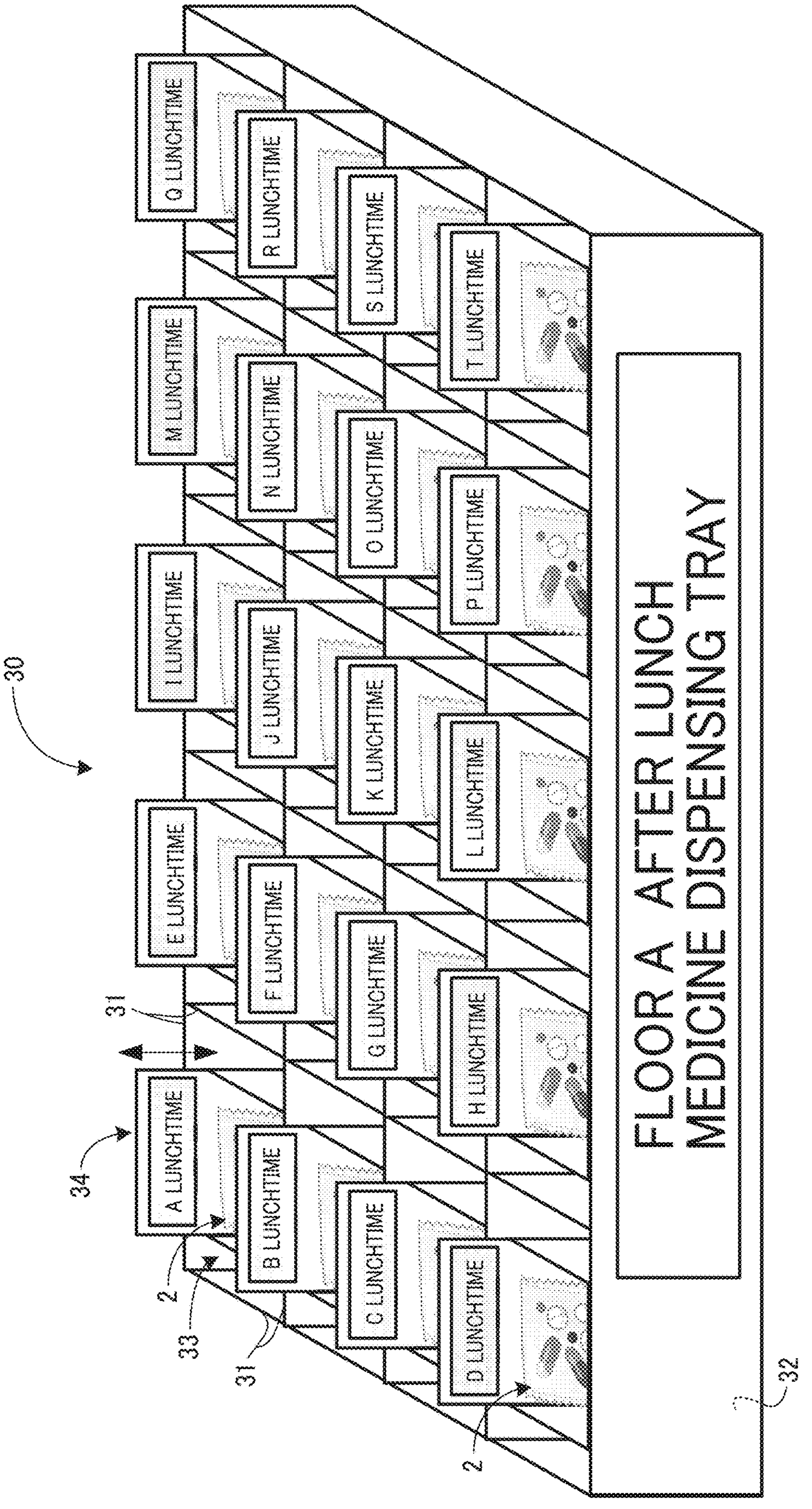
FIG. 3 is an external perspective view of a medicine dispensing tray, illustrating one configuration of the medicine dispensing tray, according to an embodiment of the present disclosure.

FIG. 3 is an external perspective view of the medicine dispensing tray 30 according to the present embodiment.

As illustrated in FIG. 3, each one of the multiple medicine dispensing trays 30 has four upright partition walls 31 that serve as a plurality of dividers for arranging prescribed packs, and is partitioned by those four upright partition walls 31. The twenty partitions 33 that are formed in each one of the multiple medicine dispensing trays 30 can be expressed as the components of a matrix including five columns in the X-direction or the line feed direction and four rows in the Y-direction or the character feed direction. As a result, each one of the twenty partitions 33 of the multiple medicine dispensing trays 30 can be uniquely positioned based on the components and addresses of the matrix of five columns and four rows. Furthermore, each one of the multiple medicine dispensing trays 30 has a bottom wall 32 on which the multiple medicine packages 2 are placed. As described above, each one of the multiple medicine dispensing trays 30 are arranged such that a specific one of the multiple packs will be placed in a specific one of the multiple partitions 33 with reliability by the multiple partition walls 31, which are four partition walls in the present embodiment, and the bottom wall 32 in common, without being mixed up with packs in different one of the multiple partitions 33 or dropping off from the bottom wall 32.

FIG. 3 illustrates one of the multiple medicine dispensing trays 30 where a subdivision box 34 attachable to and detachable from each one of the multiple partitions 33 is used. For example, the multiple subdivision boxes 34 according to the present embodiment hold the multiple medicine packages 2 filled with the medicines 3 to be taken by twenty residents A to T after lunch in day-care center or nursing home. In other words, one of the multiple medicine dispensing trays 30 illustrated in FIG. 3 is used to arrange prescribed packs in a predetermined or specific one of the multiple partitions 33 partitioned by a plurality of dividers through the multiple subdivision boxes 34. The operation of placing the multiple medicine packages 2 in one of the multiple medicine dispensing trays 30 is briefly described later with a case in which the multiple subdivision boxes 34 are not used.

In each one of the multiple partitions 33 of the multiple medicine dispensing trays 30, a setting position or inserting position is determined for each patient who takes medicines depending on a type of medicines in the pack to be taken. In other words, the multiple partitions 33 in one of the multiple medicine dispensing trays 30 may be allocated to a plurality of patients who take medicines at the same time. In a case where a specific patient who takes medicines does not take a medicine at a specific timing, arrangement can be made such that a pack is not given to such a specific patient at the specific timing.

However, no limitation is intended by the multiple medicine dispensing trays described above. According to an alternative embodiment of the present disclosure, each one of the multiple partitions 33 of one of the multiple medicine dispensing trays may be allocated for each time of medication of each patient who takes medicines. More specifically, in such an alternative embodiment of the present disclosure, the multiple partitions 33 may be allocated to each of the patients who take medicines in view of the time of medication of each one of the multiple medicine packages 2 to be taken in the morning, in the daytime, in the evening, or before going to bed. In the multiple medicine dispensing trays 30 according to such an alternative embodiment of the present disclosure, the multiple medicine dispensing trays 30 may be managed on a room by room basis in day-care center or nursing home where a plurality of patients who take medicines reside, and the multiple medicine packages 2 for that day or a couple of days may be dispersed in advance to the multiple medicine dispensing trays 30.

According to the above alternative embodiment, allocating the partitions 33 based on each time of medication such as a time in the morning, a time in the daytime, a time in the evening, and a time before going to bed can prevent the time of medication from being mistaken by patients who take medicines. The configuration or structure of the multiple medicine dispensing trays 30 is not limited to the embodiments of the present disclosure described above, and various kinds of combination are theoretically possible between patients who take medicines and the timing at which the medicines are to be taken. However, such combinations may go beyond the scope of the present disclosure, the description of such combinations is omitted.

The multiple cartridges 10 are described below with reference to FIG. 4A and FIG. 4B.

Figure 4A:
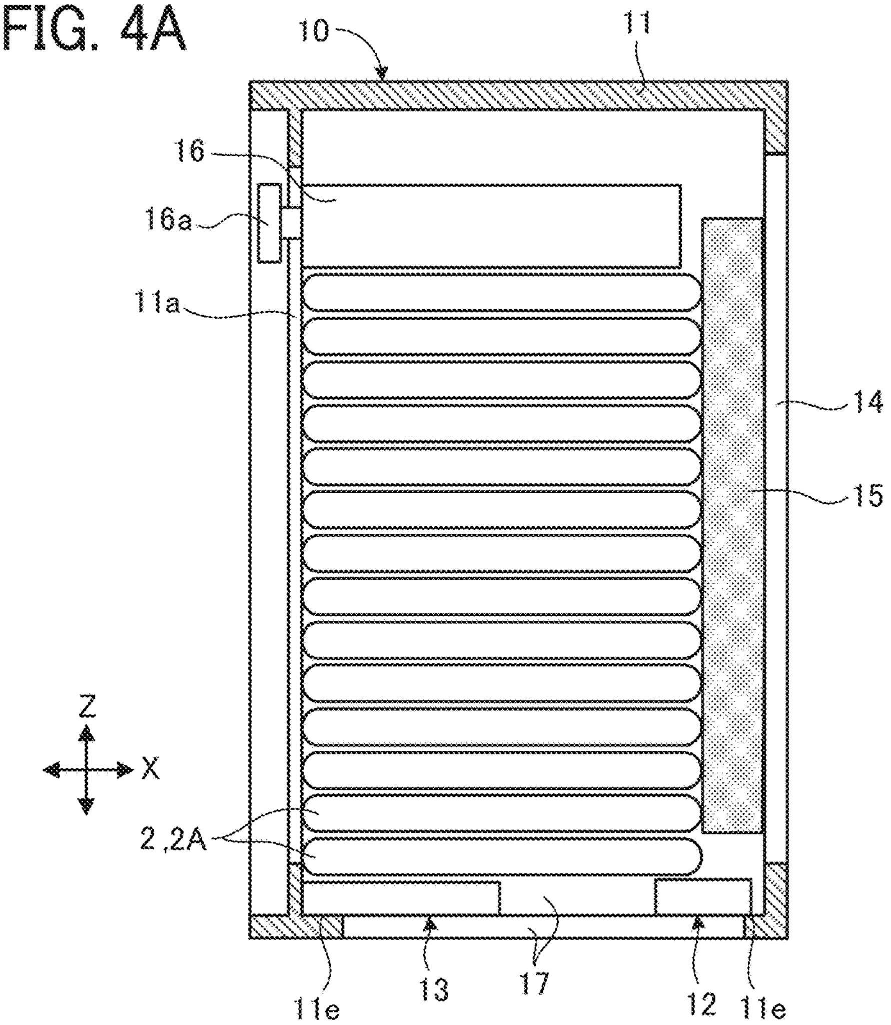
FIG. 4A is a vertical sectional view of a cartridge according to an embodiment of the present disclosure.

FIG. 4A is a vertical sectional view of the cartridge 10 according to the present embodiment.

Figure 4B:
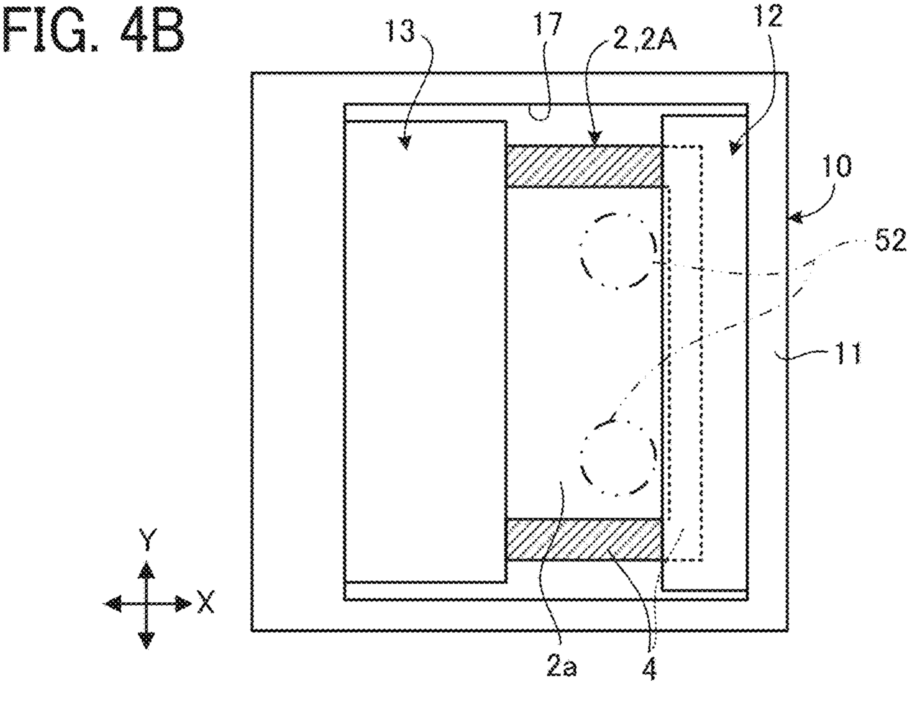
FIG. 4B is a bottom view of a cartridge according to an embodiment of the present disclosure.

FIG. 4B is a bottom view of the cartridge 10 of FIG. 4A, according to the present embodiment.

In the vertical sectional view of the cartridge 10 of FIG. 4A, the medicine package 2 is schematically illustrated in an enlarged and exaggerated manner. For the same purpose, the hatching of the cross sections of the supporters such as the right support portion 12 and the left support portion 13 is also omitted.

For example, each one of the multiple cartridges 10 according to the present embodiment includes a casing 11, a lid 14, a pack pickup slot 17, a movable board 16, a pack posture keeper 15, and a right support portion 12 and a left support portion 13 each of which serves as a support portion (12, 13).

The casing 11 according to the present embodiment stores, for example, a plurality of medicine packages 2 or the bound packages 2A. In the following description, a single medicine package 2 will represent such a plurality of medicine packages 2 or bound packages 2A. The casing 11 is integrally or separately formed using, for example, resin.

The lid 14 according to the present embodiment enables the multiple medicine packages 2 to be loaded or unloaded.

The pack pickup slot 17 according to the present embodiment is formed in a lower portion or a bottom portion of the casing 11, and is used to pick up the medicine package 2 in one of the multiple cartridges 10. Moreover, the pack pickup slot 17 according to the present embodiment allows the medicine package 2, which is picked up from one of the multiple cartridges 10 by the pickup unit 50 (see, for example, FIG. 1A, FIG. 1B, FIG. 7A, and FIG. 7B), to pass therethrough.

The movable board 16 according to the present embodiment prevents the medicine package 2 from falling out, and makes the lowermost one of the multiple medicine packages 2 move close to the pack pickup slot 17 after the first one of the maximum number of medicine packages 2 that can be stored in the casing 11 is picked up.

The pack posture keeper 15 keeps the posture of the medicine package 2.

The right support portion 12 and the left support portion 13 also support or hold the medicine package 2 in the casing 11.

In the present control sample of the above embodiments of the present disclosure, the to-be-picked-up portion of one of the multiple medicine packages 2 to be picked up from one of the multiple cartridges 10 by the pickup unit 50 is at a lower portion or bottom portion of the corresponding one of the multiple cartridges 10. In other words, the to-be-picked-up portion includes the pack pickup slot 17, and the right support portion 12 and the left support portion 13 that serve as a pair of support portions or supporting member and support, at a plurality of points, one of the multiple medicine packages 2 to be picked up from one of the multiple cartridges 10.

When one of the multiple medicine packages 2 is picked up from one of the multiple cartridges 10 by the pickup unit 50, the right support portion 12 and the left support portion 13 allow one of the multiple medicine packages 2 to pass through. On the other hand, when any one of the multiple medicine packages 2 is not to be picked up from one of the multiple cartridges 10, the multiple medicine packages 2 are to be stored and held in the casing 11. In order to achieve that, the right support portion 12 and the left support portion 13 are configured to restrict the passage of one of the multiple medicine packages 2

As described above, the right support portion 12 and the left support portion 13 according to the present embodiment serve as a pair of support portions that support or hold the multiple medicine packages 2 in the one of the multiple cartridges 10, and each one of the right support portion 12 and the left support portion 13 is fixed and immovable such that one of the multiple medicine packages 2 can be picked up in a stable manner from one of the multiple cartridges 10 by the pickup unit 50.

The right support portion 12 and the left support portion 13 according to the present embodiment are a pair of fixation members that are fixed or attached to the pair of bottom-wall inner surfaces 11*e* of the right bottom-wall edge and left bottom-wall edge of the pack pickup slot 17, respectively.

The pack pickup slot 17 according to the present embodiment has both a function to allow the pair of suction pads 52 of the pickup unit 50 illustrated in FIG. 4B, which serves as an air suction unit or a suction unit, to pass therethrough in order to pick up one of the multiple medicine packages 2 and a function to allow the picked-up medicine package 2 and the pair of suction pads 52 to pass therethrough.

In one the multiple cartridges 10 illustrated in FIG. 4B, a pair of positions at which the pair of suction pads 52 adsorb or suck up one of the multiple medicine packages 2 stored in one of the multiple cartridges 10, as will be described later in detail with reference to FIG. 8A, FIG. 8B, FIG. 8C, FIG. 8D, FIG. 8E, and FIG. 8F, are indicated by a pair of ring-shaped dot-dot-dash lines. Such a pair of positions may be referred to as a pair of suction pad positions in the following description.

The right support portion 12 and the left support portion 13 support the multiple medicine packages 2 in one of the multiple cartridges 10 such that the multiple medicine packages 2 in one of the multiple cartridges 10 do not fall from the pack pickup slot 17. As will be described later in detail in regard to the operation of the pickup unit 50, the right support portion 12 and the left support portion 13 have a positional relation in which one of the multiple medicine packages 2 is sucked by the pair of suction pads 52 at two suction pad positions in the Y-direction near both ends of the right support portion 12 when the lowermost one of the multiple medicine packages 2 in one of the multiple cartridges 10 is picked up while being sucked by the pair of suction pads 52. When the lowermost one of the multiple medicine packages 2 is picked up from one of the multiple cartridges 10 by the pair of suction pads 52, the pair of suction pads 52 pass near both ends of the right support portion 12 in the Y-direction to suck and hold one of the multiple medicine packages 2.

As illustrated in FIG. 4B, two points at which the suction pad 52 contacts are arranged near both ends of the right support portion 12 in the Y-direction. Due to such a configuration, the possibility of an error in which the suction by the pair of suction pads 52 is disabled can be avoided and prevented, and the picking up operation can successfully be done. In other words, as both ends of the multiple medicine packages 2 in the Y-direction are sucked by the pair of suction pads 52, the bag 2*a* of the medicine package 2, which is made of film, is stretched and can withstand the deformation. Accordingly, both reliable support or holding of the multiple medicine packages 2 in one of the multiple cartridges 10 and smooth removal of one of the multiple medicine packages 2 can be achieved.

The pack posture keeper 15 is formed of sponge rubber having appropriate elasticity. The movable board 16 is made of, for example, resin or metal. The pack posture keeper 15 and the movable board 16 according to the present embodiment hold the posture of the multiple medicine packages 2 under normal operating conditions in the casing 11. As explicitly illustrated in FIG. 4A, the posture of the multiple medicine packages 2 is held orderly in the Z-direction in a substantially horizontal state. In order to achieve the above-described function, the movable board 16 is arranged to move at least one of the multiple medicine packages 2 left in the casing 11 toward the pack pickup slot 17 as moving downward in the casing 11 in the Z-axis direction by its own weight. As illustrated in FIG. 4A, a long groove 11*a* that extends in the Z-direction with predetermined width in the X-direction is formed in the side wall of the casing 11. A shaft 16*a* with a flange is arranged at one end of the movable board 16 so as to protrude from the long groove 11*a*. As the shaft 16*a* of the movable board 16 is guided in the Z-direction parallel to the long groove 11*a*, the posture of the multiple medicine packages 2 can be held in the Z-direction. In FIG. 4A and FIG. 4B, the multiple medicine packages 2 in the multiple cartridges 10 are stacked on top of each other in layers in a substantially horizontal state. However, in actuality, left portions of the medicine packages 2 in FIG. 4A and FIG. 4B filled with the medicines 3 are expanding.

A set of the multiple medicine packages 2 are orderly stored in the casing 11 toward the upper side from the pack pickup slot 17 on the right support portion 12 and the left support portion 13. The timing at which the multiple medicine packages 2 are supplied into one of the multiple cartridges 10 may be, for example, the timing at which a patient who takes medicines or occupant is examined in a day-care center or nursing home, which is typically once a two weeks, or the timing at which the multiple medicine packages 2 in one of the multiple cartridges 10 run out. When some medicine packages 2 are left in one of the multiple cartridges 10 at the time of replenishment, such replenishment is continued from the back of the remaining medicine packages 2. Under normal operating conditions, the above-described setting of the multiple medicine packages 2 into one of the multiple cartridges 10 and the replenishment of the multiple medicine packages 2 are done by a staff or the like in a day-care center or nursing home. However, no limitation is indicated thereby. In particular, in configurations where cartridges are used instead of containers and setting or replenishment of the medicine packages 2 are done automatically, the setting or replenishment of the medicine packages 2 may be done differently.

The lid 14 is used by a staff or the like who works at a day-care center or nursing home to enable loading or unloading of the multiple medicine packages 2 stored in one of the multiple cartridges 10, and as illustrated in FIG. 4A, is formed with wide length in the Z-direction of the casing 11 and has a predetermined opening width.

As illustrated in FIG. 4A, the types of the multiple medicine packages 2 in one of the multiple cartridges 10 are sorted or divided based on the timings at which medicines are taken. For example, one cartridge contains medicines to be taken in fourteen days in the morning by Mr. or Ms. A. In view of the above circumstances, if Mr. or Ms. A takes the medicines not only in the morning but also in the daytime or in the evening, or before going to bed, four cartridges 10 are required in total.

However, no limitation is indicated thereby. For example, in an alternative embodiment of the present disclosure, a single cartridge 10 may be prepared for each person or patient who takes medicines. In such cases, for example, a pack to be used in the morning on day one, a pack to be used at lunchtime on day one, a pack to be used in the evening on day one, a pack to be used before going to bed on day one, a pack to be used in the morning on day two, a pack to be used at lunchtime on day two, and a pack to be used in the evening on day two may be stored in the order listed upward from the pack pickup slot 17 parallel to the direction in which packs are taken out from the multiple cartridges 10.

In the present control sample of the above embodiments of the present disclosure, the right support portion 12 and the left support portion 13 are fixed to the bottom-wall inner surface 11*e* of the pack pickup slot 17 of the casing 11 such that one of the multiple medicine packages 2 can be picked up in a steadily stable manner from one of the multiple cartridges 10 by the pickup unit 50. In other words, the right support portion 12 and the left support portion 13 according to the present embodiment are fixed when the right support portion 12 and the left support portion 13 hold both ends of the medicine pack such as the medicine package 2 or the bound packages 2A around the pack pickup slot 17 arranged at the lower portion of one of the multiple cartridges 10.

An end of the bottom one of the multiple medicine packages 2 to be adsorbed by, for example, an adsorption system is supported by the right support portion 12, and the other end of the bottom one of the multiple medicine packages 2 is supported by the left support portion 13. Due to such a configuration, the medicine packages 2 that are set and stored in the cartridge 10 do not drop.

The right support portion 12 and the left support portion 13 are different in the length of the portion that support the multiple medicine packages 2, and the length of portion of the right support portion 12 that support the multiple medicine packages 2 is shorter than that of the left support portion 13. As will be described later in detail with reference to FIG. 8C, when the lowermost one of the multiple medicine packages 2 stored in the cartridge 10 is adsorbed or sucked by the pair of suction pads 52 and is pulled out from the cartridge 10, the medicine pack is bent due to its elasticity. Accordingly, the medicine pack can easily be pulled out.

As the pair of support portions including the right support portion 12 and the left support portion 13 are of fixed type, the front end of the next one of the multiple medicine packages 2 to be taken out can be reliably held and does not jump out or fall off together with one of the multiple medicine packages 2 that is being taken out. As the pair of support portions including the right support portion 12 and the left support portion 13 do not swing or rotate, the medicine package 2 are held with high stability with no deformation or the like due to unintentional nipping or pressing in the returning operation.

The attaching and detaching mechanisms and operations of the multiple cartridges 10 that are arranged in the drawer 21 are described below with reference to FIG. 5 and FIG. 6.

Figure 5:
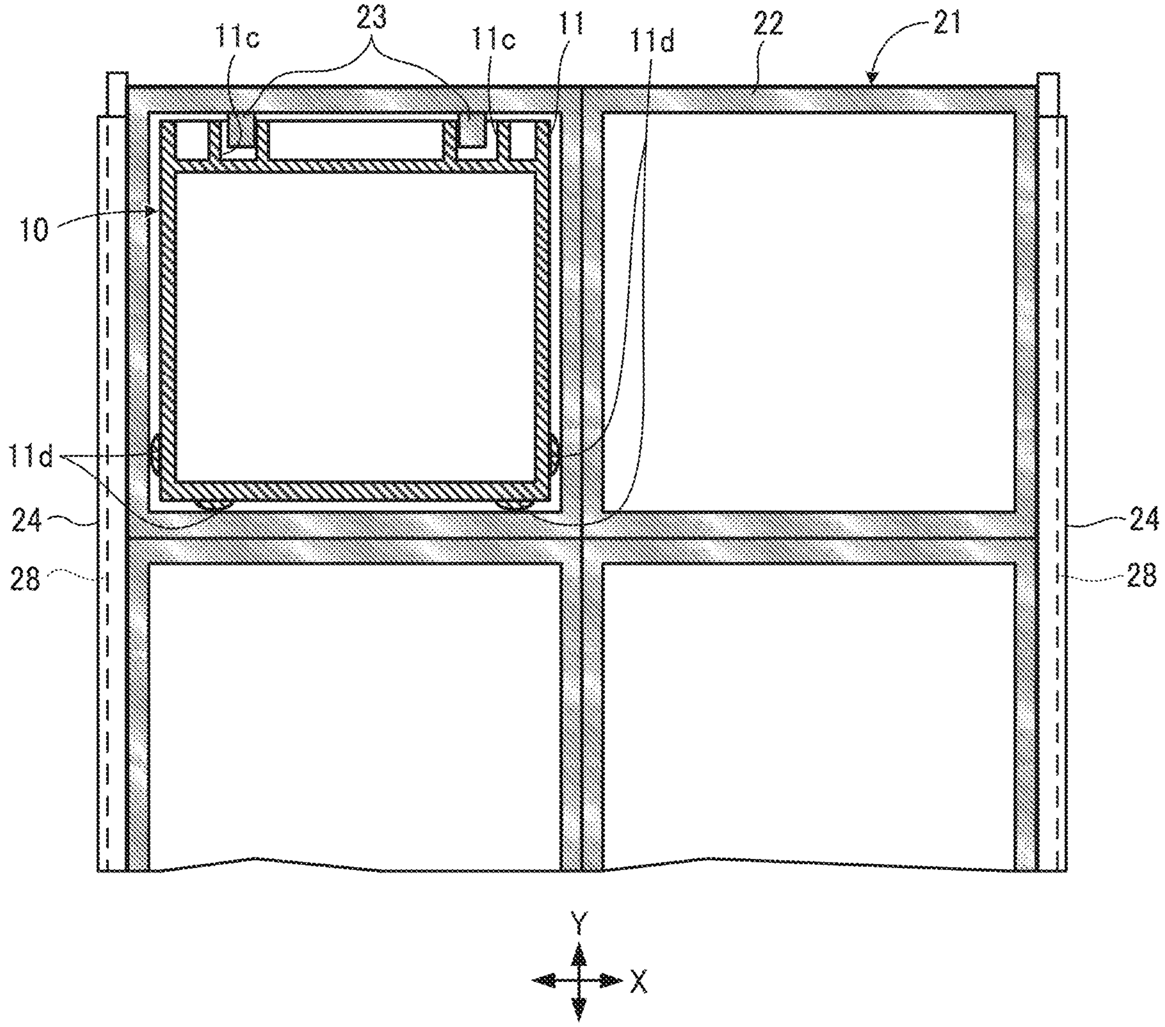
FIG. 5 is a schematic plan sectional view of the attaching and detaching mechanisms for a cartridge, according to an embodiment of the present disclosure.

FIG. 5 is a schematic plan sectional view of the attaching and detaching mechanisms for a container, which are arranged on the drawer 21, according to the present embodiment.

Figure 6:
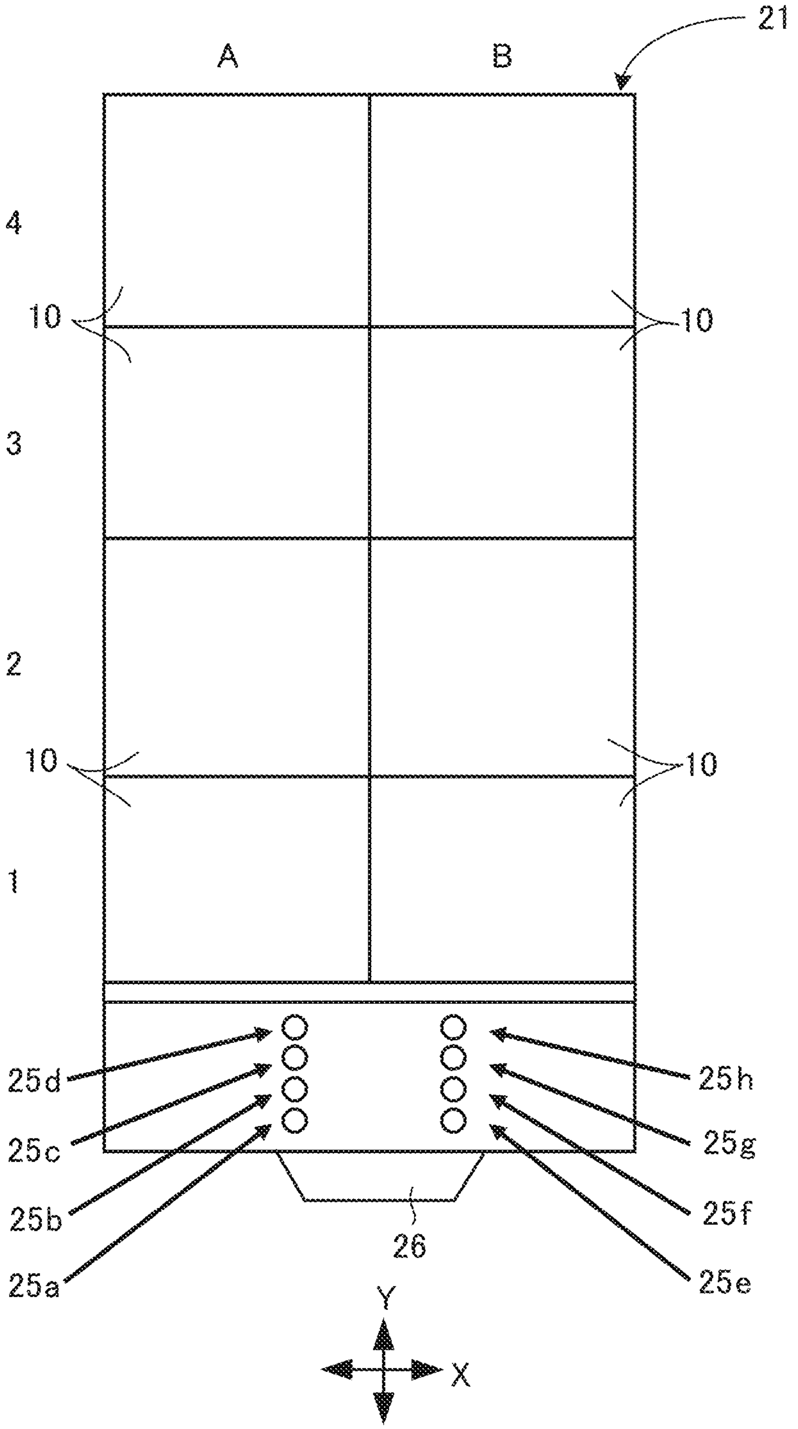
FIG. 6 is a plan view of a cartridge according to an embodiment of the present disclosure, and illustrates the mechanisms for recognizing the cartridge.

FIG. 6 is a schematic plan view of the drawer 21 and illustrates the mechanisms for recognizing the container, which are arranged on the drawer 21, according to the present embodiment.

As illustrated in FIG. 5, a plurality of cartridges 10 can be attached to or detached from the drawer 21. The casing 22 of the drawer 21 is provided with a pair of slide rails 24 on the right and left outer side walls, respectively, and each one of the pair of slide rails 24 is slidable with one of the multiple rails 28 provided for the housing 199 (see FIG. 1A and FIG. 1B). Due to such a configuration, the drawer 21 can be attached or detached by being pulled out from the housing 199 (see FIG. 1A and FIG. 1B) through the engagement between the slide rail 24 and the one of the multiple rails 28 of the housing 199.

As illustrated in FIG. 5, the cartridge 10 is attached to and detached from the drawer 21 through the engagement and disengagement between a pair of concave portions 11*c* on the external wall of the casing 11 of the cartridge 10 and a pair of convex portions 23 that are formed on the inner wall of the casing 22 of the drawer 21 and protrude inwardly and the engagement and disengagement between the inner wall of the casing 22 and four hemispherical protrusions 11*d* on the external wall of the casing 11. With the above-described attaching and detaching mechanism of the drawer 21, the multiple cartridges 10 can be attached or detached easily and with good operability.

In the above embodiments of the present disclosure, attachment and detachment are enabled by the coupling or engagement of concave and convex portions. However, no limitation is intended thereby, and an elastic member may be arranged in the gap between the inner wall of the casing 22 and the external wall of the casing 11 to enable attachment and detachment. Alternatively, a configuration or structure using magnetic force or a snap-fit assembly method may enable attachment and detachment.

As illustrated in FIG. 6, the drawer 21 according to the present embodiment is provided with an information display device such as a plurality of light-emitting diodes (LEDs) 25*a*, 25*b*, 25*c*, 25*d*, 25*e*, 25*f*, 25*g*, and 25*h* around a grip 26 that is held by hand to insert or withdraw the drawer 21. Due to such a configuration, the arrangement of the multiple cartridges 10 can easily be figured out. More specifically, due to such a configuration, at what position the cartridge 10 in focus is placed in the drawer 21 can easily be figured out at a glance. In FIG. 5, the light-emitting diode (LED) 25*a* is used to detect the presence or absence of one of the multiple cartridges 10 attached to or detached from A1 of the drawer 21. A1 denotes a position or partition that is uniquely determined in the vertical columns and horizontal rows. In a similar manner to the above, the LED 25*b*, the LED 25*c*, the LED 25*d*, the LED 25*e*, the LED 25*f*, the LED 25*g*, and the LED 25*h* detect the presence or absence of one of the multiple cartridges to be attached to or detached from A2, A3, A4, B1, B2, B3, and B4 of the drawer 21, respectively.

With the use of an information display device such as the LED 25*a*, LED 25*b*, the LED 25*c*, the LED 25*d*, the LED 25*e*, the LED 25*f*, the LED 25*g*, and the LED 25*h*, there is a possibility that a staff or the like who is an operator and attaches or detaches one of the multiple cartridges 10 mix up which one to attach or detach. In order to avoid such a situation, for example, the presence or absence of the cartridges 10 may be electronically determined by, for example, a sensor or a switch.

The container may be provided with for example, a number, a bar code, a quick response (QR) code (registered trademark), or a non-contact integrated circuit (IC) tag such that each one of the containers will be identifiable. It is desired that the system be programmed to remember what container stores whose medicines. Subsequently, the drawer to which the multiple containers are attached is set in the housing 199 of the medication support device 200, and each one of the multiple containers is identified by the medication support device 200. Due to such a configuration, a desired pack can be picked up in the medication support device 200 without causing any errors.

A configuration and operation of a pickup unit 50 will be described below with reference to FIG. 7A, FIG. 7B, FIG. 8A, FIG. 8B, FIG. 8C, FIG. 8D, FIG. 8E, FIG. 8F, FIG. 9A, and FIG. 9B.

Figure 7A:
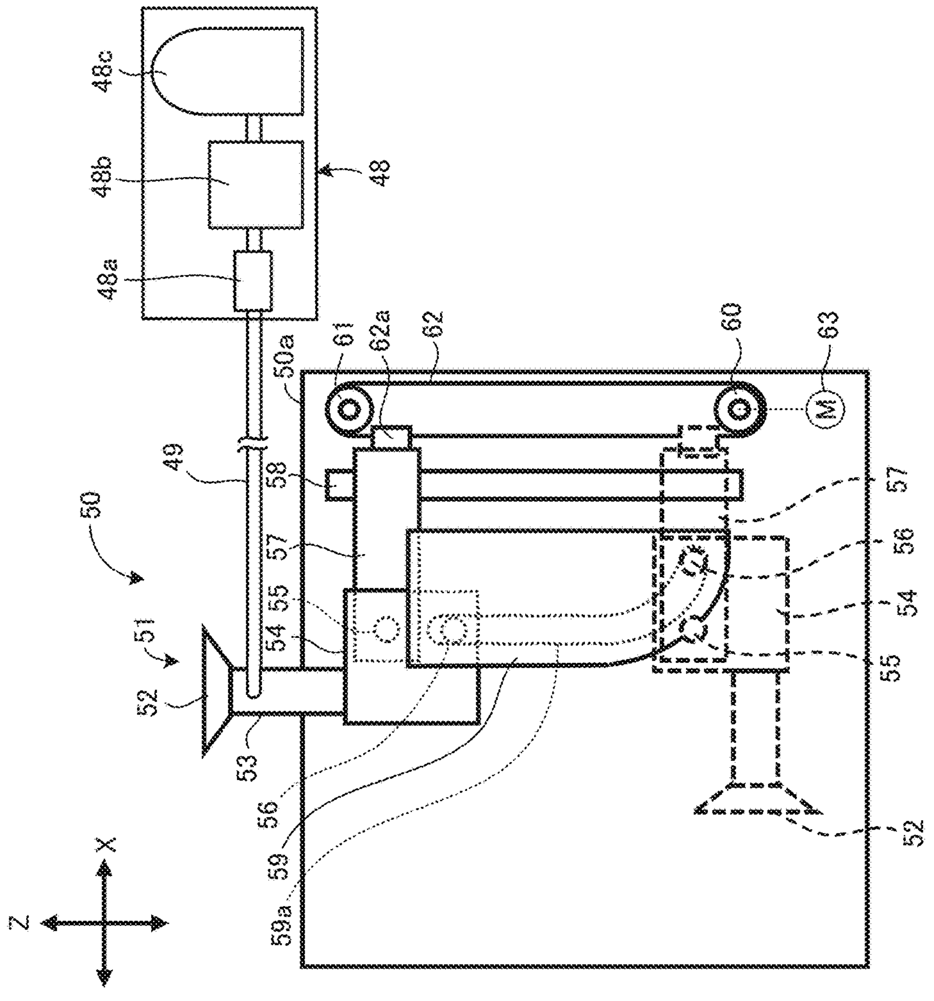
FIG. 7A is a front view of a pickup unit, illustrating a configuration or structure of the pickup unit, according to an embodiment of the present disclosure.

FIG. 7A is a front view of the pickup unit 50, illustrating a configuration or structure of the pickup unit 50, according to the present embodiment.

Figure 7B:
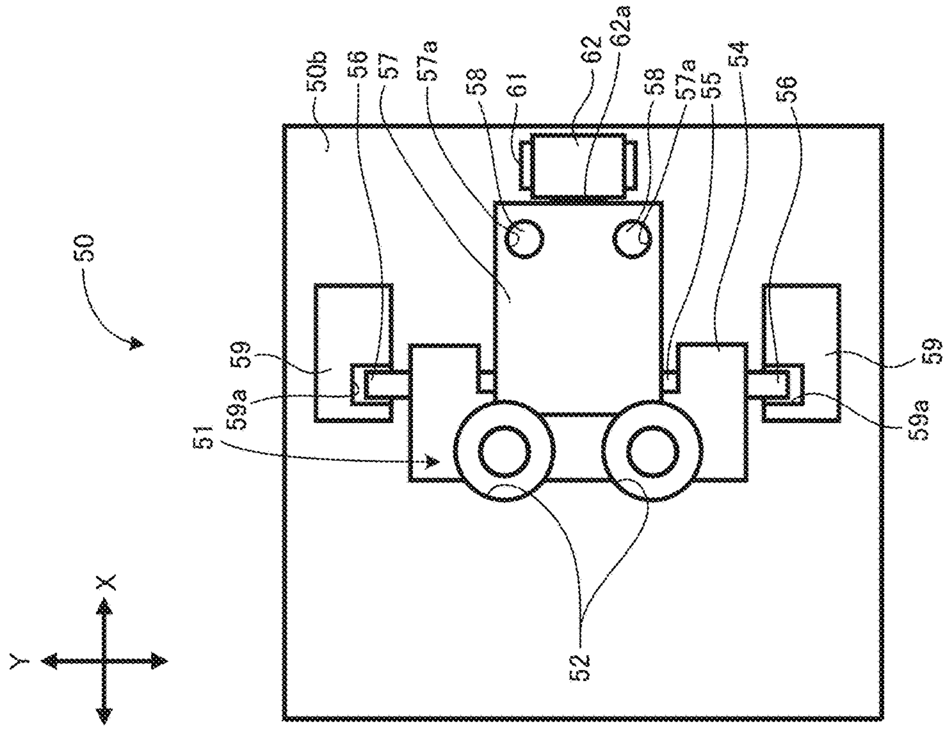
FIG. 7B is a plan view of the pickup unit illustrated in FIG. 7A, according to an embodiment of the present disclosure.

FIG. 7B is a plan view of the pickup unit 50 illustrated in FIG. 7A, according to the present embodiment.

FIG. 8A, FIG. 8B, FIG. 8C, FIG. 8D, FIG. 8E, FIG. 8F, FIG. 9A, and FIG. 9B are front views of the pickup unit 50 illustrating the progression of the operation of the pickup unit 50, according to the present embodiment.

As illustrated in FIG. 7A and FIG. 7B, the pickup unit 50 according to the present embodiment includes a suction device 51 that serves as a suction unit and picks up and holds one of the multiple medicine packages 2 from one of the multiple cartridges 10. The suction device 51 has a suction pump 48 using air (see the block diagram of FIG. 11 as will be described later in detail), and the suction pump 48 places the suction device 51 under negative pressure. By so doing, one of the multiple medicine packages 2 is successfully sucked up.

The suction pump 48 according to the present control sample of the embodiments of the present disclosure includes a negative-pressure generator 48*a*, an air compressor 48*b*, and an air tank 48*c*. As illustrated in FIG. 1A and FIG. 1B, the suction pump 48 is arranged at the bottom of the housing 199 of the medication support device 200. The suction pump 48 is connected to the suction device 51 through an air tube 49. The air tube 49 according to the present control sample of the embodiments of the present disclosure is arranged together with, for example, a pair cable and a wire harness so as not to be stretched even when the pickup unit 50 moves inside the medication support device 200. In other words, as illustrated in FIG. 1A and FIG. 1B, the air tube 49 according to the present control sample of the embodiments of the present disclosure has a one-turn path for each one of the X-axis, the Y-axis, and the Z-axis. Firstly, the air tube 49 is extended from the negative-pressure generator 48*a* in the Z-axis direction and makes one turn. Secondly, the air tube 49 is extended from the negative-pressure generator 48*a* in the X-axis direction and makes one turn. Finally, the air tube 49 is extended from the negative-pressure generator 48*a* in the Y-axis direction and makes one turn, and is coupled to the suction device 51.

The suction pump 48 may be arranged in the pickup unit 50 or may be disposed at another portion in the medication support device 200. When the suction pump 48 is arranged inside the medication support device 200, the suction device 51 is connected to the suction pump 48 through a communicating member such as an air tube.

The suction device 51 has a suction pad 52 that communicates with the suction pump 48 and sucks one of the multiple medicine packages 2, and a suction duct 53 coupled to the pair of suction pads 52. The suction pad 52 according to the present embodiment serves as an air suction unit or a suction member that sucks up and picks up one of the multiple medicine packages 2 in one of the multiple cartridges 10. As described above, the upper ends of the pair of suction pads 52 as illustrated in FIG. 7A is arranged to absorb one of the multiple medicine packages 2. The bottom ends of the pair of suction pads 52 as illustrated in FIG. 7A is attached and fixed to the upper end of the suction duct 53 as illustrated in FIG. 7A. The bottom end of the suction duct 53 as illustrated in FIG. 7A is attached and fixed to the suction-pad supporting member 54. A pair of suction pads 52 and suction ducts 53 are arranged in the Y-direction.

The pickup unit 50 according to the present embodiment is provided with a posture changing unit used to change the posture of one of the multiple medicine packages 2 picked up from one of the multiple cartridges 10 to a substantially vertical posture. The posture changing unit in the pickup unit 50 may include, for example, a suction-pad supporting member 54 coupled to a suction device base 57 through a rotation axis 55, a guide unit 59 formed with a guide groove 59*a* having a specific shape, a guide axis 56 that is consistently fitted into the guide groove 59*a* of the guide unit 59 to guide the suction-pad supporting member 54, and a suction unit lifting and lowering unit.

The suction-pad supporting member 54 is coupled to the suction device base 57 through the rotation axis 55. The suction-pad supporting member 54 may be may rotatably or pivotably be arranged around the rotation axis 55 fixed to the suction-pad supporting member 54 within a range of a predetermined angle. Alternatively, the suction-pad supporting member 54 may be may rotatably or pivotably be arranged around the rotation axis 55 fixed to the suction device base 57. In other words, in FIG. 7A and FIG. 7B, the distance between the center of the rotation axis 55 and the center of a guide rod 58 in the X-direction is kept constant at all times when the suction device base 57 moves along the guide rod 58 in the up and down directions parallel to the Z-direction. The guide rod 58 will be described later in detail.

The suction pad lifting and lowering unit includes a pair of guide rods 58 that are arranged separately in the Y-direction and guides the suction device base 57 in the Z-direction, an endless belt 62 looped around a driving pulley 60 and a driven pulley 61, and a suction device lifting and lowering motor 63 coupled to the driving pulley 60 through a driving power conveyor such a gear or a belt. The suction device lifting and lowering motor 63 according to the present embodiment serves as a driver circuit or a driving source of the suction pad lifting and lowering unit.

The suction device base 57 according to the present embodiment is coupled and fixed to the endless belt 62 at a belt grip 62*a* fixed to the right end of the suction device base 57.

The pair of guide rods 58 are arranged at two different positions in the Y-direction, and extend in the Z-direction. The bottom ends of those guide rods 58 are fixed to the base frame 50*b* of the picking-up frame 50*a* provided for the pickup unit 50.

A pair of guiding holes 57*a* into which the pair of guide rods 58 are inserted are formed around a right end of the suction device base 57.

The pulley axis of each one of the driving pulley 60 and the driven pulley 61 is rotatably supported by an immovable member on the picking-up frame 50*a*. The suction device lifting and lowering motor 63 is fixed to an immovable member provided for the picking-up frame 50*a* of the pickup unit 50. The suction device lifting and lowering motor 63 is also a driver circuit to be controlled (see FIG. 11 as will be described later in detail) of the suction unit lifting and lowering unit.

When the suction device base 57 is lifted or lowered by the operation of the suction device lifting and lowering motor 63, the suction device base 57 is moved along the pair of guide rods 58 in the Z-direction. Accordingly, the posture of the suction device base 57 on the XY plane can be kept constant in a substantially horizontal state.

The suction unit lifting and lowering unit is not limited to the above-described up-and-down reciprocating mechanism driven by a belt. Alternatively, for example, the suction unit lifting and lowering unit may have a reciprocating linear motion mechanism using a rack and pinion.

A pair of guide units 59 are arranged on both sides of the suction device 51 in the Y-direction with the suction-pad supporting member 54 interposed therebetween, and the bottom ends of the pair of guide units 59 are fixed to the base frame 50*b*.

The guide axis 56 is arranged so as to protrude from both ends of the suction-pad supporting member 54 in the Y-direction, and is consistently fitted into the guide groove 59*a* of the guide unit 59 to guide the suction-pad supporting member 54. As illustrated in FIG. 7A, the guide axis 56 is provided below the rotation axis 55 of the suction-pad supporting member 54 in the Z-direction with a certain distance from the rotation axis 55.

When the suction device base 57 is moved in the Z-direction by the operation of the suction device lifting and lowering motor 63, the guide axis 56 of the suction-pad supporting member 54 is moved in the Z-direction parallel to the guide groove 59*a* having a specific shape while maintaining the posture of the suction device base 57 on the XY plane constant in a substantially horizontal state. Due to such a configuration, the posture of the suction pad 52 can be rotated by approximately 90 degrees. In FIG. 7A, the suction device 51 that is rotated by approximately 90 degrees is indicated by thick broken lines.

In the present embodiment, the expression "substantially horizontal state" indicates that the posture of a particular element is within a specific range of tolerance for angle with respect to the horizontal in addition to a state in which the position of a particular element is horizontal.

The guide groove 59*a* having a specific shape includes the first guide groove portion that extends in the Z-direction with relatively great length so as to hold the posture of the pair of suction pads 52 upward as indicated by solid lines in FIG. 7A through the suction-pad supporting member 54 in a substantially horizontal state as guided by the guide axis 56. Moreover, the guide groove 59*a* includes the second guide groove portion that gently draw an obtuse and shallow arc to the right side as it goes downward to rotate the posture of the suction-pad supporting member 54 and the pair of suction pads 52 by approximately 90 degrees, and the first guide groove portion and the second guide groove portion communicate with each other and are coupled to each other.

Due to the relation between the guide groove 59*a* and the cross-axis distance between the rotation axis 55 and the guide axis 56 as described above, the pair of suction pads 52 can take various kinds of posture by moving about the rotation axis 55 that serves as a fulcrum. For example, the posture of the suction pad 52 can be rotated by approximately 90 degrees.

The operation of the pickup unit 50 is described below with reference to FIG. 8A, FIG. 8B, FIG. 8C, FIG. 8D, FIG. 8E, FIG. 8F, FIG. 9A, and FIG. 9B.

FIG. 8A, FIG. 8B, FIG. 8C, FIG. 8D, FIG. 8E, and FIG. 8F are front views of the pickup unit 50 illustrating the progression of the operation of the pickup unit 50, according to the present embodiment.

Figure 8A:
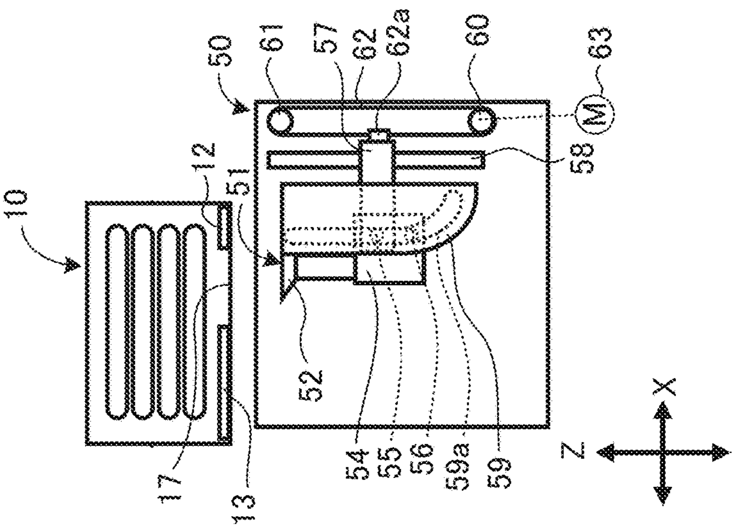
FIG. 8A, FIG. 8B, FIG. 8C, FIG. 8D, FIG. 8E, and FIG. 8F are front views of a pickup unit illustrating the progression of the operation of the pickup unit, according to an embodiment of the present disclosure.
Figure 8B:
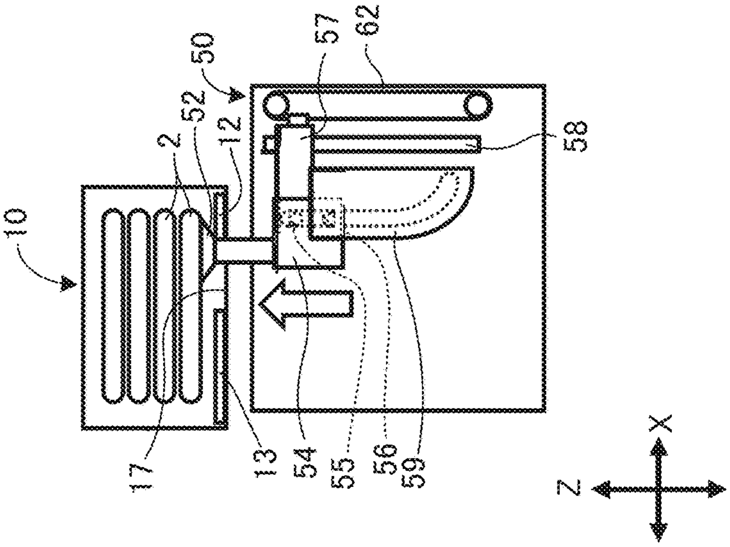
Figure 8C:
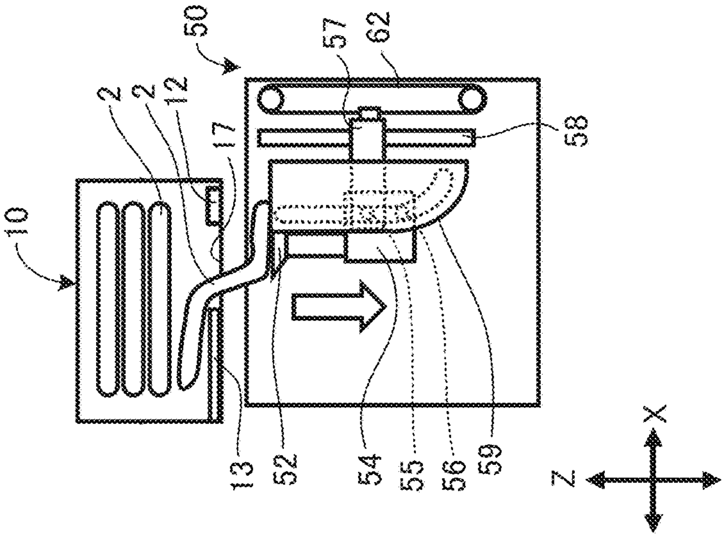
Figure 8F:
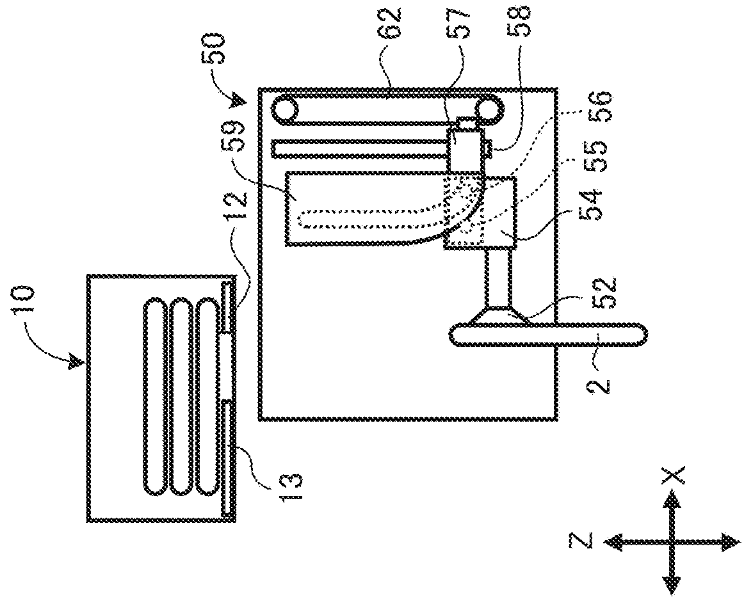
Figure 8E:
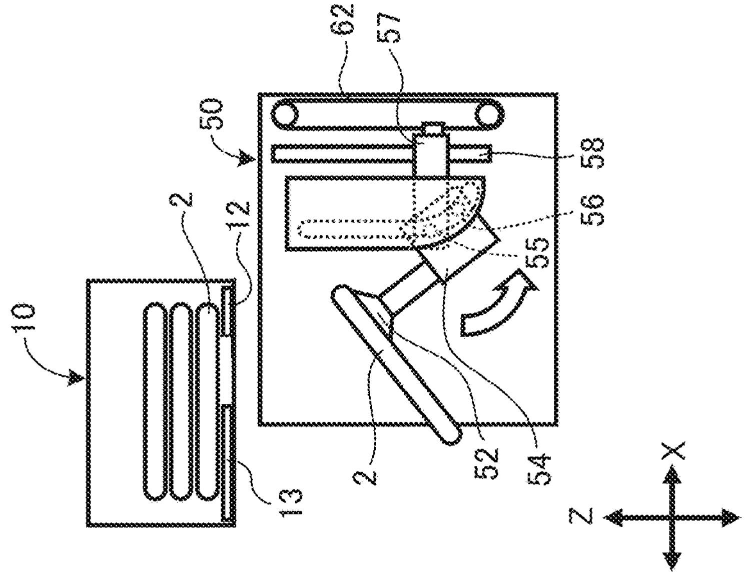
Figure 8D:
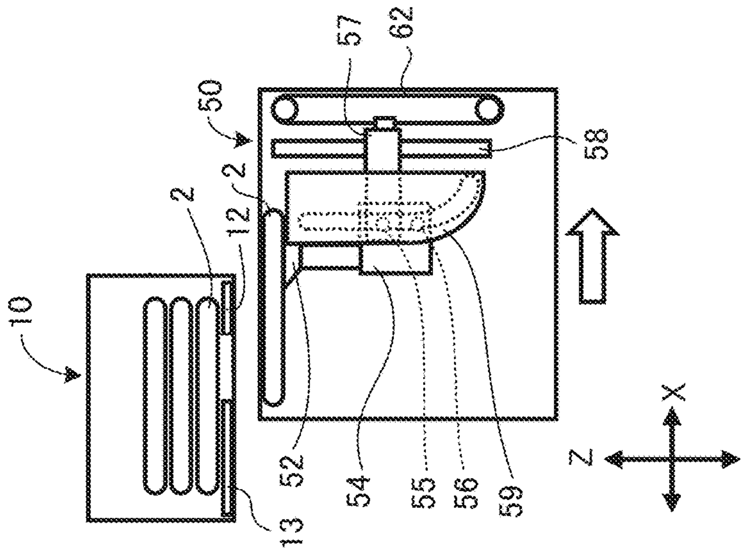
Figure 9A:
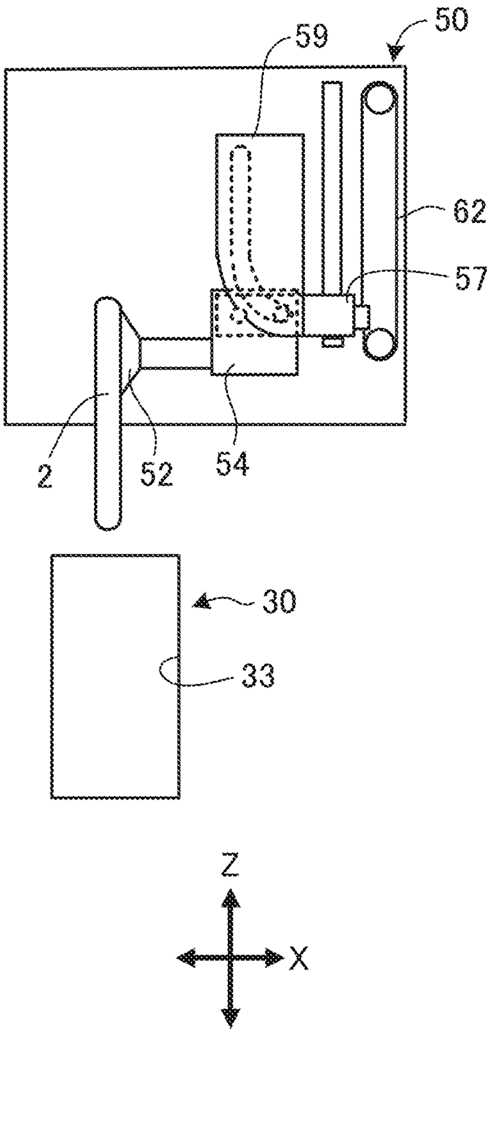
FIG. 9A and FIG. 9B are front views of the pickup unit illustrating the progression of the operation of the pickup unit subsequent to the progression illustrated in FIG. 8A, FIG. 8B, FIG. 8C, FIG. 8D, FIG. 8E, and FIG. 8F, according to an embodiment of the present disclosure.
Figure 9B:
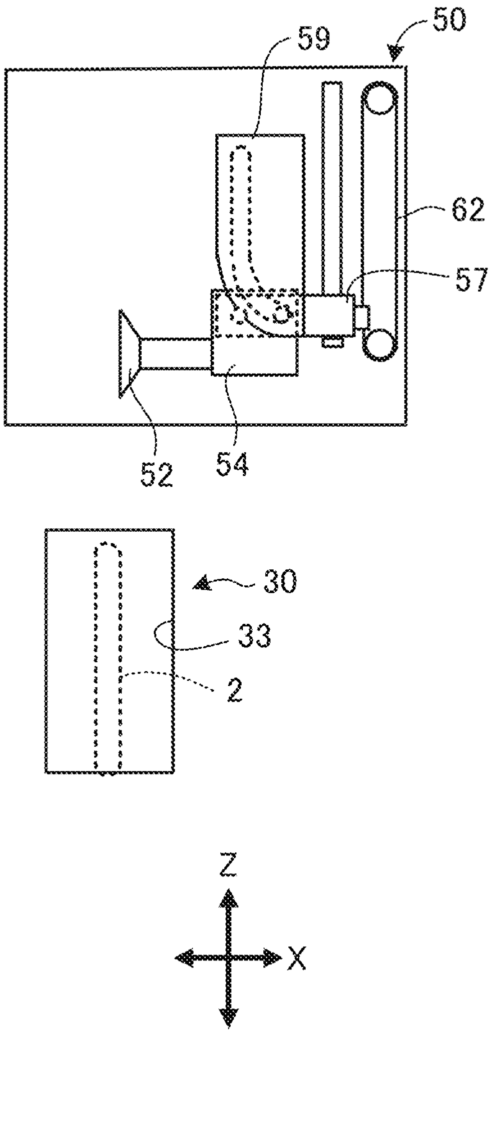

FIG. 9A and FIG. 9B are front views of the pickup unit 50 illustrating the progression of the operation of the pickup unit 50 subsequent to the progression illustrated in FIG. 8A, FIG. 8B, FIG. 8C, FIG. 8D, FIG. 8E, and FIG. 8F, according to the present embodiment.

For the sake of explanatory convenience, it is assumed in the present embodiment that, by the operation of the conveyance unit 90 illustrated in FIG. 1A and FIG. 1B, the pickup unit 50 is arranged between the multiple cartridges 10 of the drawer 21 arranged at the uppermost portion of the housing 199 in FIG. 1A and FIG. 1B and the multiple medicine dispensing trays 30 disposed directly below the multiple cartridges 10. In the present embodiment, it is assumed that the cartridges illustrated in FIG. 4A and FIG. 4B are used as the multiple cartridges 10. As illustrated in FIG. 8A, the pickup unit 50J is moved under one of the multiple cartridges 10 by the operation made by the conveyance unit 90 illustrated in FIG. 1A and FIG. 1B, and stops moving. Under such conditions, the suction device lifting and lowering motor 63 of the suction unit lifting and lowering unit is stopped, and the pair of suction pads 52 are positioned under the position of the top face of the pickup unit, which indicates the position of the top face of the picking-up frame 50*a* of the pickup unit 50 in a housing. Subsequently, as illustrated in FIG. 8B, the pair of suction pads 52 are moved upward by the operation of the suction device lifting and lowering motor 63, and enters from the pack pickup slot 17 between the right support portion 12 and the left support portion 13. Then, as soon as the pair of suction pads 52 contact one of the multiple medicine packages 2 at the bottom of one of the multiple cartridges 10, and the pair of suction pads 52 suck that medicine package 2. In so doing, the suction pump 48 as described above is driven to operate in advance so that the suctioning operation can be performed.

Subsequently, as illustrated in FIG. 8C, as the suction device lifting and lowering motor 63 is reversely operated, the pair of suction pads 52 move downward while sucking one of the multiple medicine packages 2 by the pair of suction pads 52, and the front end of one of the multiple medicine packages 2 is pulled out from one of the multiple cartridges 10. The front end of the medicine package indicates a side of the medicine package to be absorbed or sucked up by the pair of suction pads 52, and the same applies in the following description. The operation of pulling out the front end of one of the multiple medicine packages 2 from the pack pickup slot 17 of one of the multiple cartridges 10 under such conditions can be done without causing any sort of problem as the pulled-out medicine package 2 can deform freely.

Subsequently, as illustrated in FIG. 8D, by the operation of the conveyance unit 90 (see FIG. 1A and FIG. 1B), the pickup unit 50 is moved in the X-direction, which is the lateral direction, and the rear end of one of the multiple medicine packages 2 is drawn out or picked up from one of the multiple cartridges 10. Immediately after that, as illustrated in FIG. 8E and FIG. 8F, by the operation of the suction device lifting and lowering motor 63, one of the multiple medicine packages 2, which is approximately in a horizontal state and is sucked and held by the pair of suction pads 52, is rotated by substantially 90 degrees to change the posture to an approximately vertical or upright posture. In such rotational operation, the rotation axis 55 that is arranged on the suction-pad supporting member 54 moves along the guide groove 59*a* of the guide unit 59. Accordingly, the posture of one of the multiple medicine packages 2 can be changed from an approximately horizontal posture to an approximately vertical posture. The above series of operation in the above configuration may be achieved by a series of operation performed by a single suction device lifting and lowering motor 63.

Subsequently, as illustrated in FIG. 9A, once the pickup unit 50 that includes the pair of suction pads 52 and holds one of the multiple medicine packages 2 in a substantially vertical posture is carried by the conveyance unit 90 to a position substantially directly above the position where multiple medicine dispensing trays 30 are arranged, the operation of the above suction pump 48 is terminated. As a result, the suction holding of one of the multiple medicine packages 2 by the pair of suction pads 52 is released, and one of the multiple medicine packages 2 is inserted into one of the multiple partitions 33 that is a predetermined position in one of the multiple medicine dispensing trays 30 (see FIG. 9B).

After the above-described operation is performed a plurality of times and a desired one of the multiple medicine packages 2 is inserted into one of the multiple partitions 33 that is at a predetermined position of one of the multiple medicine dispensing trays 30, one of the multiple medicine dispensing trays 30 is ejected to the outside of the medication support device 200 through the third gate 43, and is received by a staff or the like in a day-care center or nursing home or a medication assistant.

As described above, the pickup unit 50 takes out the front end of the pack to a position under one of the multiple cartridges 10 in the process of picking up out one of the multiple medicine packages 2 from one of the multiple cartridges 10, and the conveyance unit 90 according to the present embodiment moves the pickup unit 50 so that the rear end of one of the multiple medicine packages 2 is picked up from one of the multiple cartridges 10 when the front end of one of the multiple medicine packages 2 has taken out to a position under one of the multiple cartridges 10. The moving direction of the pickup unit 50 by the conveyance unit 90 is set to the X-direction parallel to the lateral direction in which the rear end of one of the multiple medicine packages 2 is released from the support of the left support portion 13 and is drawn out from the pack pickup slot 17.

As described above, in the present control sample of the above embodiments of the present disclosure, when desired one of the multiple medicine packages 2 is picked up from one of the multiple cartridges 10, the pickup unit 50 is positioned or arranged under one of the multiple cartridges 10, and such desired one of the multiple medicine packages 2 is taken out in the downward direction of one of the multiple cartridges 10. When one of the multiple medicine packages 2 is taken out from the lower side of one of the multiple cartridges 10 as described above, the next one of the multiple medicine packages 2 automatically moves downward or toward the pack pickup slot 17 due to the self-weight of the movable board 16 and the multiple medicine packages 2 left in the cartridge 10. Due to such a configuration, the pickup unit 50 can perform the same operation with a relatively simple configuration regardless of the number of the multiple medicine packages 2 left in the cartridge 10.

The configuration and operation of the conveyance unit 90 is described below with reference to FIG. 10A and FIG. 10B.

Figure 10B:
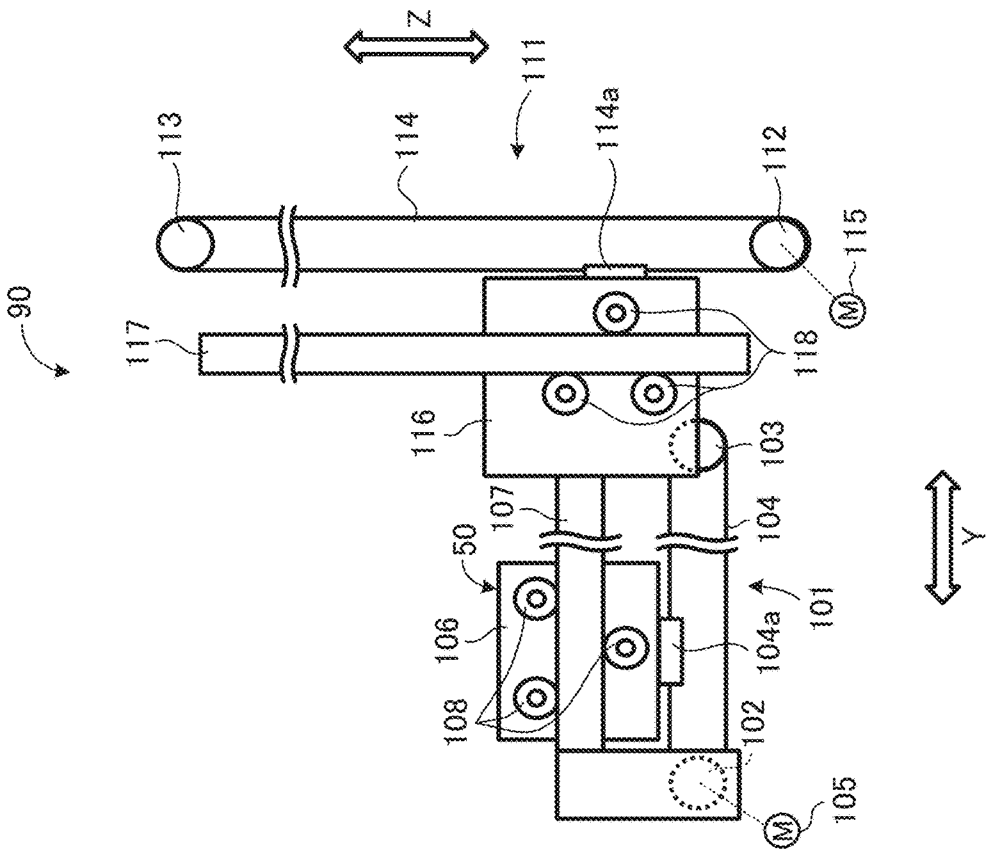
FIG. 10B is a side view of the conveyance unit illustrated in FIG. 10A, according to an embodiment of the present disclosure.
Figure 10A:
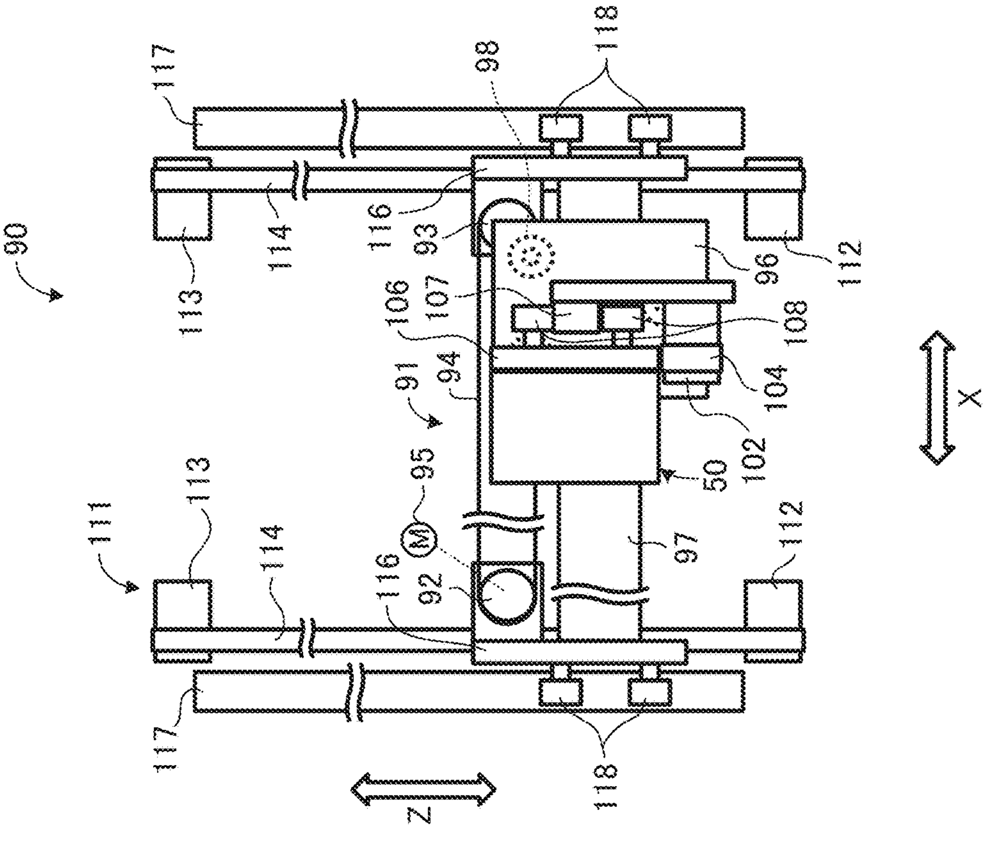
FIG. 10A is a front view of a conveyance unit illustrating a schematic configuration of the conveyance unit, according to an embodiment of the present disclosure.

FIG. 10A is a front view of the conveyance unit 90 illustrating a schematic configuration of the conveyance unit 90, according to the present embodiment.

FIG. 10B is a side view of the conveyance unit 90 illustrated in FIG. 10A, according to the present embodiment.

As in the configuration or structure of the medication support device 200 illustrated in FIG. 1A and FIG. 1B, the multiple cartridges 10 are aligned in a row on a pair of planes above and below the multiple medicine dispensing trays 30 in the Z-direction, the multiple medicine dispensing trays 30 are arranged above the multiple cartridges 10 on the lowermost one of the above pair of planes. In view of these circumstances, the pickup unit 50 is configured to move in three directions of the X-direction, the Y-direction, and the Z-direction. As described above, the conveyance unit 90 moves the pickup unit 50 in the X-direction, in the Y-direction, and in the Z-direction in order to convey one of the multiple medicine packages 2 picked up from one of the multiple cartridges 10 by the pickup unit 50 and pass it to one of the multiple medicine dispensing trays 30.

The pickup unit 50 is moved in the X-direction by an X-direction conveyance unit 91, and the pickup unit 50 is moved in the Y-direction by a Y-direction conveyance unit 101. The pickup unit 50 is moved in the Z-direction by a Z-direction conveyance unit 111. These three conveyance units have a similar configuration or structure.

The X-direction conveyance unit 91 according to the present embodiment includes a X-adaptor 96 attached to the pickup unit 50, a X-guide unit 97 that guides the pickup unit 50 in the X-direction through the X-adaptor 96, an endless belt 94 looped around a driving pulley 92 and a driven pulley 93, and a X-direction conveyance motor 95 coupled to the driving pulley 92 through a driving force conveyor such as a gear or a belt.

As illustrated in FIG. 10B, three rollers 98 are attached to the X-adaptor 96 so as to clamp the X-guide unit 97. Due to such a configuration, the X-adaptor 96 can roll over the X-guide unit 97. Note that, in FIG. 10A, two of the three rollers 98 are hidden by the pickup unit 50. The X-adaptor 96 is fixedly coupled to the endless belt 94 through a belt grip.

With the above-described configuration of the X-direction conveyance unit 91, as the X-direction conveyance motor 95 is driven, the driving force is conveyed to the endless belt 94 through the driving force conveyor and the driving pulley 92. Accordingly, the endless belt 94 rotates, and the pickup unit 50 moves in the X-direction parallel to the X-guide unit 97 together with the X-adaptor 96.

The Y-direction conveyance unit 101 according to the present embodiment includes a Y-adaptor 106 attached to the pickup unit 50, a Y-guide unit 107 that guides the pickup unit 50 in the Y-direction through the Y-adaptor 106, an endless belt 104 looped around a driving pulley 102 and a driven pulley 103, and a Y-direction conveyance motor 105 coupled to the driving pulley 102 through a driving force conveyor such as a gear or a belt.

As illustrated in FIG. 10B, three rollers 108 are attached to the Y-adaptor 106 so as to clamp the Y-guide unit 107. Due to such a configuration, the Y-adaptor 106 can roll over the Y-guide unit 107. The Y-adaptor 106 is coupled and fixed to the endless belt 104 through the belt grip 104*a*.

With the above-described configuration of the Y-direction conveyance unit 101, as the Y-direction conveyance motor 105 is driven, the driving force is conveyed to the endless belt 104 through the driving force conveyor and the driving pulley 102. Accordingly, the endless belt 104 rotates, and the pickup unit 50 moves in the Y-direction parallel to the Y-guide unit 107 together with the Y-adaptor 106.

The Z-direction conveyance unit 111 includes a pair of Z-adaptors 116 attached to both ends of the X-guide unit 97 in the X-direction, a pair of Z-guide units 117 that guide the pickup unit 50 in the Z-direction through the X-guide unit 97 and the pair of Z-adaptors 116, a pair of endless belts 114 each of which is looped around one of a pair of driving pulleys 112 and one of a pair of driven pulleys 113, and a Z-direction conveyance motor 115 coupled to the pair of driving pulleys 112 through a driving force conveyor such as a gear or a belt. In the Z-direction conveyance unit 111, the pair of driving pulleys 112, the pair of driven pulleys 113, and the pair of endless belts 114 are arranged on both sides in the X-direction, respectively. By contrast, the Z-direction conveyance motor 115 is provided for only on one of the pair of driving pulleys 112. As illustrated in FIG. 10B, three rollers 118 are attached to each one of the pair of Z-adaptors 116 so as to clamp corresponding one of the pair of Z-guide units 117. Due to such a configuration, the pair of Z-adaptors 116 can roll over the pair of Z-guide units 117, respectively. The pair of Z-adaptors 116 are coupled and fixed to the pair of endless belts 114 through a pair of belt grips 114*a*, respectively.

With the above-described configuration of the Z-direction conveyance unit 111, as the Z-direction conveyance motor 115 is driven, the driving force is conveyed to the pair of endless belts 114 through the driving force conveyor and the driving pulley 112. Accordingly, the pair of endless belts 114 rotates, and the pickup unit 50 moves in the Z-direction parallel to the Z-guide unit 117 together with the X-guide unit 97 and the Z-adaptor 116.

In FIG. 10A and FIG. 10B, the pickup unit 50 is configured to move in the triaxial directions including the X-axis direction, the Y-axis direction, and the Z-axis direction. However, no limitation is indicated thereby. For example, when the multiple cartridges 10 are arranged above the pickup unit 50 and the multiple medicine dispensing trays 30 are arranged below the pickup unit 50, the pickup unit 50 only needs to move in the X-direction and the Y-direction. In such cases, the number of axes of motion can be reduced by one.

Figure 11:
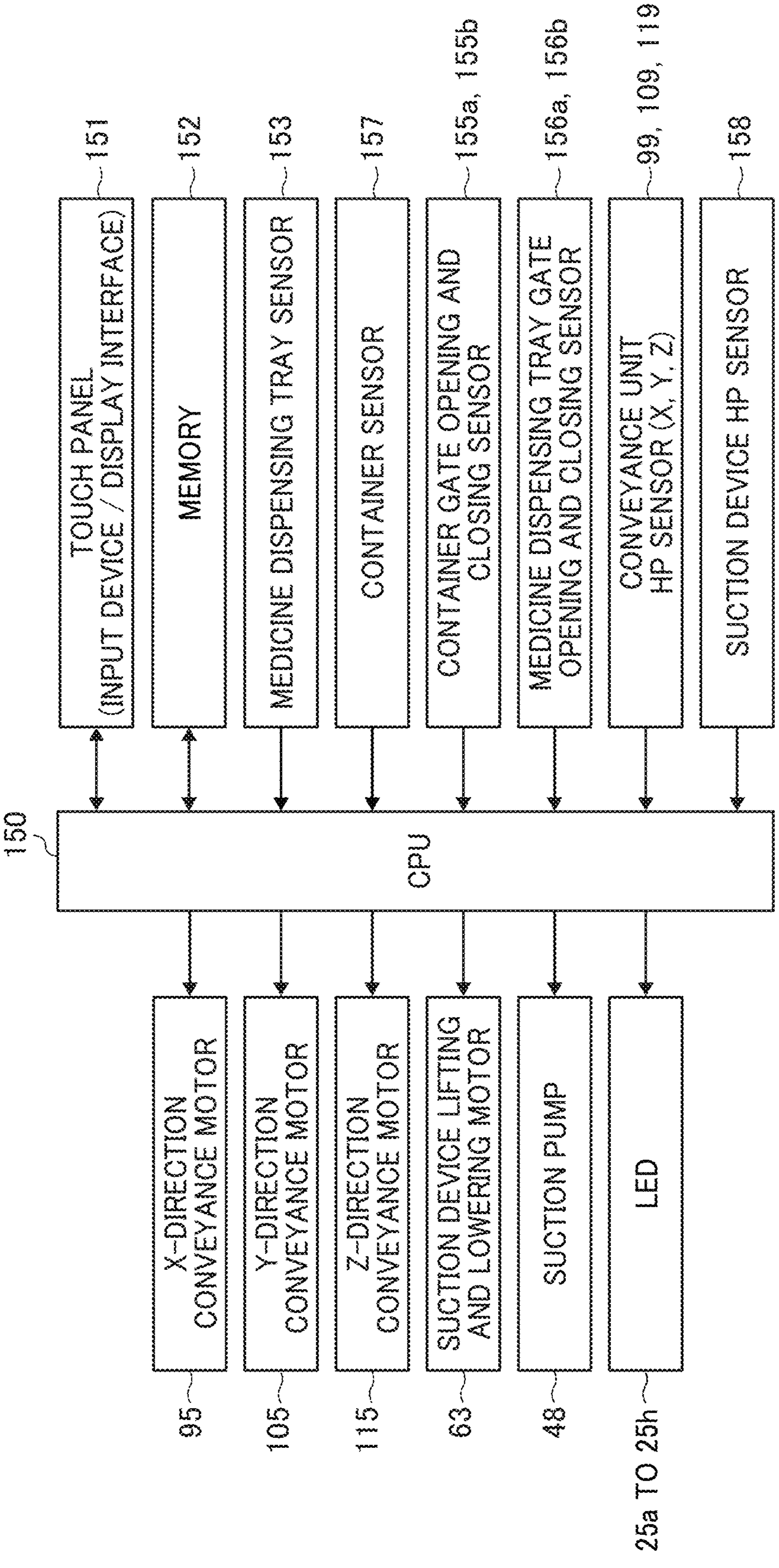
FIG. 11 is a control block diagram illustrating a schematic control structure for the medication support device illustrated in FIG. 1, according to an embodiment of the present disclosure.

FIG. 11 is a control block diagram illustrating a schematic control structure for the medication support device 200 according to the present embodiment.

As illustrated in FIG. 11, the medication support device 200 includes a central processing unit (CPU) that serves as a controller 150 that controls the operation of, for example, the components or elements of the medication support device 200. For example, the CPU may be provided with a built-in memory or a built-in timer. The CPU according to the present embodiment may provide notification to a staff or the like at a timing consistent with the program or may instruct the medication support device 200 to perform particular operation, based on various kinds of input such as the inputs from a sensor as will be described later in detail.

The CPU may have, for example, a computing or control function, and a timer or clocking function. A memory 152 includes, for example, a read-only memory (ROM), a random access memory (RAM), and an external memory. The ROM stores, for example, a program readable by the above CPU and various kinds of data in advance. Such a program stored in the ROM may be a program used in the flowchart of the controlling processes as will be described later in detail. The above various kinds of data may be, for example, the data about the relation between the multiple medicine packages 2 and the multiple partitions 33 of one of the multiple medicine dispensing trays 30 allocated to each of the patients who take medicines, the data about the relation between the multiple medicine packages 2 and the multiple partitions 33 of one of the multiple medicine dispensing trays 30 assigned to each one of the times of medication, or the data about the relation between the multiple medicine packages 2 and the multiple partitions 33 of one of the multiple medicine dispensing trays 30 sorted according to the order in which medicines are to be taken.

The CPU according to the present embodiment has an input and output (I/O) port, and a touch panel 151 that serves as a user interface (UI) is electrically connected to that input and output port of the CPU. However, no limitation is intended thereby, and the touch panel 151 may be, for example, a combination of an input device and a display interface that are arranged separately. For example, a combination of a keyboard and a light-emitting diode (LED) display may be used as the touch panel 151.

The CPU according to the present embodiment has an input port, and a medicine dispensing tray sensor 153 that detects the type of medicine dispensing tray 30 stored in the medication support device 200 or determines whether or not there is any medicine dispensing tray 30, a container sensor 157 that determines whether or not there is any cartridge 10, a container gate opening and closing sensor 155*a* and a container gate opening and closing sensor 155*b* that detect the opening and closing of the first gate 41 and the second gate 42, and a medicine dispensing tray gate opening and closing sensor 156*a* and a medicine dispensing tray gate opening and closing sensor 156*b* that detect the opening and closing of the third gate 43 and the fourth gate 44 are electrically connected to the output port of the CPU.

Moreover, to the input port of the CPU, a conveyance unit home position (HP) sensor 99 that detects the home position (HP) of the X-direction conveyance unit 91 in the pickup unit 50, a conveyance unit home position (HP) sensor 109 that detects the home position (HP) of the Y-direction conveyance unit 101 in the pickup unit 50, and a conveyance unit home position (HP) sensor 119 that detects the home position (HP) of the Z-direction conveyance unit 111 in the pickup unit 50 are electrically connected. Note that such a home position (HP) of each conveyance unit may be abbreviated to HP in the following description.

Further, to the input port of the CPU, a suction device home position (HP) sensor 158 that detects the home position (HP) of the suction pad 52 of the suction device 51 in the pickup unit 50 is electrically connected.

To the output port of the CPU, the LED 25*a*, the LED 25*b*, the LED 25*c*, the LED 25*d*, the LED 25*e*, the LED 25*f*, the LED 25*g*, and the LED 25*h* of the drawer 21, the suction pump 48, the suction device lifting and lowering motor 63, the X-direction conveyance motor 95 of the X-direction conveyance unit 91, the Y-direction conveyance motor 105 of the Y-direction conveyance unit 101, and the Z-direction conveyance motor 115 of the Z-direction conveyance unit 111 are electrically connected.

To the output port of the CPU, a notification unit may be electrically connected. Such a notification unit reports what sort of state or conditions the components or elements of the medication support device 200 are in by means of, for example, the light emitted from a light-emitting diode (LED) and the sound or vibration including voice. Moreover, such a notification unit may be provided with, for example, a loudspeaker or a light that indicates that the medicines are to be taken so that the staff or the like away from the medication support device 200 can be notified of such a time of medication.

Once the input data from the touch panel 151 and various kinds of signals from various types of sensors are input to the CPU, a command signal is newly output from the CPU. In other words, the CPU outputs a command signal used to control the audio device or the optical device of the display device of the touch panel 151 including the above notification unit, the LED 25*a*, the LED 25*b*, the LED 25*c*, the LED 25*d*, the LED 25*e*, the LED 25*f*, the LED 25*g*, and the LED 25*h*, the suction pumps 48, the suction device lifting and lowering motor 63, the X-direction conveyance motor 95, the Y-direction conveyance motor 105, and the Z-direction conveyance motor 115. The CPU according to the present embodiment has a function to execute the control operation as will be described later in detail in the following description or the flowchart of the controlling processes.

Figures 1, 2, 3, 4, 5, 6, 12A:
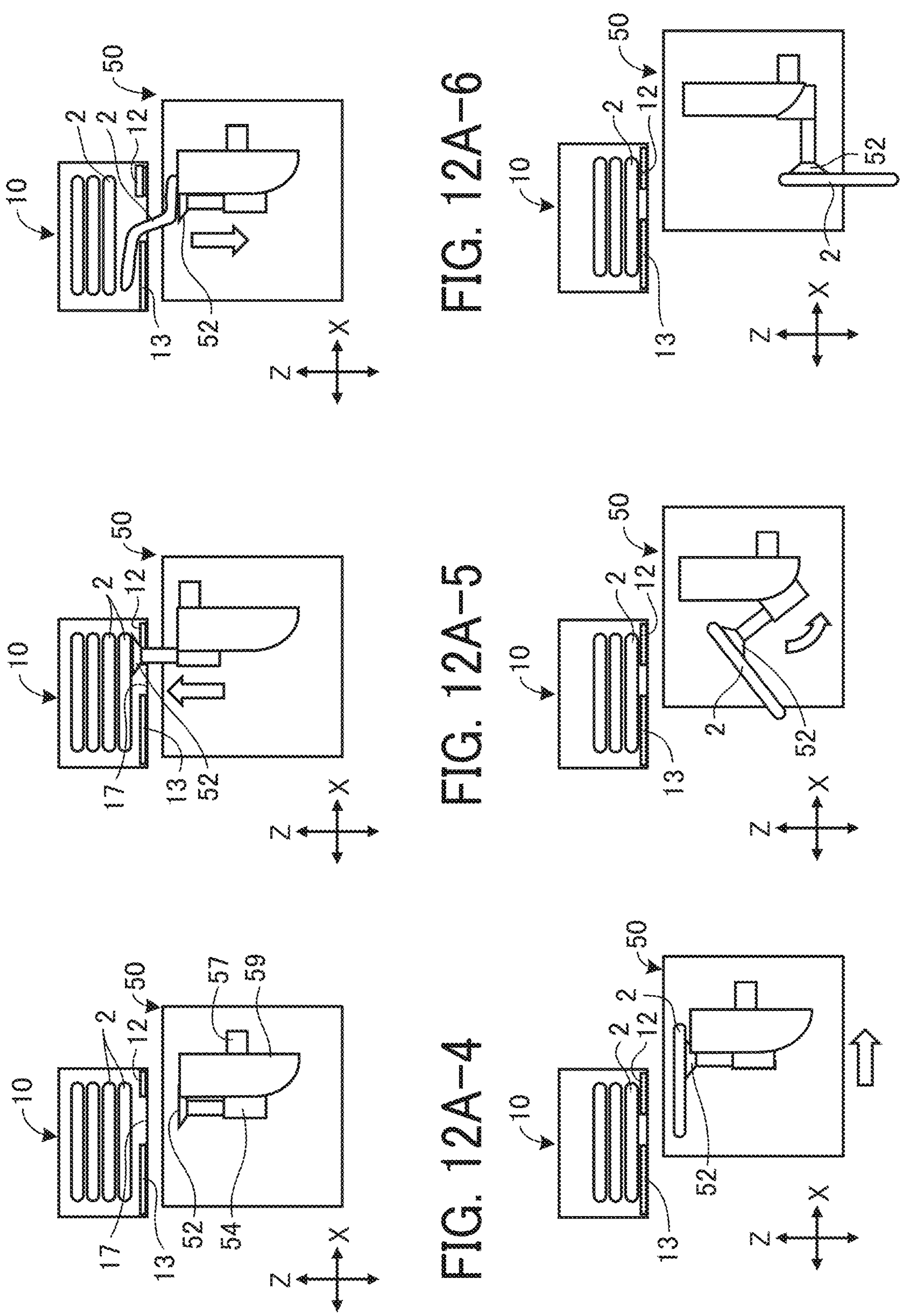

FIG. 12A-1, FIG. 12A-2, FIG. 12A-3, FIG. 12A-4, FIG. 12A-5, FIG. 12A-6, FIG. 12B, and FIG. 12C are schematic diagrams each illustrating an overall operation flow of the medication support device 200 illustrated in FIG. 1, according to the present embodiment. The above operation is executed based on the control commands sent from the CPU of the controller 150.

The operation that is described above with reference to FIG. 9A, FIG. 9B, FIG. 9C, FIG. 9D, FIG. 9E, and FIG. 9F is further described in detail with reference to FIG. 12A-1, FIG. 12A-2, FIG. 12A-3, FIG. 12A-4, FIG. 12A-5, and FIG. 12A-6. The operating status illustrated in FIG. 12A-6 illustrates a state in which the posture of the pair of suction pads 52 sucking and holding one of the multiple medicine packages 2 picked up from one of the multiple cartridges 10 is rotated by approximately 90 degrees. As illustrated in FIG. 12B, the medicine package 2 that has been taken out is held by the pair of suction pads 52 of the pickup unit 50 in the same posture as that illustrated in FIG. 12A-6.

As illustrated in FIG. 12B, the pickup unit 50 that includes the pair of suction pads 52 and holds one of the multiple medicine packages 2 is conveyed by the conveyance unit 90 along the route indicated by thick broken lines to the medicine dispending position 29 where multiple medicine dispensing trays 30 are arranged. When the pickup unit 50 is carried to a position substantially directly above the multiple medicine dispensing trays 30 at the medicine dispending position 29, the operation of the suction pump 48 is terminated. As a result, the suction holding of one of the multiple medicine packages 2 by the pair of suction pads 52 is released, and one of the multiple medicine packages 2 is inserted into the predetermined partition 33 of the multiple medicine dispensing trays 30.

Figure 12C:
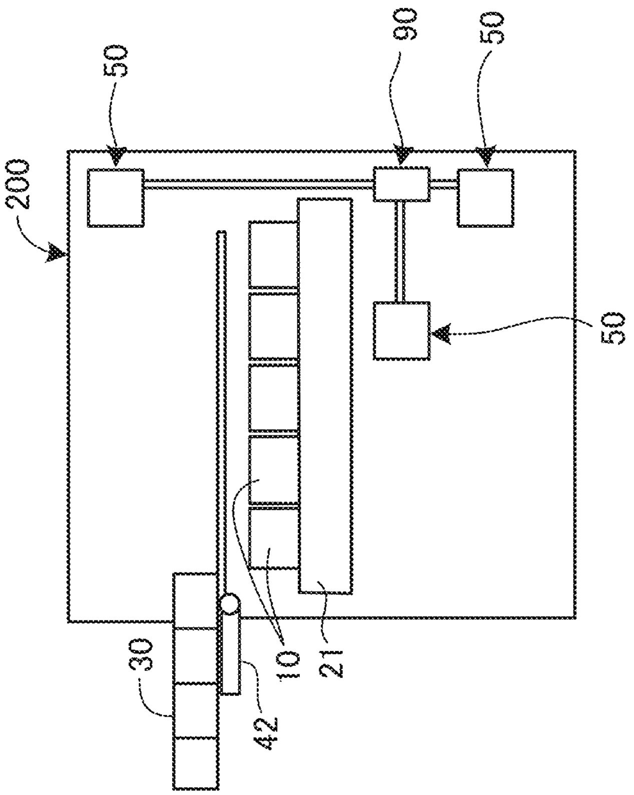
Figure 12B:
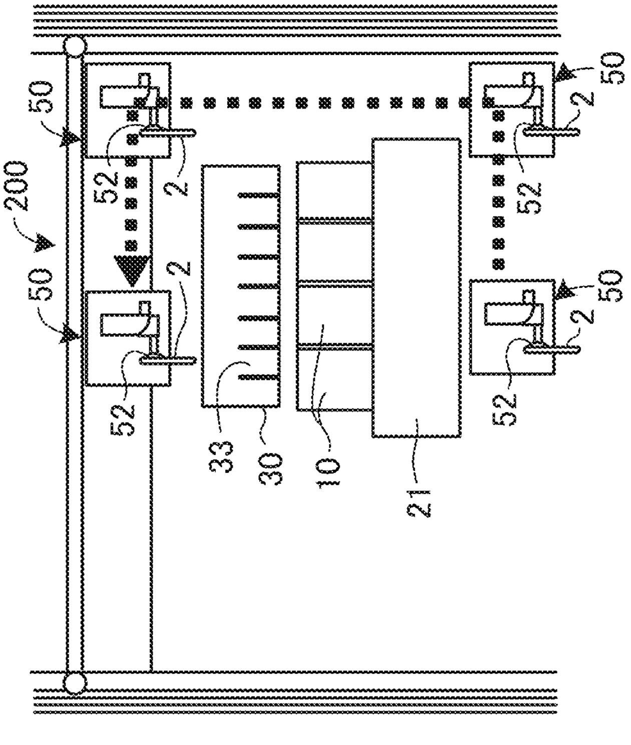

After the above-described operation is performed a plurality of times and a desired one of the multiple medicine packages 2 is inserted into one of the multiple partitions 33 that is at a predetermined position of one of the multiple medicine dispensing trays 30, as illustrated in FIG. 12C, one of the multiple medicine dispensing trays 30 is ejected to the outside of the medication support device 200 through, for example, the second gate 42, and is received by a staff or the like in a day-care center or nursing home or a medication assistant.

Figure 13:
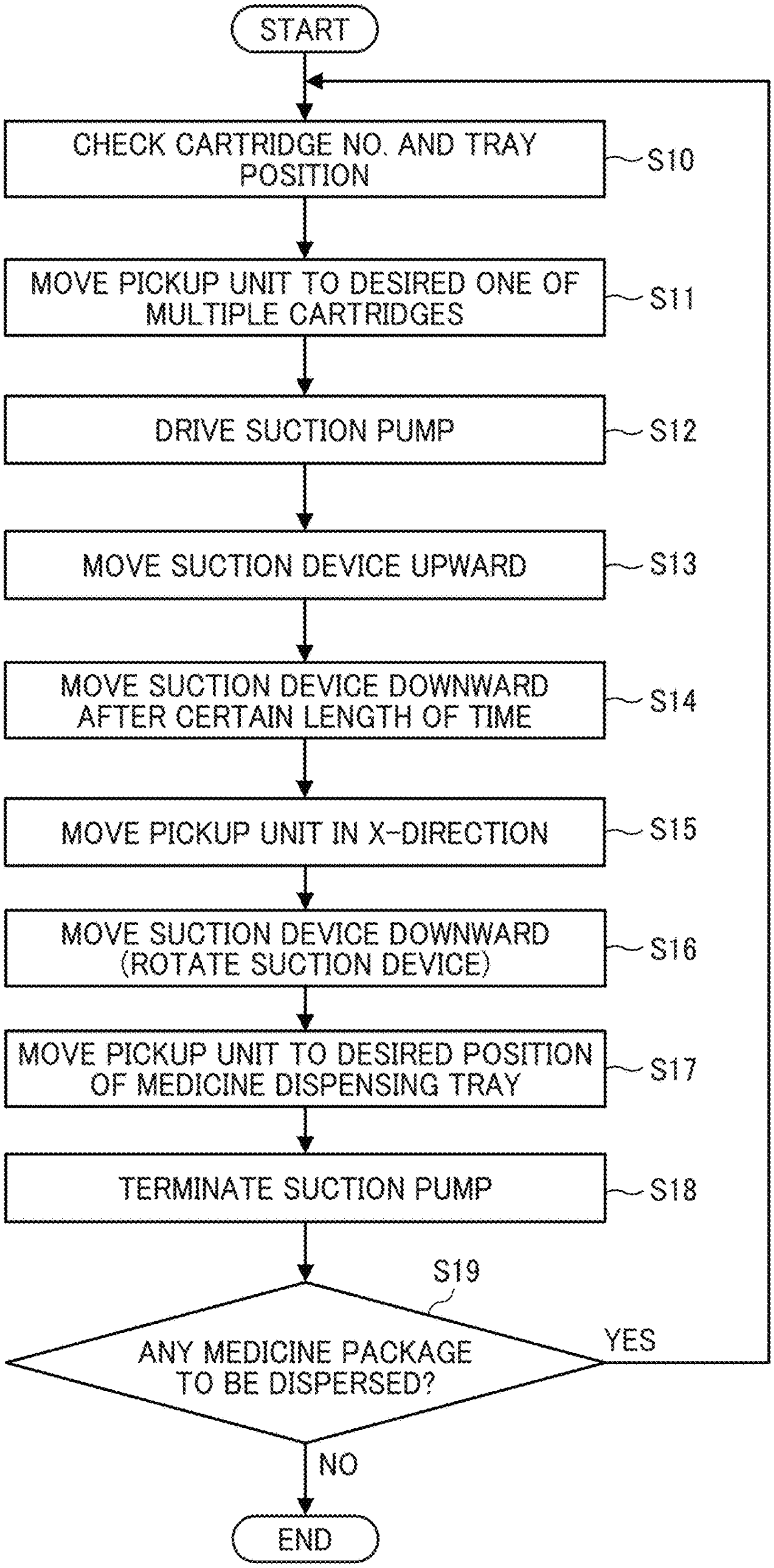
FIG. 13 is a flowchart of the operation flow of a pickup unit according to an embodiment of the present disclosure.

With reference to FIG. 13, supplemental description is given for the operation flow of the pickup unit 50 in an overall operation flow of FIG. 12A-1, FIG. 12A-2, FIG. 12A-3, FIG. 12A-4, FIG. 12A-5, FIG. 12A-6, FIG. 12B, and FIG. 12C.

FIG. 13 is a flowchart of the operation flow of the pickup unit 50 according to the present embodiment.

Firstly, in a step S10 of FIG. 13, the number (No.) given to desired one of the multiple cartridges 10 that stores the medicine package 2 to be dispersed is checked, and a desired position of the medicine dispensing tray 30 to which the medicine package 2 is passed is checked.

Subsequently, in a step S11, the pickup unit 50 is moved to desired one of the multiple cartridges 10 by the conveyance operation of the conveyance unit 90. Then, in a step S12, the suction device lifting and lowering motor 63 is driven to rotate while the suction pump 48 is being driven. By so doing, in a step S13, the suction device 51 is moved upward. After a certain length of time has passed after the lowermost one of the multiple medicine packages 2 in one of the multiple cartridges 10 is sucked and held by the pair of suction pads 52, in a step S14, the suction device lifting and lowering motor 63 is driven to rotate in the reverse direction. By so doing, the suction device 51 is moved downward. Subsequently, in a step S15, the pickup unit 50 is moved in the X-direction, and desired one of the multiple medicine packages 2 is completely taken out from one of the multiple cartridges 10. Then, in a step S16, the suction device lifting and lowering motor 63 is further driven to rotate in the reverse direction so as to move the suction device 51 downward. As a result, the suction device 51 is rotated by approximately 90 degrees, and the posture of the medicine package 2 is changed from an approximately parallel or horizontal posture to an approximately vertical posture.

Subsequently, in a step S17, the pickup unit 50 is moved to a desired position of one of the multiple medicine dispensing trays 30 by the convey operation of the conveyance unit 90. When the pickup unit 50 has moved to the position of desired one of the multiple medicine dispensing trays 30, in a step S18, the operation of the suction pump 48 is terminated, and the medicine package 2 is released and separated from the pair of suction pads 52. Then, in a step S19, whether there is any medicine package 2 to be dispersed is checked. When there is no medicine package 2 to be dispersed, a series of operation flow is terminated. On the other hand, when it is determined in the step S19 that there is at least one medicine package 2 to be dispersed, the process is returned to the step S10, and the same series of processes in the above steps are repeated.

In the above control sample of the above embodiments of the present disclosure, when desired one of the multiple medicine packages 2 is picked up from one of the multiple cartridges 10, the pickup unit 50 is positioned under one of the multiple cartridges 10, and such desired one of the multiple medicine packages 2 is taken out in the downward direction of one of the multiple cartridges 10. When one of the multiple medicine packages 2 is taken out from the lower side of one of the multiple cartridges as described above, the next one of the multiple medicine packages 2 automatically moves downward or toward the pack pickup slot 17 due to the self-weight of the movable board 16 and the multiple medicine packages 2 left in the cartridge 10. Due to such a configuration, the pickup unit 50 can perform the same operation with a relatively simple configuration regardless of the number of the multiple medicine packages 2 left in the cartridge 10.

According to the above control sample of the above embodiments of the present disclosure, a medication support device can be provided with a relatively simple configuration in which the multiple medicine packs can securely be stored in the multiple containers and those medicine packs can smoothly be picked up on a one-by-one basis with stability when the multiple medicine packs are to be taken out from one of the containers.

More specifically, a medication support device can be provided in which the multiple medicine packs can be held in the container and those medicine packs can easily be taken out and do not fall off easily. Moreover, a medication support device can be provided in which the next one of the multiple medicine packs to be picked up by the pickup device can be prevented from falling off and the posture of the multiple medicine packs do not turn bad when those medicine packs are supported.

However, it is learned through the experiment or examination that the above-described configuration or structure according to the control sample of the embodiments of the present disclosure involves some issues. Such issues due to the configuration or structure according to the control sample of the embodiments of the present disclosure are described below.

In view of, for example, day-care center or nursing home where typically a large number of people reside, medicine dispensing trays that are provided with a plurality of partitions such that a plurality of packs for multiple persons can be taken out at a time have been proposed. However, if a plurality of packs are horizontally placed in each one of the multiple partitions of each one of the multiple medicine dispensing trays or if the multiple medicine packages are placed such that the thickness direction of those medicine packages are substantially vertical, the medication support device that includes the multiple medicine dispensing tray tends to increase in size. In order to deal with such a situation, a plurality of packs need to be vertically placed in each one of the multiple narrow partitions of each one of the multiple medicine dispensing trays suited for a plurality of persons or the multiple medicine packages need to be placed such that the thickness direction of those medicine packages are substantially horizontal. The issues that are caused by such circumstances are described below.

As illustrated in FIG. 9A, immediately before one of the multiple medicine packages 2 is inserted into one of the multiple medicine dispensing trays 30, such one of the multiple medicine packages 2 is sucked by the pair of suction pads 52 of the pickup unit 50 and held in the vertical direction. When the pickup unit 50 that is held in the vertical posture is carried by the conveyance unit 90 to a position substantially directly above the position where multiple medicine dispensing trays 30 are arranged, the operation of the above suction pump 48 is terminated. As a result, the suction holding of one of the multiple medicine packages 2 by the pair of suction pads 52 is released, and such one of the multiple medicine packages 2 is dropped and vertically inserted into a predetermined narrow one of the multiple partitions 33 of one of the multiple medicine dispensing trays 30 placed underneath.

In the pickup unit 50 that includes the pair of suction pads 52, when the suction holding of one of the multiple medicine packages 2 by the pair of suction pads 52 is to be released, so-called vacuum breakdown in which negative pressure is changed to atmospheric pressure is performed by ejecting a small amount of air using the above suction pump 48 that serves as an air supply unit. If the pressure of vacuum breakdown under such circumstances is strong, one of the multiple medicine packages 2 is unintentionally blown off and cannot be placed in a predetermined one of the multiple partitions 33. On the contrary, if the pressure of vacuum breakdown under such circumstances is weak, one of the multiple medicine packages 2, which is light in weight, unintentionally sticks to the pair of suction pads 52 due to static electricity. In either case, each one of the multiple medicine packages 2 does not orderly drop and fall into the predetermined one of the multiple partitions 33 of one of the multiple medicine dispensing trays 30 with reliability.

First Example

A separator 64 according to an embodiment of the present disclosure provided for a pickup unit 50A of the medication support device 200 is described below with reference to FIG. 14A, FIG. 14B, FIG. 15, and FIG. 16. For the sake of explanatory convenience, the present embodiment that is described with reference to FIG. 14A, FIG. 14B, FIG. 15, and FIG. 16 will be referred to as the first embodiment of the present disclosure.

Figure 14B:
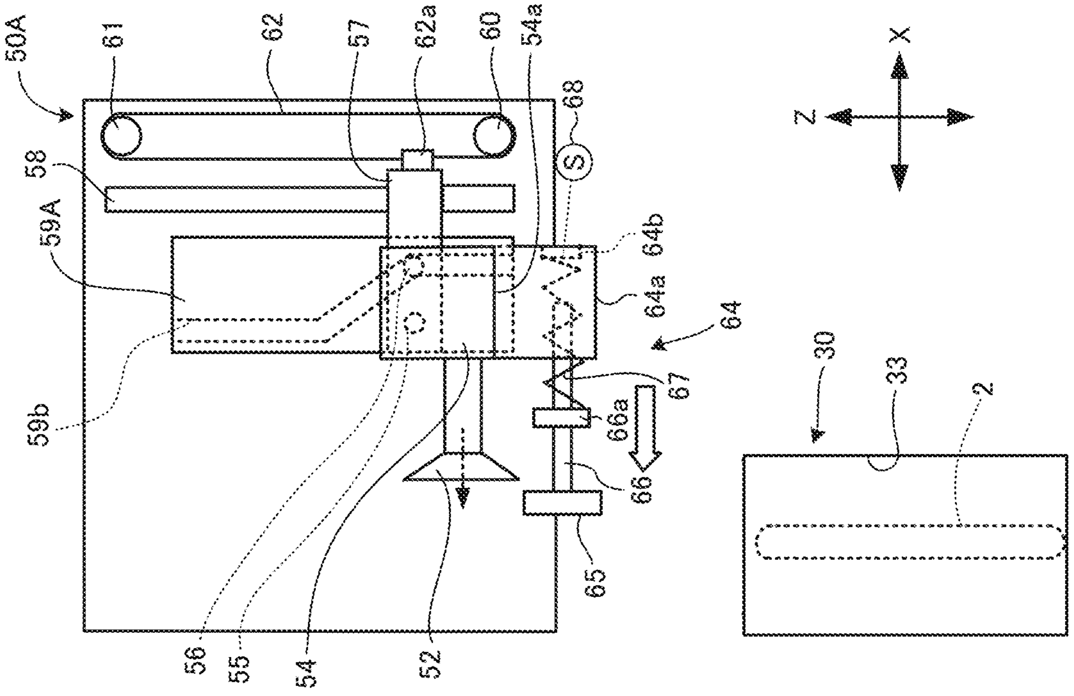
FIG. 14A and FIG. 14B are front views of a separator provided for a pickup unit and illustrate the structure or operation of the separator, according to the first embodiment of the present disclosure.
Figure 14A:
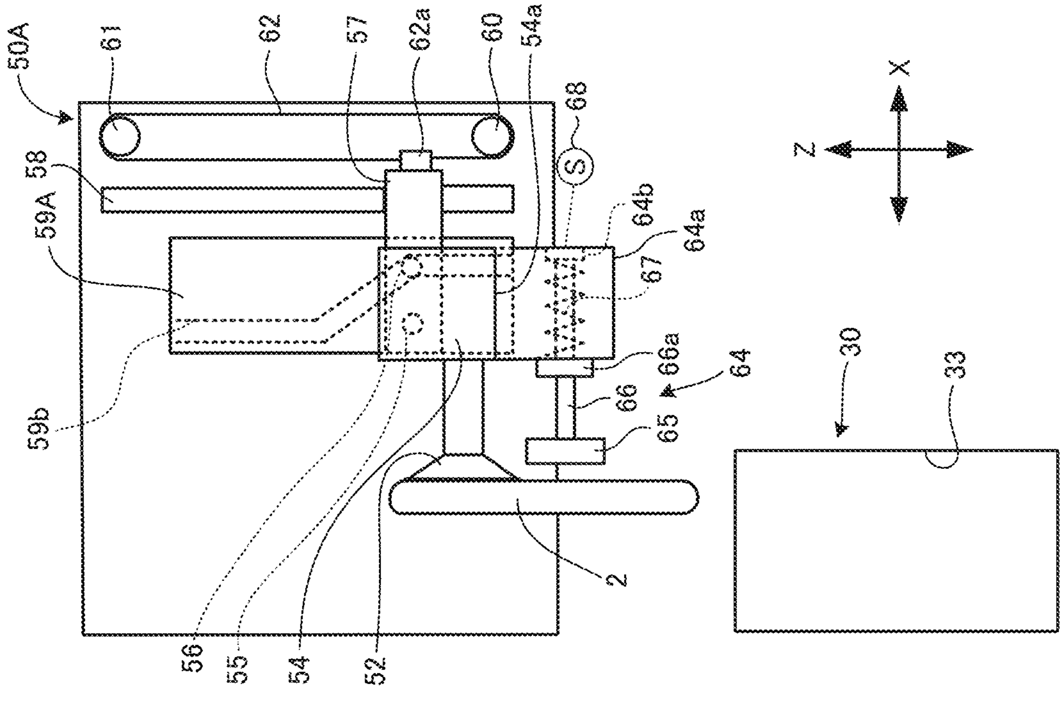

FIG. 14A and FIG. 14B are front views of the separator 64 provided for the pickup unit 50A and illustrate the structure or operation of the separator 64, according to the first embodiment of the present disclosure.

Figure 15:
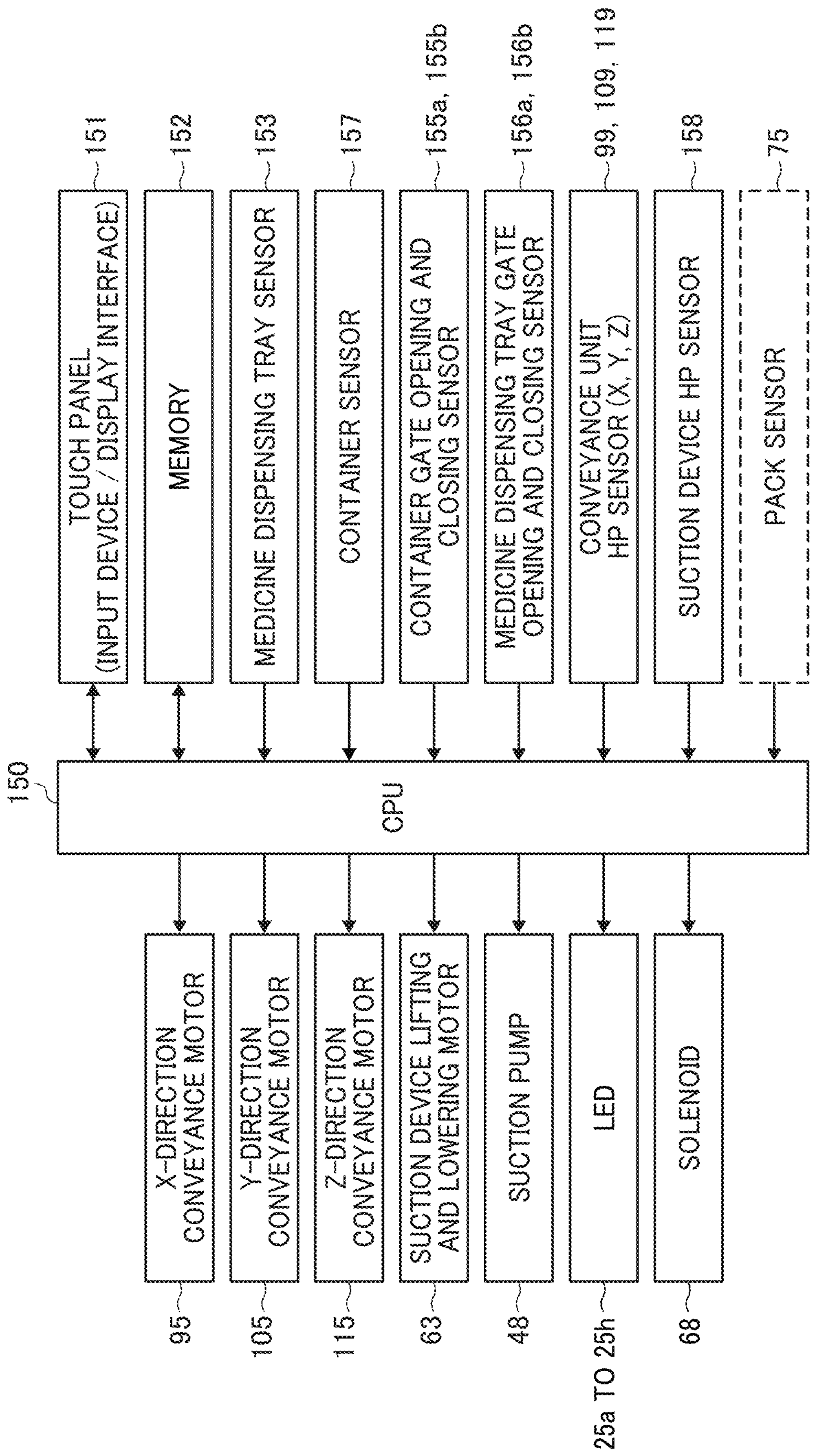
FIG. 15 is a control block diagram illustrating a schematic control structure for the medication support device illustrated in FIG. 14A and FIG. 14B, according to an embodiment of the present disclosure.

FIG. 15 is a control block diagram illustrating a schematic control structure for the medication support device 200 according to the first example of the present disclosure.

Figure 16:
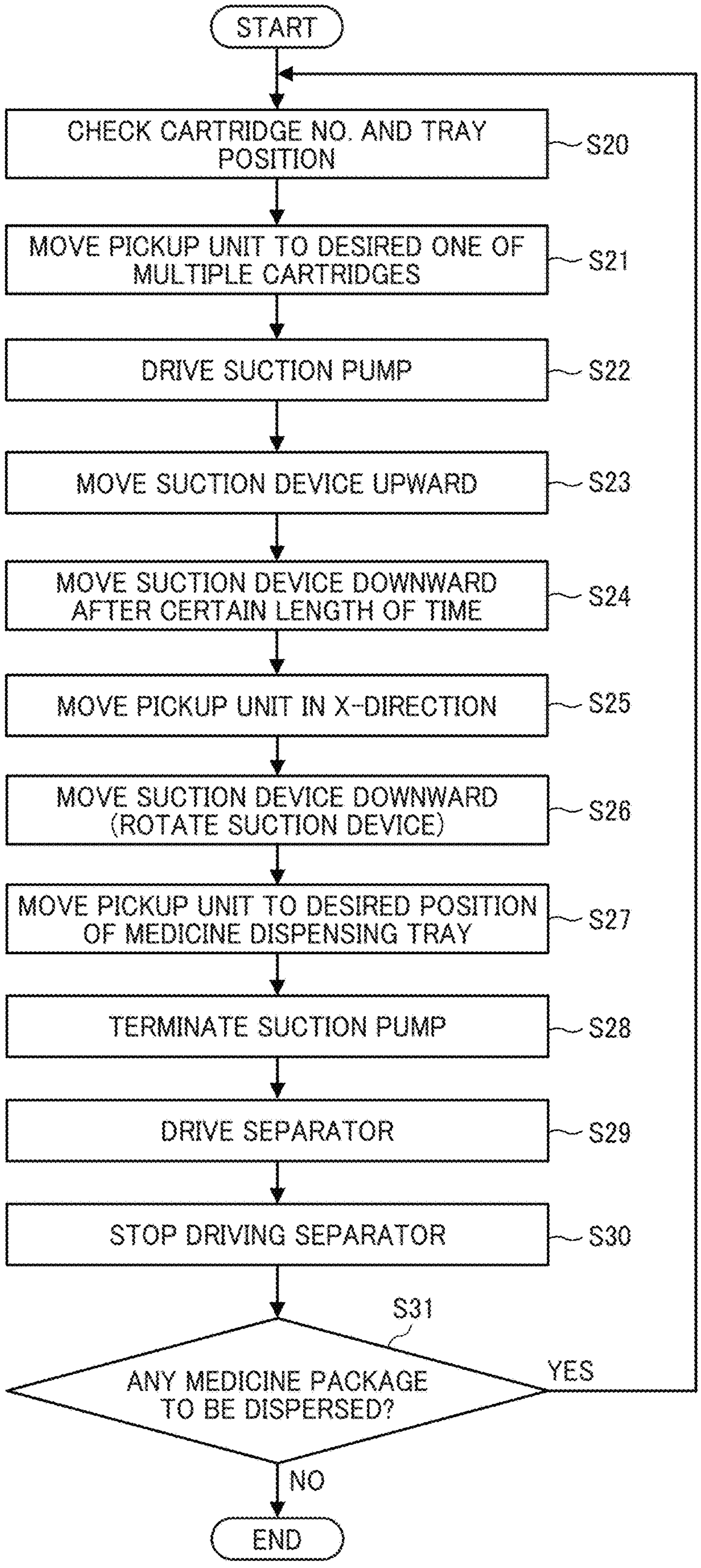
FIG. 16 is a flowchart of the operation flow of the pickup unit illustrated in FIG. 14A and FIG. 14B, according to an embodiment of the present disclosure.

FIG. 16 is a flowchart of the operation flow of the pickup unit 50 illustrated in FIG. 14A and FIG. 14B, according to the present embodiment.

Typically, the medication support device 200 according to the first embodiment of the present disclosure is different from the pickup unit 50 according to the control sample of the above embodiments of the present disclosure described above with reference to FIG. 1A to FIG. 13 in that the pickup unit 50A in which the structure and operation of the pickup unit 50 is changed is adopted. The other configurations or operations of the present embodiment are similar to the medication support device 200 according to the control sample of the embodiments of the present disclosure described as above with reference to FIG. 1A to FIG. 13.

Typically, the pickup unit 50A according to the first embodiment of the present disclosure is different from the pickup unit 50 according to the control sample of the above embodiments of the present disclosure described as above with reference to, for example, FIG. 7A, FIG. 7B, FIG. 8A, FIG. 8B, FIG. 8C, FIG. 8D, FIG. 8E, and FIG. 8F in that the separator 64 is newly formed and the guide groove 59*a* of the guide unit 59 provided for the pickup unit 50 are replaced with a guide unit 59A whose external shape is altered and a guide groove 59*b* whose forming area is changed.

The guide unit 59A has a rectangular parallelepiped shape that extends longer in the up-and-down directions than the guide unit 59.

The guide groove 59*b* having a specific shape includes the first guide groove portion that extends in the Z-direction with relatively great length so as to hold the posture of the pair of suction pads 52 upward as indicated by solid lines in FIG. 7A through the suction-pad supporting member 54 in a substantially horizontal state as guided by the guide axis 56. The guide groove 59*b* includes the second guide groove portion that gently and loosely inclines to the right side as it goes downward to rotate the posture of the suction-pad supporting member 54 and the pair of suction pads 52 by approximately 90 degrees, and the third guide groove portion that extends in the Z-direction with relatively great length as it goes downward. The first guide groove portion and the second guide groove portion communicate with each other and are coupled to each other. The guide groove 59*b* according to the present embodiment is formed over a wide range in the up-and-down directions compared with the guide groove 59*a* of the pickup unit 50 according to the control sample of the embodiments of the present disclosure, and is roughly shaped like "S." As described above, the inflected portion of the guide groove 59*b* are more or less schematically illustrated compared with the inflected portion of the guide groove 59*a*, but the functionality of the guide groove 59*b* is equivalent to the functionality of the guide groove 59*a*. The second guide groove portion and the third guide groove portion of the guide groove 59*b* are used to achieve a configuration without an extra driving source in an embodiment described later.

The posture changing unit in the pickup unit 50A may include, for example, a suction-pad supporting member 54 coupled to a suction device base 57 through a rotation axis 55, a guide unit 59A formed with a guide groove 59*a* having a specific shape, a guide axis 56 that is consistently fitted into the guide groove 59*b* to guide the suction-pad supporting member 54, and the above suction unit lifting and lowering unit. Due to the relation between the cross-axis distance between the guide axis 56 and the rotation axis 55 and the shape of the guide groove 59*b*, the pair of suction pads 52 according to the first embodiment of the present disclosure can move around the rotation axis 55, which serves as a fulcrum, to take various kinds of posture or attitude in a wide range in a similar manner to the pair of suction pads 52 according to the control sample of the embodiments of the present disclosure.

FIG. 14A illustrates the pickup unit 50A and the multiple medicine dispensing trays 30 in which one of the multiple medicine packages 2 picked up from one of the multiple cartridges 10 is held by the pickup unit 50A and is carried to a position above the one of the multiple medicine dispensing trays 30. As illustrated in FIG. 14A, in the pickup unit 50A according to the first embodiment of the present disclosure, one of the multiple medicine packages 2 is sucked by the suction pads 52 and held in the vertical direction. In other words, as illustrated in FIG. 14A, in the pickup unit 50A according to the first embodiment of the present disclosure, one of the multiple medicine packages 2 is kept such that the thickness direction of that medicine package 2 is substantially horizontal. The separator 64 according to the present embodiment is arranged close to the pair of suction pads 52, and serves as a separator that makes one of the multiple medicine packages 2 picked up from one of the multiple cartridges 10 separate from the pair of suction pads 52 of the pickup unit 50A. In the first embodiment of the present disclosure, the separator 64 is fixed to the coupler 54*a* of the suction-pad supporting member 54 and works or operates together with the above posture-changing operation of the suction-pad supporting member 54.

The separator 64 according to the present embodiment includes a separating head 65, a plunger 66 fixed to the separating head 65, a spring loaded portion 66*a* fixed to the plunger 66, a spring 67, a housing 64*a* that stores the plunger 66 and the spring 67, a spring loaded portion 64*b* fixed to the inner surface of the housing 64*a*, and a solenoid 68 (see FIG. 15) used as a driving source that drives the separating head 65 and the plunger 66 to move linearly.

The housing 64*a* of the separator 64 is fixed to the coupler 54*a* of the suction-pad supporting member 54. Accordingly, the separator 64 works or operates together with the vertical movement and the swing movement of the suction-pad supporting member 54.

The separating head 65 according to the present embodiment serves as a separating member of a separator, and forces one of the multiple medicine packages 2 to be separate from the pair of suction pads 52 that vertically sucks and holds one of the multiple medicine packages 2 picked up from one of the multiple cartridges 10. The spring 67 is, for example, a pulling spring arranged between the spring loaded portion 66*a* and the spring loaded portion 64*b*, and biases the spring loaded portion 66*a* so as to be pulled in a right direction as illustrated in FIG. 14A when the solenoid 68 is not supplied with electric power and the power of the solenoid is turned off. Accordingly, the spring loaded portion 66*a* is consistently in pressure contact with the housing 64*a*.

As described above, a pushing type in which a spring is used is adopted as the solenoid 68. However, no limitation is indicated thereby, and a pulling type or a pushing and pulling type may be adopted. The driving source is not limited to the solenoid 68, but may be a motor or other kinds of actuator. Alternatively, several kinds of driving sources may be used in combination where appropriate depending on the configuration or structure.

In place of the spring 67 that is a pulling spring, for example, a compression spring arranged between the separating head 65 and the spring loaded portion 66*a* may be used. In such cases, the spring loaded portion 66*a* is not fixed to the plunger 66 but is arranged so as to move freely independently of the plunger 66.

Typically, the control structure for the medication support device 200 according to the first embodiment of the present disclosure described above with reference to FIG. is different from the medication support device 200 according to the control sample of the above embodiments of the present disclosure described as above with reference to FIG. 11 in that the solenoid 68 is newly formed. A pack sensor 75 that is indicated by dotted lines in FIG. 15 is not adopted in the present embodiment but is to be used in the third embodiment of the present disclosure as will be described later in detail.

The operation of the medication support device 200 according to the first embodiment is described below with reference to FIG. 14A, FIG. 14B, and FIG. 16. The steps S20 to S28 of the operation flow of the pickup unit 50A according to the first embodiment of the present disclosure described with reference to FIG. 16 are equivalent to the steps S1 to S18 of the operation flow of the pickup unit 50 according to the control sample of the embodiments of the present disclosure described as above with reference to FIG. 13.

As described above and illustrated in FIG. 14A, according to the first embodiment of the present disclosure, one of the multiple medicine packages 2 is to be placed in a predetermined one of the multiple partitions 33 of one of the multiple medicine dispensing trays 30. However, in so doing, an undesired result may occur. In particular, there are some cases in which the target one of the multiple medicine packages 2 does not fall off from the pair of suction pads 52 due to an extremely curled portion at an end of one of the multiple medicine packages 2. For example, such an undesired result occur as one of the multiple medicine packages 2 is caught by the pair of suction pads 52 or a member arranged nearby or one of the multiple medicine packages 2 is stuck due to the static electricity caused at the holding portion of the pair of suction pads 52.

In the first embodiment of the present disclosure, the operation as illustrated in FIG. 14B is performed when one of the multiple medicine packages 2 is sucked and held vertically by the pair of suction pads 52 as illustrated in FIG. 14A. The steps S20 to S28 of the operation flow of the pickup unit 50A according to the first embodiment of the present disclosure described with reference to FIG. 16 are equivalent to the steps S10 to S18 of the operation flow of the pickup unit 50 of the medication support device 200 according to the control sample of the embodiments of the present disclosure described as above with reference to FIG. 13.

More specifically, after the suction pump 48 is stopped in the step S28 of FIG. 16, the operation of the separator 64 is started in a step S29. In other words, once electric power is supplied to the solenoid 68 to turn on the solenoid 68, as illustrated in FIG. 14B, the separating head 65 and the plunger 66 move against the pressing force caused by the spring 67 so as to protrude in the direction as indicated by a large hollow arrow, and cause pressing force such that one of the multiple medicine packages 2 that is caught or stuck to the pair of suction pads 52 is forced to be taken off.

Due to such configurations as described above, one of the multiple medicine packages 2 sucked and held in the vertical orientation by the pair of suction pads 52 is forced to be taken off, and is orderly stored in a predetermined one of the multiple partitions 33 of one of the multiple medicine dispensing trays 30 as indicated by dotted lines.

Subsequently, the solenoid 68 is turned off to stop the operation of the separator 64 (see the step S30). Then, in a step S31, whether there is any medicine package 2 to be dispersed is checked. When there is no medicine package 2 to be dispersed, a series of operation flow is terminated. On the other hand, when it is determined in the step S31 that there is at least one medicine package 2 to be dispersed, the process is returned to the step S20, and the same series of processes in the above steps are repeated.

In the first embodiment of the present disclosure, the separating head 65 is configured to work or operate together with the posture changing operation of the pair of suction pads 52. However, no limitation is intended thereby, and the separating head 65 may be arranged in an immovable state close to the pair of suction pads 52 that have changed their posture or attitude to suck and hold one of the multiple medicine packages 2 vertically, so as not to interfere with, for example, other elements or movable parts. The separating head 65 may be configured so as to operate together with the up-and-down movement of the suction device base 57.

According to the first embodiment of the present disclosure, the state in which the pack is caught by or stuck to the pair of suction pads 52 can be released, and the target one of the multiple medicine packages 2 can orderly be dropped into a predetermined one of the multiple partitions 33 of one of the multiple medicine dispensing trays 30 with reliability. In other words, regardless of the intensity of pressure of vacuum breakdown, one of the multiple medicine packages 2 that is caught by or stuck to, for example, the pair of suction pads 52 of the pickup unit 50A can be made separate from, for example, the pair of suction pads 52 without causing a failure of dropping the medicine pack, and can be dispensed into one of the multiple medicine dispensing trays 30 with reliability.

Second Example

The second embodiment of the present embodiment that is different from the first embodiment of the present disclosure is described below with reference to FIG. 17.

Figure 17:
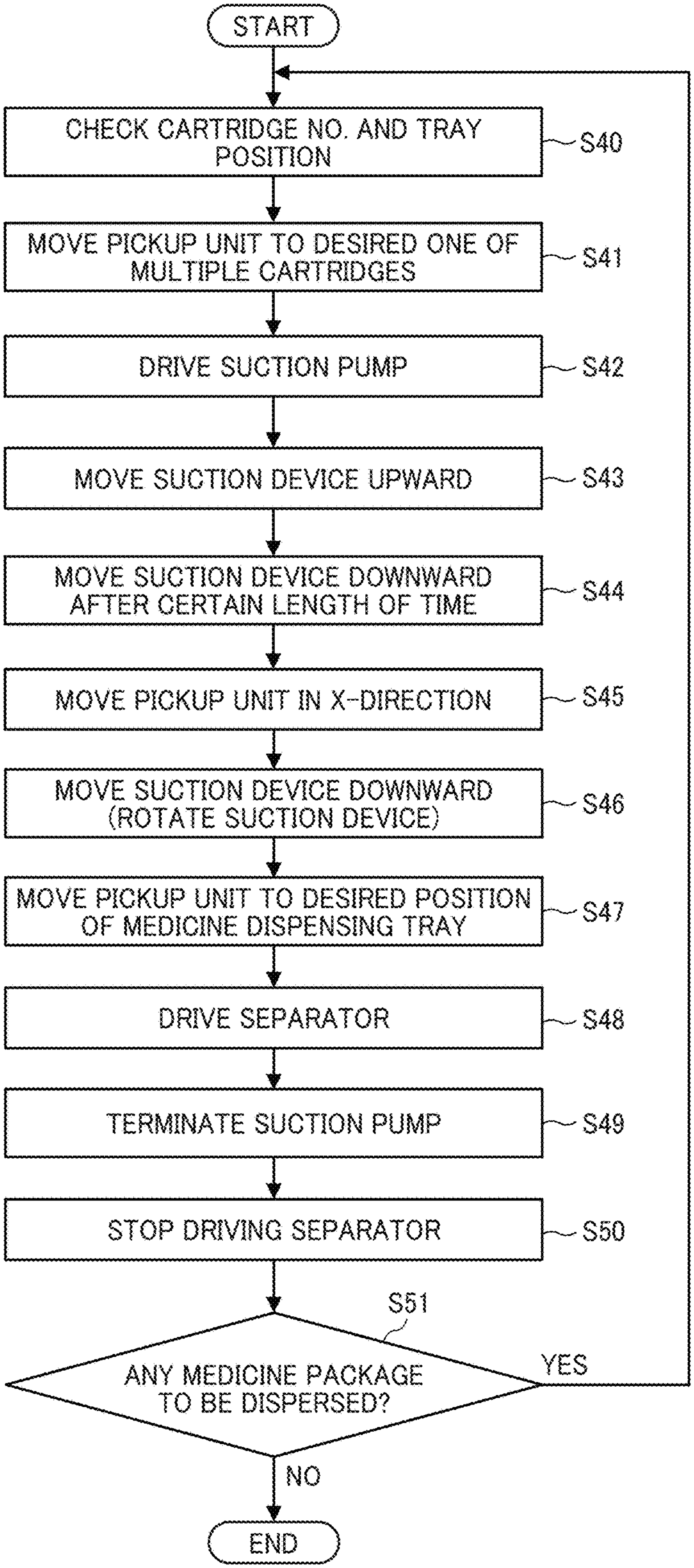
FIG. 17 is a flowchart of the operation flow of a pickup unit according to the second example of the present disclosure different from the first example of the present disclosure.

FIG. 17 is a flowchart of the operation flow of a pickup unit 50B according to the second example of the present disclosure.

The operation flow of the pickup unit 50B according to the second embodiment of the present disclosure described below with reference to FIG. 17 is different from the operation flow of the pickup unit 50A according to the first embodiment of the present disclosure described as above with reference to FIG. 16 in respect that the timing at which the solenoid 68 of the separator 64 is driven to operate is changed to the timing before the operation of the suction pump 48 is terminated. In other words, the operation flow of the pickup unit 50B according to the second embodiment of the present disclosure described below with reference to FIG. 17 is different from the operation flow of the pickup unit 50A according to the first embodiment of the present disclosure described as above with reference to FIG. 16 in respect that the timing at which the solenoid 68 of the separator 64 is driven to operate is changed to the timing before the suction holding of one of the multiple medicine packages 2 by the suction device 51 is released.

The steps S40 to S47 of the operation flow of the pickup unit 50B according to the second embodiment of the present disclosure described below with reference to FIG. 17 are equivalent to the steps S20 to S27 of the operation flow of the pickup unit 50A according to the first embodiment of the present disclosure described as above with reference to FIG. 16. The operation flow according to the second embodiment of the present disclosure is different from the operation flow according to the first embodiment of the present disclosure in respect that the solenoid 68 of the separator 64 is driven to operate in the step S48 before the suction pump 48 is stopped in the step S49 or the suction holding of one of the multiple medicine packages 2 by the suction device 51 is released.

In the second embodiment of the present disclosure, the separating head 65 of the separator 64 acts on one of the multiple medicine packages 2 before the suction holding of one of the multiple medicine packages 2 by the suction device 51 is released. Due to such a configuration, with the medication support device according to the second embodiment of the present disclosure, the separator 64 is instructed to start separating operation before the suction holding of one of the multiple medicine packages 2 by the pair of suction pads 52 is released by vacuum breakdown. Accordingly, the changes in posture or attitude such as the changes in the level of inclination due to the imbalanced sticking power of one of the multiple medicine packages 2 to the suction device 51 can be prevented, and the degree of reliability to dispense medicines to one of the multiple medicine dispensing trays can be increased.

Third Embodiment

The third embodiment of the present embodiment that is different from the first embodiment of the present disclosure is described below with reference to FIG. 15, FIG. 18A, FIG. 18B, and FIG. 19.

FIG. 15 is a control block diagram illustrating a schematic control structure for the medication support device 200, including, in particular, the pack sensor 75 that is boxed in dotted lines, according to the third example of the present disclosure.

Figure 18B:
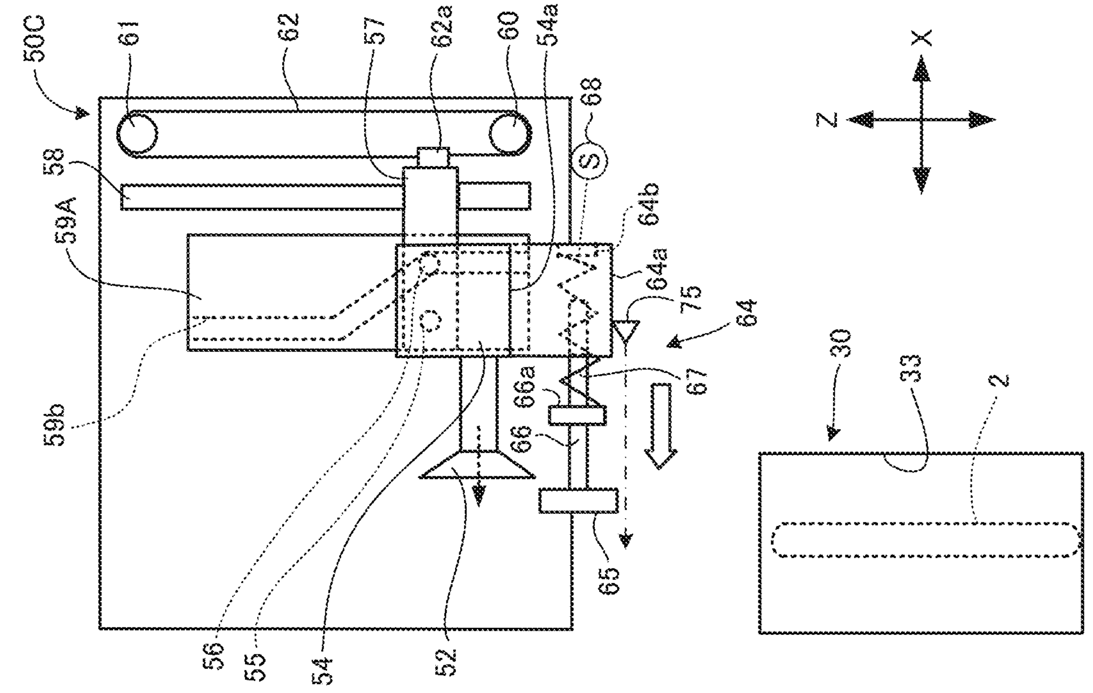
FIG. 18A and FIG. 18B are front views of a separator provided for a pickup unit and illustrate the structure or operation of the separator, according to the third embodiment of the present disclosure.
Figure 18A:
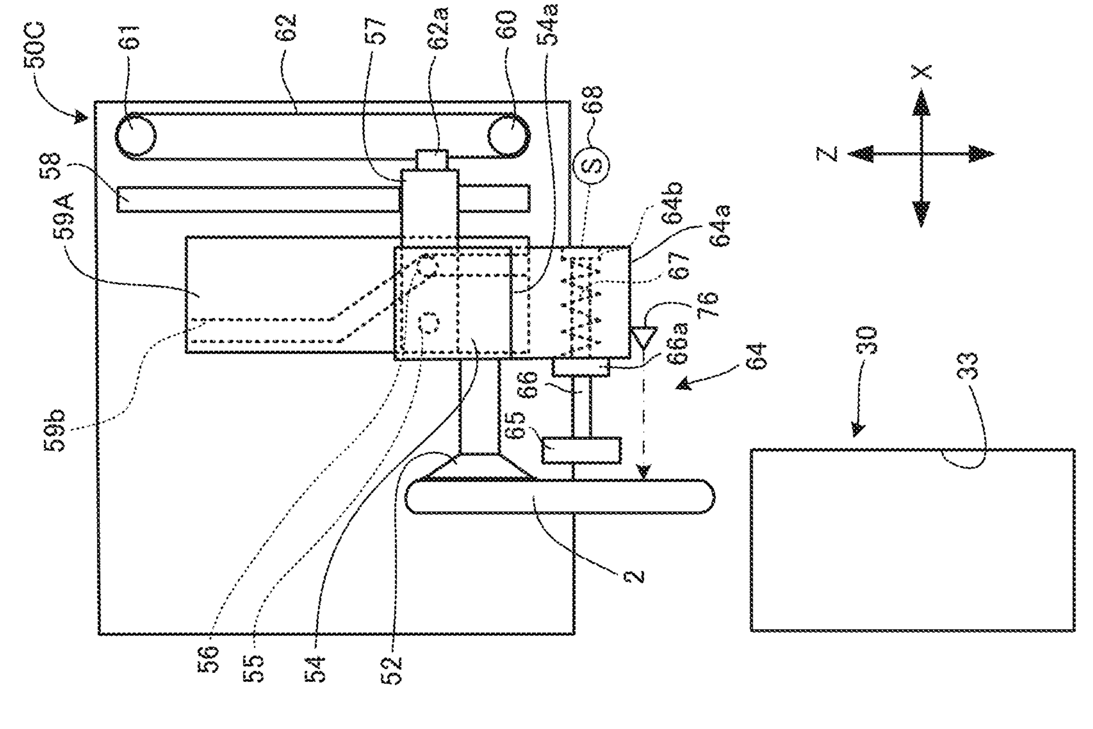

FIG. 18A and FIG. 18B are front views of the separator 64 provided for the pickup unit 50C and illustrate the structure or operation of the separator 64, according to the third embodiment of the present disclosure.

Figure 19:
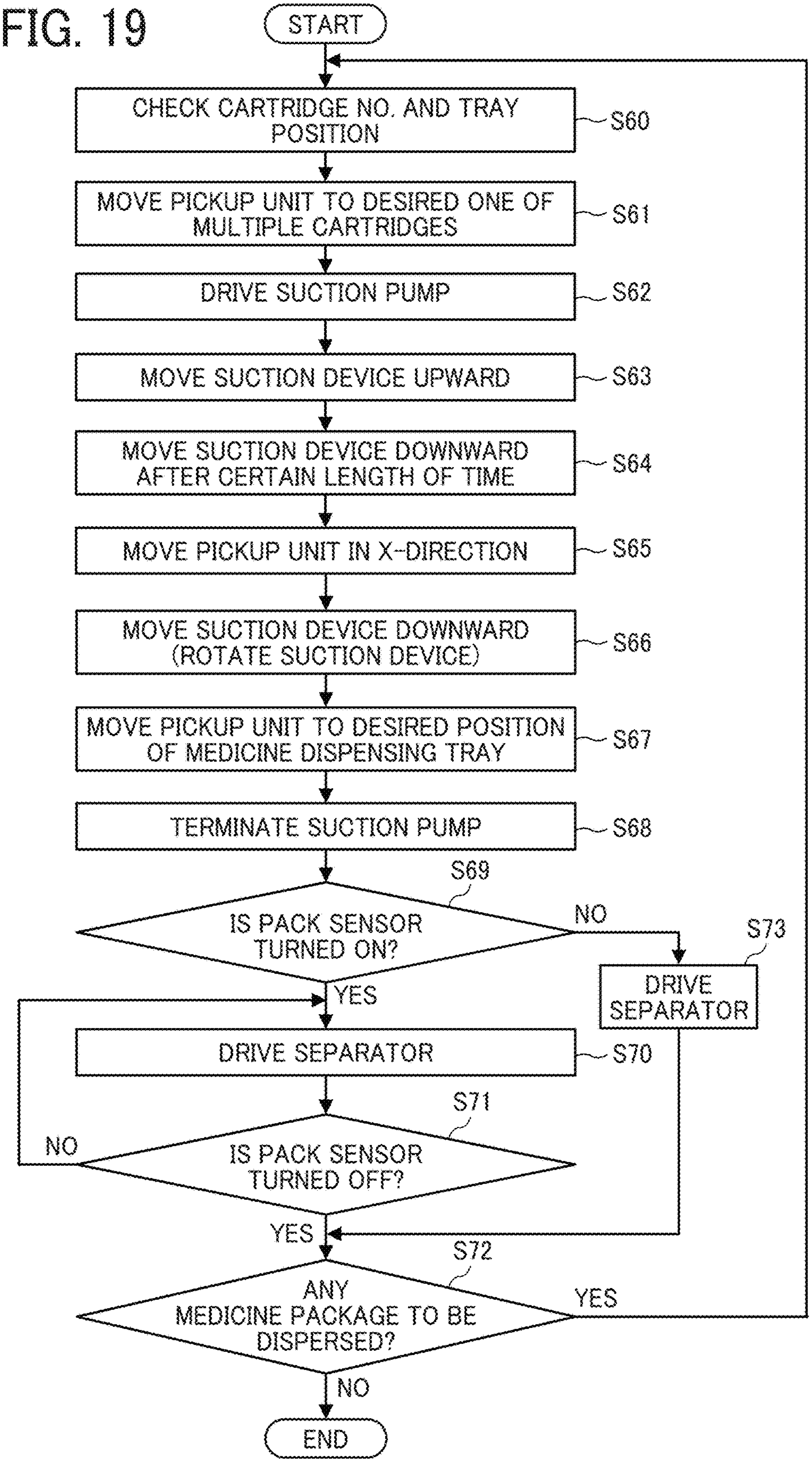
FIG. 19 is a flowchart of the operation flow of a pickup unit according to the third example of the present disclosure.

FIG. 19 is a flowchart of the operation flow of the pickup unit 50 illustrated in FIG. 18A and FIG. 18B, according to the present embodiment.

Typically, the medication support device 200 according to the third embodiment of the present disclosure is different from the pickup unit 50 according to the control sample of the above embodiments of the present disclosure described above with reference to FIG. 1A to FIG. 13 in that the pickup unit 50C in which the structure and operation of the pickup unit 50 is changed is adopted. The other configurations or operations of the present embodiment are equivalent to those of the medication support device 200 according to the first embodiment of the present disclosure described as above with reference to FIG. 14A, FIG. 14B, FIG. 15, and FIG. 16.

Typically, the pickup unit 50C according to the third embodiment of the present disclosure is different from the pickup unit 50A according to the first embodiment of the present disclosure described as above with reference to FIG. 14A, FIG. 14B, FIG. 15, and FIG. 16 in that the pack sensor 75 is arranged close to the separator 64 and the CPU of the controller 150 instructs the separator 64 to perform separating operation based on the detection information obtained by the pack sensor 75 after the suction holding of one of the multiple medicine packages 2 by the suction device 51 is released.

The pack sensor 75 according to the present embodiment is arranged close to the separator 64, and serves as a sensor that detects whether there is any one of the multiple medicine packages by detecting whether one of the multiple medicine packages 2 is being sucked and held by the pair of suction pads 52 of the suction device 51. As the pack sensor 75, for example, a light reflection type photosensor or a light transmission type photosensor is used.

The operation in the third embodiment of the present disclosure that is different from the operation in the first embodiment of the present disclosure is described below with reference to FIG. 18A, FIG. 18B, and FIG. 19. The operation flow according to the third embodiment of the present disclosure starts from the step S60, and the steps S60 to S68 of the operation flow according to the third embodiment of the present disclosure are equivalent to the steps S20 to S28 of the operation flow of the pickup unit 50A according to the first embodiment of the present disclosure described as above with reference to FIG. 16. In the third embodiment of the present disclosure, in a step S69, a step S70, a step S71, a step S72, and a step S73, the data indicating whether there is any one of the multiple medicine packages 2 after the suction holding of one of the multiple medicine packages 2 by the suction device 51 is released, which is the detection information obtained by the pack sensor 75, is utilized.

In other words, when one of the multiple medicine packages 2 is sucked and held by the pair of suction pads 52 of the suction device 51, the pack sensor 75 is turned on. Accordingly, the separating head 65 of the separator 64 is driven to operate to force the target one of the multiple medicine packages 2 to be taken off from the pair of suction pads 52 (see the step S70). On the other hand, when the pack sensor 75 is turned off, the medicine package 2 has already been released and separated from the pair of suction pads 52. Accordingly, the operation of the separating head 65 provided for the separator 64 is stopped (see the step S73). Further, in the step S71 of the operation flow according to the third embodiment of the present disclosure, whether the pack sensor 75 is turned off after the operation of the separating head 65 has been started is checked. Due to such a configuration, whether one of the multiple medicine packages 2 has already been released and made separate from the pair of suction pads 52 can finally be checked.

In the third embodiment of the present disclosure, the suction holding of one of the multiple medicine packages 2 by the pair of suction pads 52 is released by vacuum breakdown before the separating head 65 that serves as a separating member starts operating. Moreover, in the third embodiment of the present disclosure, the pack sensor 75 that serves as a sensor detects whether one of the multiple medicine packages 2 is being dropped or stuck. Separating operation is performed when one of the multiple medicine packages 2 is detected, and separating operation is not performed when none of the multiple medicine packages 2 is detected. Accordingly, with the medication support device according to the third embodiment of the present disclosure, the length of time required for the separating operation can be shortened.

Fourth Example

The medicine pack control unit 70 provided for the pickup unit 50D is described below with reference to FIG. 20, FIG. 21A, FIG. 21B, and FIG. 21C.

Figure 20:
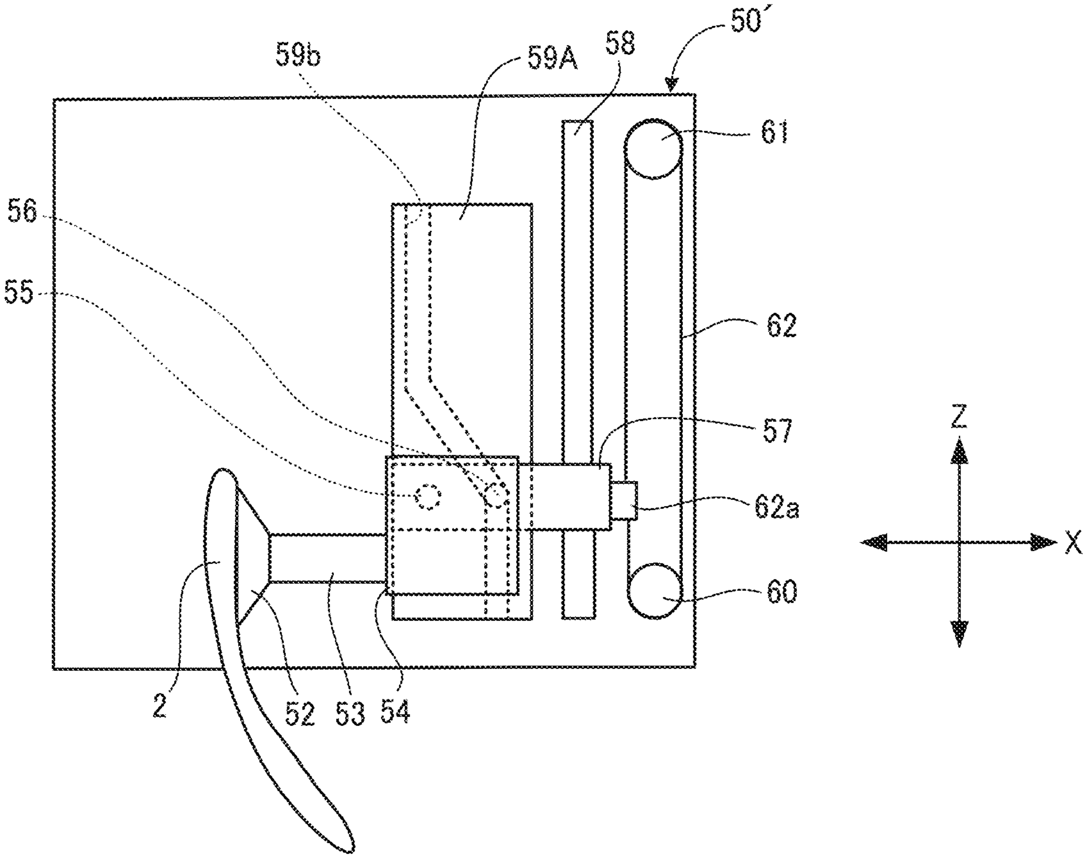
FIG. 20 is a front view of a pickup unit according to a fourth embodiment of the present disclosure and illustrates the medicine pack that is curled by a suction pad.

FIG. 20 is a front view of a pickup unit 50' according to the fourth embodiment of the present disclosure and illustrates the medicine pack that is curled by the suction pad 52.

Figure 21C:
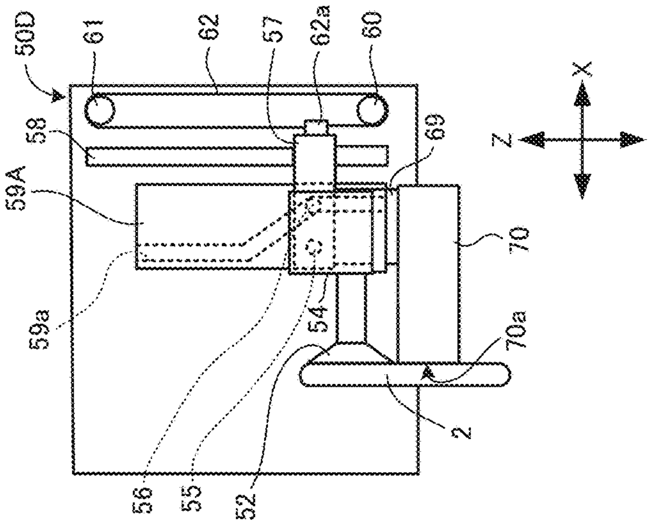
FIG. 21A, FIG. 21B, and FIG. 21C are front views of a medicine pack control unit provided for a pickup unit, according to a fourth embodiment of the present disclosure, and illustrates the structure and the progression of the operation of the medicine pack control unit.
Figure 21B:
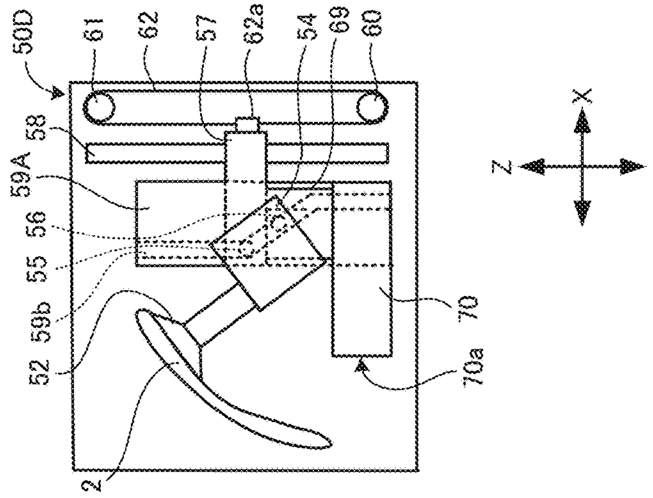
Figure 21A:
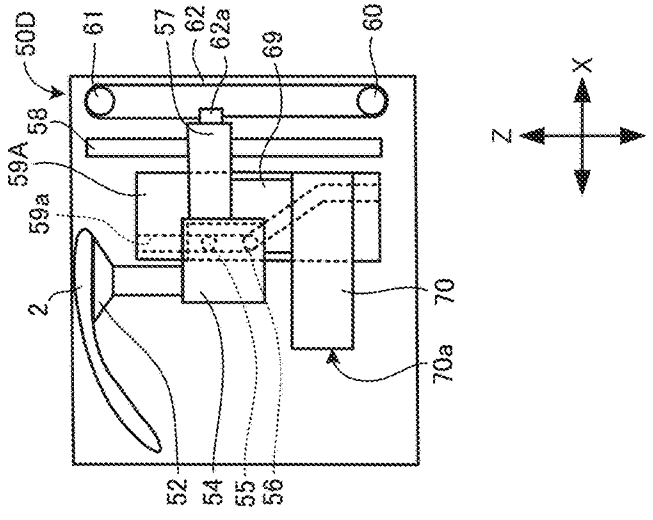

FIG. 21A, FIG. 21B, and FIG. 21C are front views of the medicine pack control unit 70 provided for the pickup unit 50D, according to the fourth embodiment of the present disclosure, and illustrates the structure and the progression of the operation of the medicine pack control unit 70.

The dispensing sheet used for dispending the multiple medicine packages 2 may be made of various kinds of materials such as cellophane, resin film, aluminum (A1) film. In some cases, as illustrated in FIG. 20 as the pickup unit 50', one of the multiple medicine packages 2 that is sucked by the pair of suction pads 52 may be unintentionally curled depending on the environment in which the medication support device 200 is installed, how one of the multiple medicine packages 2 is sucked up, or an excessive quantity or number of enclosed medicines. In order to deal with such curling of the medicine packages 2, the fourth embodiment of the present disclosure described is designed as illustrated in FIG. 21A, FIG. 21B, and FIG. 21C.

The pickup unit 50' according to the fourth embodiment of the present disclosure is different from the pickup unit 50 according to the control sample of the above embodiments of the present disclosure described as above with reference to, for example, FIG. 7A, FIG. 7B, FIG. 8A, FIG. 8B, FIG. 8C, FIG. 8D, FIG. 8E, and FIG. 8F in respect that the guide unit 59A provided with the guide groove 59*b* is adopted in place of the guide unit 59.

In order to deal with such curling of the medicine packages 2, in the pickup unit 50D according to the fourth embodiment of the present disclosure described with reference to FIG. 21A, FIG. 21B, and FIG. 21C, the medicine pack control unit 70 is arranged close to the pair of suction pads 52 where the opening planes of the pair of suction pads 52 that suck and hold one of the multiple medicine packages 2 that is curled are lateral and in a horizontal orientation and the multiple medicine packages 2 are in a vertical orientation. When the posture or attitude of the medicine pack control unit 70 is as illustrated in FIG. 21A, the upper portion of the medicine pack control unit 70 is fixed to the lower portion of the suction device base 57 through the base coupler 69. The medicine pack control unit 70 includes a rectangular member, and the upper portion of the medicine pack control unit 70 is fixed to the base coupler 69. The upper portion of the base coupler 69 is fixed to the lower portion of the suction device base 57. The medicine pack control unit 70 controls the position or posture of the target one the multiple medicine packages 2 that is curled upon being sucked and held by the pair of suction pads 52.

The medicine pack control unit 70 is configured to move up and down together with the up-and-down movement of the suction device base 57. In the fourth embodiment of the present disclosure, the separator 64 according to the first embodiment of the present disclosure is hidden from view in FIG. 20, FIG. 21A, FIG. 21B, and FIG. 21C. However, as a matter of course, the separator 64 according to the first embodiment of the present disclosure is present also in the fourth embodiment of the present disclosure.

The progression of the operation of the pickup unit 50D is described below. As described above in the control sample of the embodiments of the present disclosure with reference to, for example, FIG. 8C and FIG. 8D, as the suction device lifting and lowering motor 63 is reversely operated as illustrated in FIG. 21A, the pair of suction pads 52 move downward while sucking one of the multiple medicine packages 2 by the pair of suction pads 52, and the front end of one of the multiple medicine packages 2 is pulled out from one of the multiple cartridges 10. The front end of the medicine package indicates a side of the medicine package to be absorbed or sucked up by the pair of suction pads 52, and the same applies in the following description. Subsequently, by the operation of the conveyance unit 90 (see FIG. 1A and FIG. 1B), the pickup unit 50D is moved in the X-direction, and the rear end of one of the multiple medicine packages 2 is drawn out or picked up from one of the multiple cartridges 10. In such drawing out operation, one of the multiple medicine packages 2 that is sucked by the pair of suction pads 52 is curled in such a manner as described above.

In the operation illustrated in FIG. 21B, as described above in the control sample of the embodiments of the present disclosure with reference to, for example, FIG. 8E and FIG. 8F, one of the multiple medicine packages 2, which is approximately in a horizontal state and is sucked and held by the pair of suction pads 52, is rotated by substantially 90 degrees by the operation of the suction device lifting and lowering motor 63 to change the posture to an approximately vertical or upright posture.

In such rotational operation, the rotation axis 55 that is arranged on the suction-pad supporting member 54 moves along the guide groove 59*a* of the guide unit 59. In FIG. 21B, the rotation axis 55 that is arranged on the suction-pad supporting member 54 moves along the guide groove 59*b* of the guide unit 59A. Accordingly, the posture of one of the multiple medicine packages 2 is changed from an approximately horizontal posture to an approximately vertical posture. The medicine pack control unit 70 under such conditions moves downward together with the downward movement of the suction device base 57.

Subsequently, as illustrated in FIG. 21C, one of the multiple medicine packages 2, which is approximately in a horizontal state and is sucked and held by the pair of suction pads 52, is rotated by substantially 90 degrees to change the posture to an approximately vertical or upright posture. The medicine pack control unit 70 under such conditions moves downward together with the downward movement of the suction device base 57, and the curled portion of one of the multiple medicine packages 2 sucked and held by the pair of suction pads 52 hits a pack-contacting control face 70*a* of the medicine pack control unit 70. As a result, as illustrated in FIG. 21C, the curled portion of one of the multiple medicine packages 2 is straightened to a desired state of the medicine packages 2 under normal operating conditions.

In the fourth embodiment of the present disclosure, as described above, after the pair of suction pads 52 rotate and move downward, the curled portion of one of the multiple medicine packages 2 hits the pack-contacting control face 70*a* of the medicine pack control unit 70. As the curled portion follows the shape of the pack-contacting control face 70*a*, the curled portion is straightened and the problem is solved.

With the medication support device according to the fourth embodiment of the present disclosure, the position or posture of the target one the multiple medicine packages 2 can be controlled while the pair of suction pads 52 are holding one of the multiple medicine packages 2, and the target one of the multiple medicine packages 2 can be prevented from dropping into a place other than a desired place such as a predetermined one of the multiple partitions 33 of one of the multiple medicine dispensing trays 30 when the holding operation is released such that the target one of the multiple medicine packages 2 will drop off.

Fifth Example

Figure 22B:
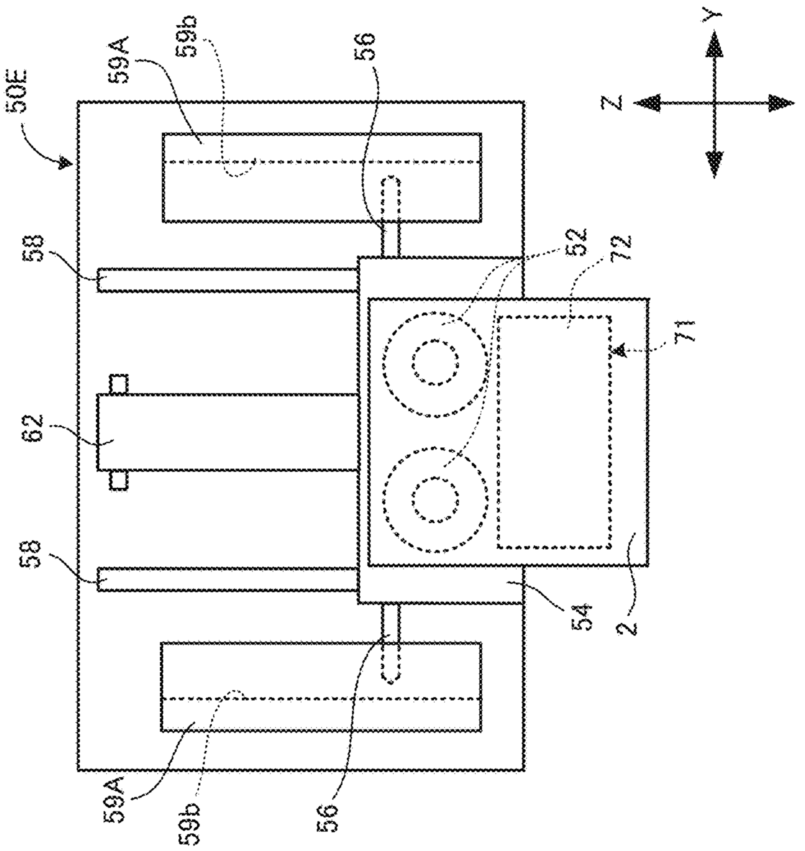
FIG. 22B is a side view of the unit that serves as both a separator and a medicine pack control unit and is provided for the pickup unit of FIG. 22A, according to the fifth embodiment of the present disclosure.
Figure 22A:
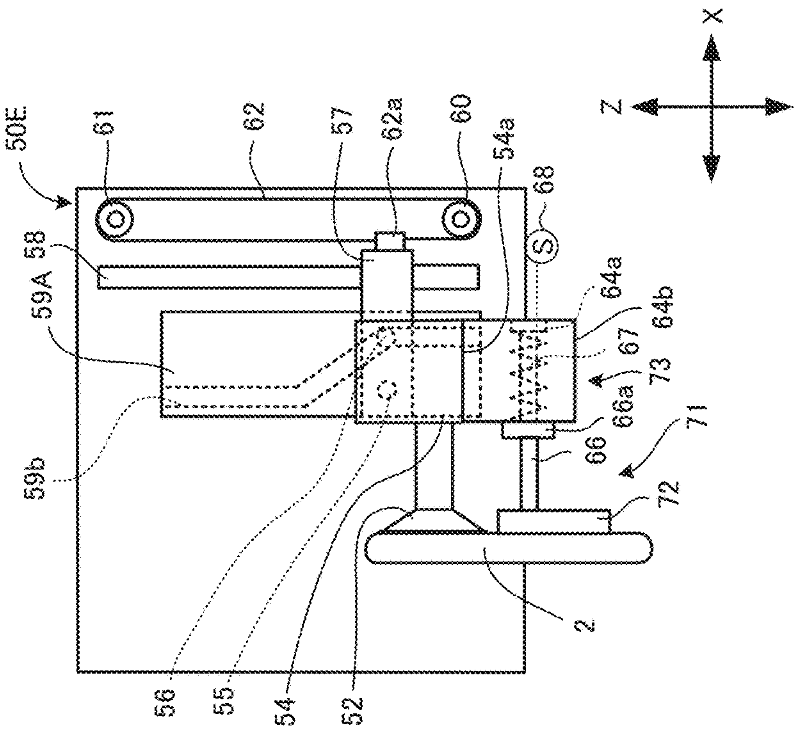
FIG. 22A is a front view of a unit that serves as both a separator and a medicine pack control unit and is provided for a pickup unit, according to a fifth embodiment of the present disclosure.

FIG. 22A is a front view of a unit that serves as both a separator and a medicine pack control unit and is provided for a pickup unit 50E, according to the fifth embodiment of the present disclosure.

FIG. 22B is a side view of the unit that serves as both a separator and a medicine pack control unit and is provided for the pickup unit 50E of FIG. 22A, according to the fifth embodiment of the present disclosure.

As illustrated in FIG. 22A and FIG. 22B, the pickup unit 50E according to the fifth embodiment of the present disclosure is provided with a separation control unit 71 in which a separator configured to make the picked-up one of the multiple medicine packages 2 separate from the pair of suction pads 52 partially serve as a medicine pack controller.

As will be described later, the separation control unit 71 is provided with a unit that serves as both a separator and a medicine pack control unit.

The separation control unit 71 according to the fifth embodiment of the present disclosure includes a separation controlling member 72 that hits and contacts one of the multiple medicine packages 2 with an area broader than the separating head 65 according to the first embodiment of the present disclosure described as above with reference to FIG. 14A and FIG. 14B, and a separator 73 that serves as a separator and uses the separation controlling member 72 to force one of the multiple medicine packages 2 to be separate from the pair of suction pads 52.

The description to detail of the separator 73 that serves as a separator is substantially equivalent to the configuration or structure of the separator 64 according to the first embodiment of the present disclosure described as above with reference to FIG. 14A and FIG. 14B. However, the description to detail of the separator 73 that serves as a separator is different from the configuration or structure of the separator 64 according to the first embodiment of the present disclosure described as above with reference to FIG. 14A and FIG. 14B in respect that the separator 73 according to the present embodiment includes the separation controlling member 72 that contacts one of the multiple medicine packages 2 with an area broader than the separating head 65 of the separator 64.

Once the separation control unit 71 starts operating in the state as illustrated in FIG. 22A, a wide area of one of the multiple medicine packages 2 sucked and held by the pair of suction pads 52 can be pushed by the separation controlling member 72. Accordingly, the target one of the multiple medicine packages 2 caught by or stuck to the pair of suction pads 52 can be made separate with even greater reliability.

With the medication support device according to the fifth embodiment of the present disclosure, a wide area of the target one of the multiple medicine packages 2 can be controlled, and a wide area can be pushed when the separating operation is performed. Accordingly, the degree of reliability to dispense medicines to one of the multiple medicine dispensing trays can be increased.

In FIG. 22A and FIG. 22B, the pair of suction pads 52 that serve as a pair of air suction units or suction units are horizontally arranged. However, no limitation is indicated thereby, and any number of suction units may be arranged and those suction units may be arranged differently. It is desired that the multiple suction units be arranged symmetrically in pairs across a line of symmetry and the line of symmetry be the center line of the multiple medicine packages 2. This is because if the pair of suction pads 52 are arranged at different levels or stages in the vertical direction or the Z-direction, there is some concern that the target one of the multiple medicine packages 2 is inclined in an undesired manner and drops. In such cases, medicine dispensing cannot appropriately be performed.

First Modification

Figure 23:
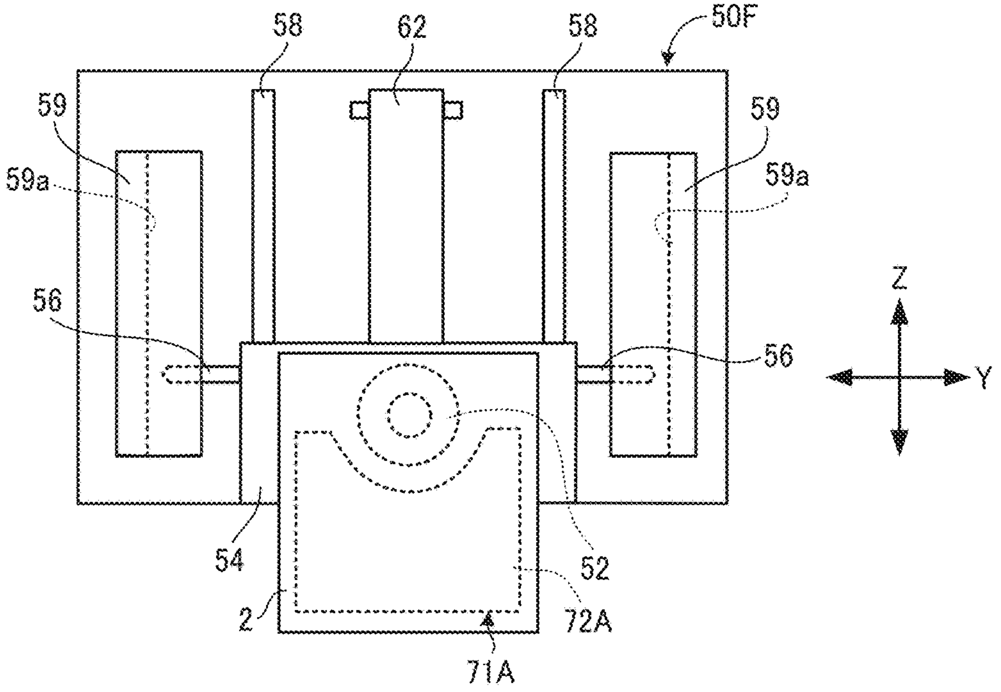
FIG. 23 is a side view of a separation control unit provided for a pickup unit according to a first modification of the fifth embodiment of the present disclosure.

FIG. 23 is a side view of a separation control unit 71A provided for a pickup unit 50F according to the first modification of the fifth embodiment of the present disclosure.

In place of the configuration or structure described above with reference to FIG. 22A and FIG. 22B where the separation control unit 71 has a rectangular shape, a separation controlling member 72A according to the first modification of the embodiments of the present disclosure in which the separation control unit 71A has a cutout portion at its rectangular shape so as not to contact the single suction pad 52 while that suction pad 52 is moving may be adopted as illustrated in FIG. 23. FIG. 23 illustrates a case where a single suction pad 52 is arranged.

Second Modification

Figure 24:
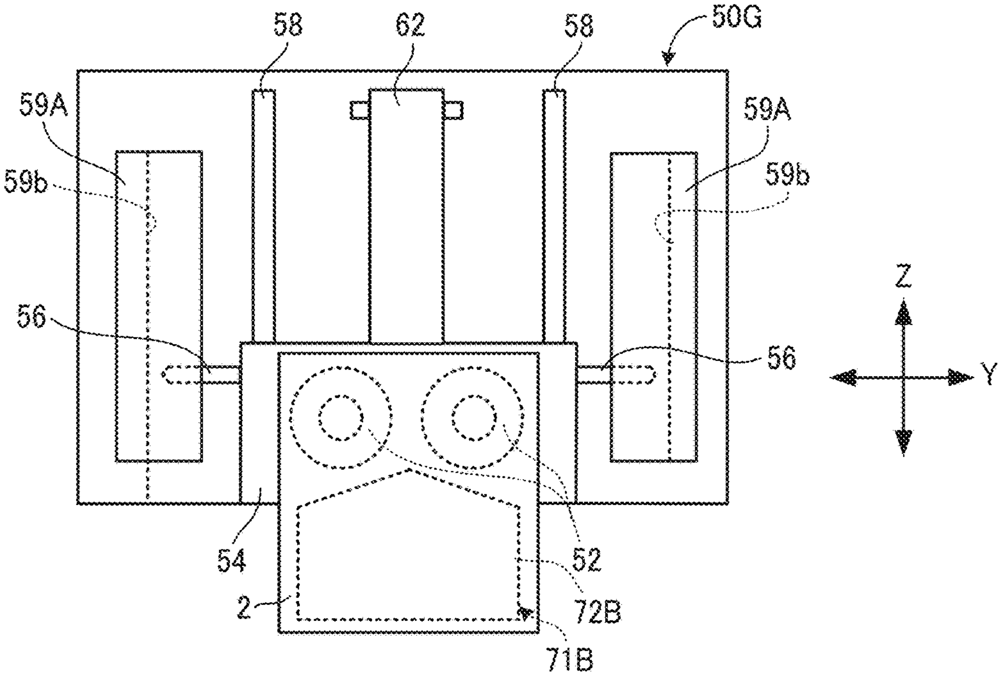
FIG. 24 is a side view of a separation control unit provided for a pickup unit according to a second modification of the fifth embodiment of the present disclosure.

FIG. 24 is a side view of a separation control unit 71B provided for a pickup unit 50G according to the second modification of the fifth embodiment of the present disclosure.

In place of the configuration or structure described above with reference to FIG. 22A, FIG. 22B, and FIG. 23, a separation controlling member 72B according to the second modification of the embodiments of the present disclosure in which the separation control unit 71B has an approximately polygonal shape may be adopted as illustrated in FIG. 24.

Third Modification

Figure 25:
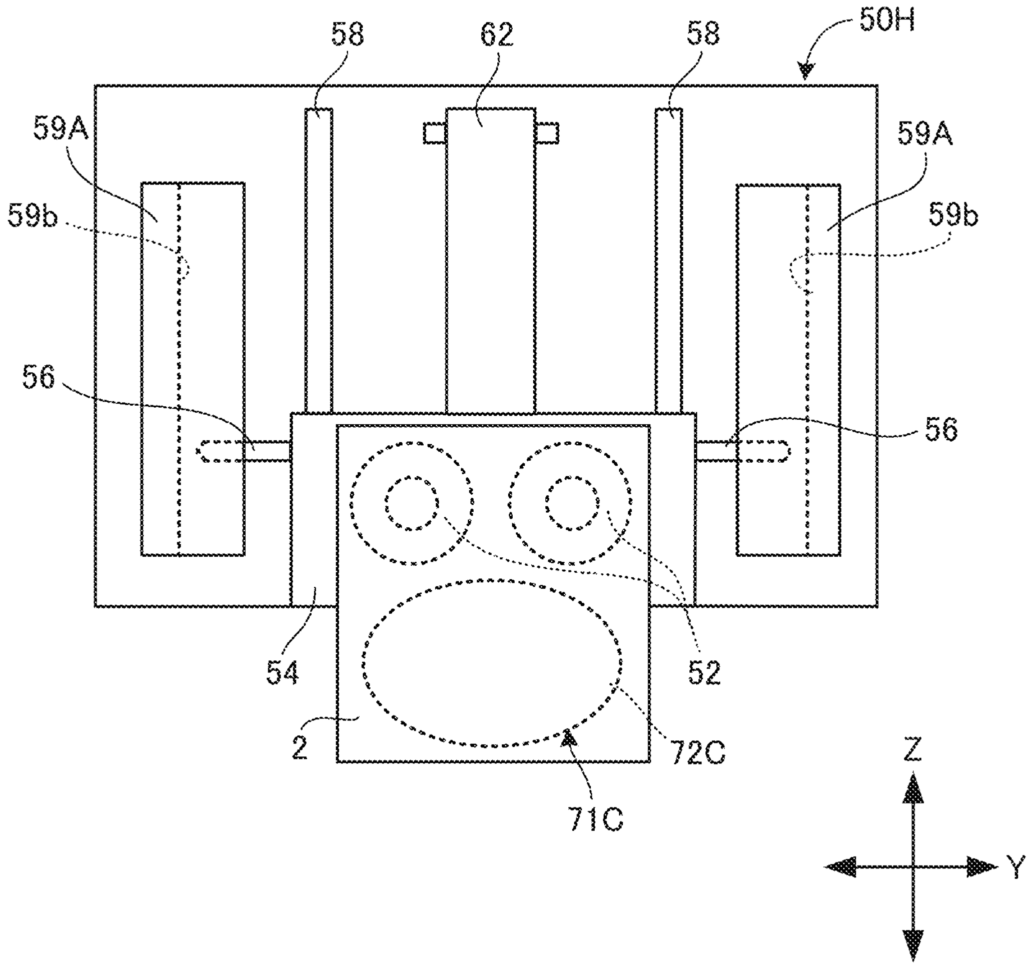
FIG. 25 is a side view of a separation control unit provided for a pickup unit according to a third modification of the fifth embodiment of the present disclosure.

FIG. 25 is a side view of a separation control unit 71C provided for a pickup unit 50H according to the third modification of the fifth embodiment of the present disclosure.

In place of the configuration or structure described above with reference to FIG. 22A, FIG. 22B, FIG. 23, and FIG. 24, a separation controlling member 72C according to the third modification of the embodiments of the present disclosure in which the separation control unit 71C has an elliptical shape or a circular shape may be adopted as illustrated in FIG. 25.

It is desired that the multiple suction pads 52 be shaped and arranged symmetrically in pairs across a line of symmetry and the line of symmetry be the center line of the multiple medicine packages 2 that are sucked and held by the pair or suction pads 52.

In the fifth embodiment of the present disclosure and the first to third modifications of the embodiments of the present as described above, the separation controlling member 72, the separation controlling member 72A, the separation controlling member 72B, and the separation controlling member 72C are configured to work or operate together with the posture changing operation of the pair of suction pads 52 in a similar manner to the separating head 65 according to the first embodiment of the present disclosure described as above with reference to FIG. 14A and FIG. 14B. However, no limitation is intended thereby, and the separation controlling member 72, the separation controlling member 72A, the separation controlling member 72B, and the separation controlling member 72C may be arranged in an immovable state close to the pair of suction pads 52 that have changed their posture or attitude to suck and hold one of the multiple medicine packages 2 vertically, so as not to interfere with, for example, other elements or movable parts. The separation controlling member 72, the separation controlling member 72A, the separation controlling member 72B, and the separation controlling member 72C may be configured so as to operate together with the up-and-down movement of the suction device base 57.

Sixth Embodiment

Figure 26B:
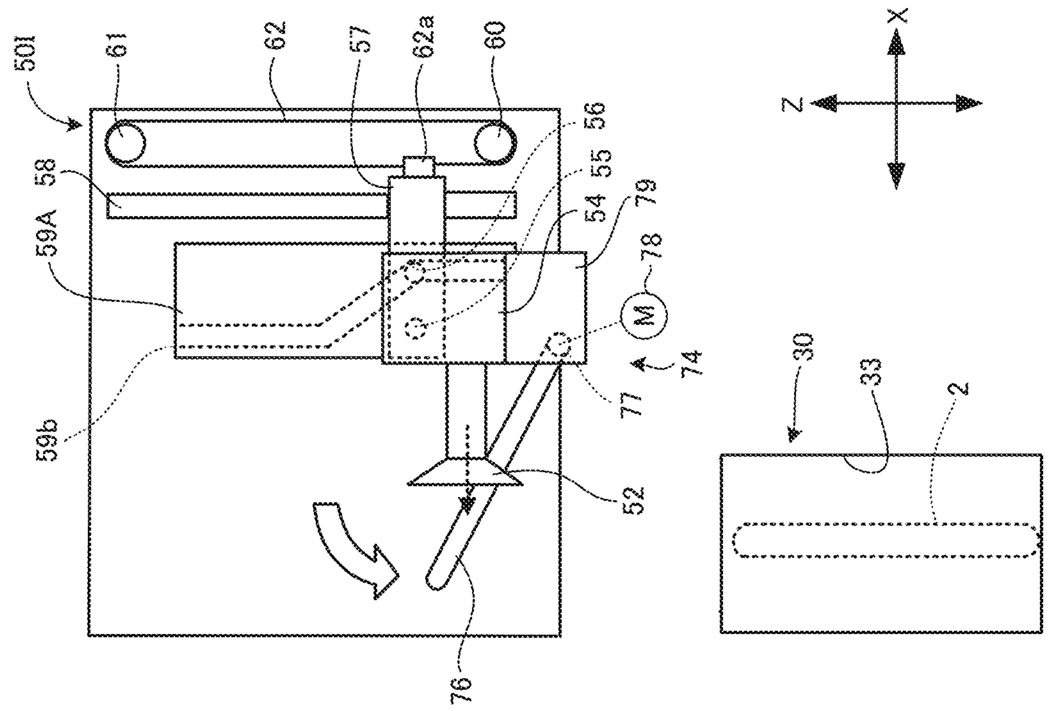
FIG. 26A and FIG. 26B are front views of a separator provided for a pickup unit and illustrate the structure or operation of the separator, according to the sixth embodiment of the present disclosure.
Figure 26A:
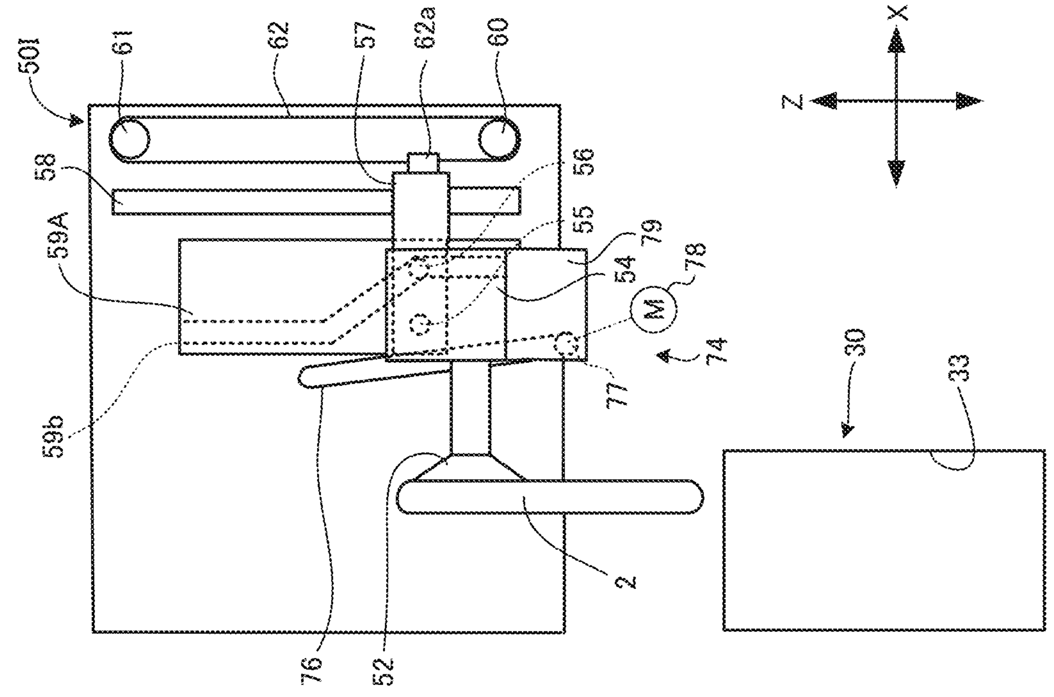

FIG. 26A and FIG. 26B are front views of a separator 74 provided for a pickup unit 50I and illustrate the structure or operation of the separator 74, according to the sixth embodiment of the present disclosure.

In the separator 74 according to the sixth embodiment of the present disclosure, the separating member 76 is configured to act on an upper portion of one of the multiple medicine packages 2 than the center position of the target one of the multiple medicine packages 2 sucked and held by the pair of suction pads 52.

The separator 74 according to the present embodiment is provided with an immovable member 79 fixed to the base of the guide unit 59A, the separating member 76 that serves as a separator and is provided for the immovable member 79 in a pivotable manner within a range of a predetermined angle, a spindle 77 that supports the separating member 76 in a pivotable manner, and a drive motor 78 that serves as a driver and is coupled to the spindle 77 to drive the separating member 76 to rotate within a range of a predetermined angle. The separating member 76 according to the present embodiment is shaped like a stick, and is arranged so as not to interfere with the other components or elements of the pickup unit 50I.

The operation according to the sixth embodiment of the present disclosure is described below. In the sixth embodiment of the present disclosure, the operation as illustrated in FIG. 26B is performed when one of the multiple medicine packages 2 is sucked and held vertically by the pair of suction pads 52 as illustrated in FIG. 26A. More specifically, in a similar manner to the first embodiment of the present disclosure as described above, the operation of the separator 74 is started after the operation of the suction pump 48 is terminated and the suction holding of one of the multiple medicine packages 2 by the pair of suction pads 52 is released by vacuum breakdown. As illustrated in FIG. 14B, the separating member 76 is driven to rotate by the rotation of the drive motor 78 in the direction indicated by a large hollow arrow to hit an upper portion of the pack to drop the pack. As a result, one of the multiple medicine packages 2 sucked and held in the vertical orientation by the pair of suction pads 52 is forced to be taken off, and is orderly stored in a predetermined one of the multiple partitions 33 of one of the multiple medicine dispensing trays 30 as indicated by dotted lines. Subsequently, the drive motor 78 is driven in the reverse direction to stop the operation of the separator 74.

A failure of dropping the medicine pack is typically caused by an extreme curled portion of the medicine pack on the edge. This is because such a curled portion tends to be caught by the pair of the suction pads 52 that serve as a suction unit. Alternatively, a failure of dropping the medicine pack is typically caused by the static electricity generated between the suction unit and the medicine pack. This is because such static electricity tends to make the medicine pack stuck to the suction unit. In order to deal with such a situation, in the sixth embodiment of the present disclosure, the separating member 76 acts on a portion close to a problematic site. Accordingly, the separating operation can successfully be done.

With the medication support device according to the sixth embodiment of the present disclosure, an area above the center of the contact portion between the pair of suction pads 52 and the picked-up one of the multiple medicine packs is pressed by the separating member 76 to address a portion even closer to a problematic site responsible for a failure of dropping the medicine pack. Accordingly, the separating operation can successfully be done.

In the sixth embodiment of the present disclosure described with reference to FIG. 26A and FIG. 26B, the separating member 76 is rotatably supported by the spindle 77. However, no limitation is intended thereby, and the separating member 76 may be configured to operate linearly.

Seventh Embodiment

The separator 74 in the pickup unit 50J according to the seventh embodiment of the present disclosure is described below with reference to FIG. 27A and FIG. 27B.

Figure 27B:
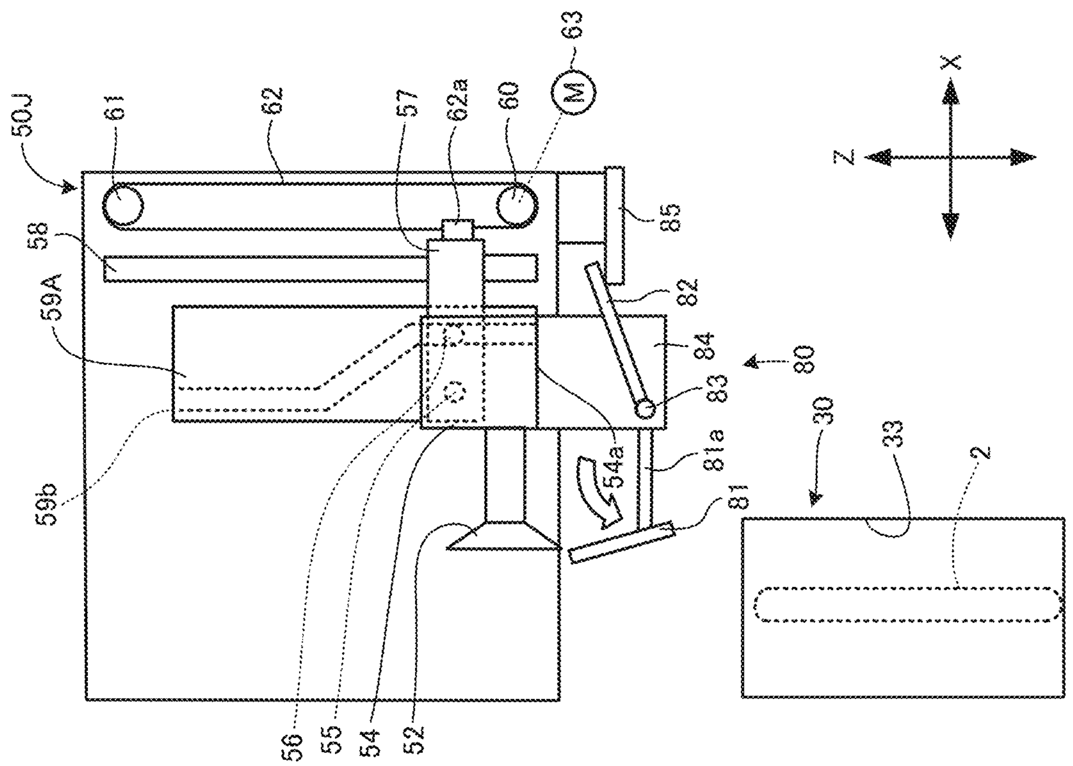
FIG. 27A and FIG. 27B are front views of a separator provided for a pickup unit and illustrate the structure or operation of the separator, according to a seventh embodiment of the present disclosure.
Figure 27A:
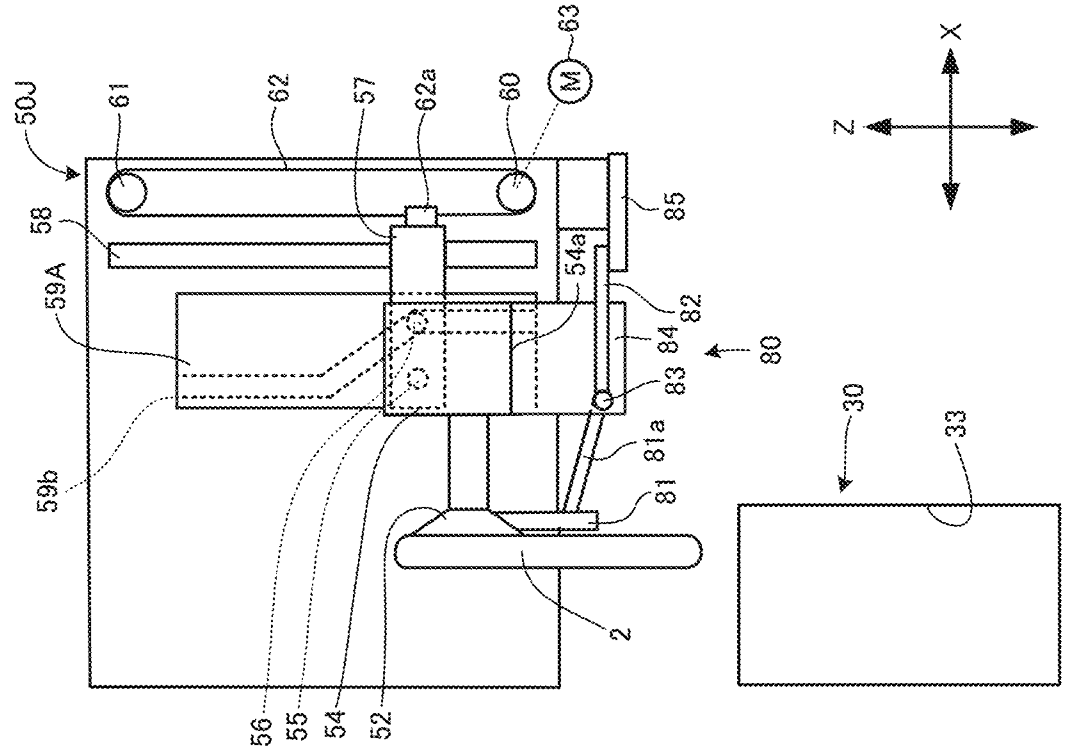

FIG. 27A and FIG. 27B are front views of a separator 80 provided for a pickup unit 50J and illustrate the structure or operation of the separator 80, according to the seventh embodiment of the present disclosure.

The separator 80 according to the present embodiment is used to separate the picked-up one of the multiple medicine packages 2 from the pair of suction pads 52. In the seventh embodiment of the present disclosure, the separator 80 operates or works together with the operation of the suction device lifting and lowering motor 63 that serves as a suction-device driver.

In the pickup unit 50J according to the seventh embodiment of the present disclosure, in a similar manner to the pickup unit 50A according to the first embodiment of the present disclosure described as above with reference to FIG. 14A and FIG. 14B, the endless belt 62 is driven by the suction device lifting and lowering motor 63 to move in the up-and-down directions. Due to such a configuration, the suction device base 57 moves up and down.

A concrete example of the separator 80 includes a separating paddle 81 that serves as a separating member and is used to make the picked-up one of the multiple medicine packages 2 separate from the pair of suction pads 52, a paddle arm 81*a*, a lever 82, and a coupler 84 that supports the spindle 83 in a rotatable manner within a predetermined range of angle. One end of the paddle arm 81*a* is fixed to the separating paddle 81, and the other end of the paddle arm 81*a* is fixed to a spindle 83. The base end of the lever 82 is fixed to the spindle 83, and the free end of the lever 82 can contact a lever abutment part 85 provided for the housing.

The coupler 84 according to the present embodiment is coupled to and fixed to the coupler 54*a* that is the bottom end of the suction-pad supporting member 54 as illustrated in FIG. 27A and FIG. 27B.

The operation according to the seventh embodiment of the present disclosure is described below. In the seventh embodiment of the present disclosure, the operation as illustrated in FIG. 27B is performed when one of the multiple medicine packages 2 is sucked and held vertically by the pair of suction pads 52 as illustrated in FIG. 27A. More specifically, in a similar manner to the first embodiment of the present disclosure as described above, the operation of the separator 80 is started after the operation of the suction pump 48 is terminated or after the suction holding of one of the multiple medicine packages 2 by the pair of suction pads 52 is released by vacuum breakdown.

When the pair of suction pads 52 of the suction device 51 is lowered by the rotation of the suction device lifting and lowering motor 63, the free end of the lever 82 that contacts the lever abutment part 85 provided for the housing of the pickup unit 50J is pushed up about a spindle 83 from the state as illustrated in FIG. 27A to the state as illustrated in FIG. 27B. By so doing, the separating paddle 81 of the paddle arm 81*a* coupled to the lever 82 rotates or swings in the direction indicated by the large hollow arrow within a predetermined range of angle to press one of the multiple medicine packages 2 caught by the pair of suction pads 52. As a result, the target one of the multiple medicine packages

2 is orderly dropped into a predetermined one of the multiple partitions 33 of one of the multiple medicine dispensing trays 30.

With the medication support device according to the seventh embodiment of the present disclosure, the suction-device driver can be shared or used in common without arranging an extra driver for the separator 80. Accordingly, saving in space and cost reduction can be expected.

The above embodiments of the present disclosure described above substantially include, for example, the following modifications.

In other words, a medication support device according to the first mode of the present disclosure includes a container such as the cartridge 10 that stores a plurality of medicine packs such as the multiple medicine packages 2 being stacked on top of each other in layers, a pickup device such as the pickup units 50A, 50B, 50C, 50D, 50E, and 50J that picks up a specific one of the multiple medicine packs from the container, a conveyor such as the conveyance unit 90 that conveys the specific one of the multiple medicine packs picked up by the pickup device, and a medicine dispenser such as the medicine dispensing tray in which the specific one of the multiple medicine packs conveyed by the conveyor are arranged. The medication support device such as the medication support device 200 according to the above embodiments of the present disclosure further includes a separator such as the separator 64, the separator 73, the separator 74, and the separator 80 configured to make the specific one of the multiple medicine packs picked up by the pickup device separate from the pickup device.

With the medication support device according to the first mode of the present disclosure, the medicine pack that is caught or stuck to the pickup device can be made separate from the pickup device and can be dispensed to the medicine dispenser. In other words, a medication support device can be provided that does not cause a failure of dropping the medicine pack regardless of the intensity of pressure of vacuum breakdown when the specific one of the multiple medicine packs picked up by the pickup device is placed in the medicine dispenser.

According to the second mode of the present disclosure, in the medication support device according to the first mode of the present disclosure, the multiple medicine packs are stacked on top of each other in layers in the holder, and the pickup device includes a suction device such as the suction pad 52 that is provided for the suction device 51 and picks up one of the multiple medicine packs downward from the container.

With the medication support device according to the second mode of the present disclosure, the multiple medicine packs that are stacked on top of each other in layers in the container can be picked up by the suction device on a one-by-one basis downward from the container.

According to the third mode of the present disclosure, in the medication support device according to the second mode of the present disclosure, the pickup device includes a suction-device driver such as the suction device lifting and lowering motor 63 configured to drive the suction device, and a suction-device guide such as the guide unit 59A configured to move the suction device. The suction-device guide is formed or provided with the rotation axis 55, the guide axis 56, the suction device base 57, the guide rod 58, and the guide groove 59*b*.

With the medication support device according to the third mode of the present disclosure, the position or attitude of the suction device can be changed. Accordingly, for example, the suction device can be turned upward when the medicine pack is to be taken out, and the suction device can be turned lateral when the medicines are to be dispersed to the medicine dispenser. Accordingly, the degree of reliability in the picking-up operation of one of the multiple medicine packs from the container using the pickup device can be increased, and the degree of reliability in the medicine dispensing of the medicine pack to the medicine dispenser can be increased.

According to the fourth mode of the present disclosure, in the medication support device according to the first mode of the present disclosure, the pickup device includes a medicine pack controller such as the medicine pack control unit 70 configured to control a position and a posture of the medicine pack picked up by the pickup device.

With the medication support device according to the fourth mode of the present disclosure, the position or posture of the target one the multiple medicine packs can be controlled while the pickup device is holding one of the multiple medicine packs, and the target one of the multiple medicine packs can be prevented from dropping into a place other than a desired place when the holding operation is released such that the target one of the multiple medicine packs will drop off.

According to the fifth mode of the present disclosure, in the medication support device (200) according to the second mode of the present disclosure, the separator is configured to act on an area around a contact portion between the suction device and the specific one of the multiple medicine packs picked up by the pickup device.

With the medication support device according to the fifth mode of the present disclosure, the separator can be operated effectively.

According to the sixth mode of the present disclosure, in the medication support device according to the fifth mode of the present disclosure, the separator is configured to act on an area above a center of a contact portion between the suction device and the specific one of the multiple medicine packs picked up by the pickup device.

With the medication support device according to the sixth mode of the present disclosure, an area above the center of the suction device is pressed by the separator to address a portion even closer to a problematic site responsible for a failure of dropping the medicine pack. Accordingly, the separating operation can successfully be done.

According to the seventh mode of the present disclosure, in the medication support device according to the third mode of the present disclosure, the separator is configured to operate together with an operation of the suction-device driver.

With the medication support device according to the seventh mode of the present disclosure, the suction-device driver can be shared or used in common, and cost reduction and space saving can be achieved.

According to the eighth mode of the present disclosure, in the medication support device according to any one of the first mode to the seventh mode of the present disclosure, the separator is configured to partially serve as a medicine pack controller such as the separation control unit 71 configured to control a position and a posture of the medicine pack picked up by the pickup device.

With the medication support device according to the eighth mode of the present disclosure, a wide area of the medicine pack can be controlled, and a wide area can be pushed when the separating operation is performed. Accordingly, the degree of reliability to dispense medicines to the medicine dispenser can be increased.

According to the ninth mode of the present disclosure, in the medication support device according to the second or third mode of the present disclosure, the separator is configured to act on the medicine pack before suction holding of one of the multiple medicine packs by the suction device is released.

With the medication support device according to the ninth mode of the present disclosure, the separator is instructed to start the separating operation before the suction holding of one of the multiple medicine packs by the pair of suction unit is released by vacuum breakdown. Accordingly, the changes in posture or attitude such as the changes in the level of inclination due to the imbalanced sticking power of one of the multiple medicine packs to the suction device can be prevented, and the degree of reliability to dispense medicines to the medicine dispenser can be increased.

According to the tenth mode of the present disclosure, the medication support device according to the second or third mode of the present disclosure further includes a sensor such as the pack sensor 75 around the separator, and the sensor is configured to detect whether there is any one of the multiple medicine packs. Moreover, the separator is configured to perform separating operation based on detection information obtained by the sensor after suction holding of one of the multiple medicine packs by the suction device is released.

With the medication support device according to the tenth mode of the present disclosure, the suction holding of one of the multiple medicine packs by the suction unit is released by vacuum breakdown before the separating member acts on a portion, and the sensor detects whether one of the multiple medicine packs is being dropped or stuck. The separating operation is performed when one of the multiple medicine packs is detected, and the separating operation is not performed when none of the multiple medicine packs is detected. Due to such a configuration, the length of time required for the separating operation can be shortened.

According to the eleventh mode of the present disclosure, in the medication support device according to any one of the first mode to tenth ninth mode of the present disclosure, the multiple medicine packs include a plurality of medicine packages such as the multiple medicine packages 2 in each of which a plurality of medicines are packed and bound medicine packages such as the bound packages 2A in which the multiple medicine packages are stacked on top of each other in layers and bound together.

With the medication support device according to the tenth mode of the present disclosure, various types of medicines in various kinds of states can be provided based on the demands from patients who take medicines or medication assistants.

The above-described embodiments are illustrative and do not limit the present disclosure. Thus, numerous additional modifications and variations are possible in light of the above teachings. For example, elements and/or features of different illustrative embodiments may be combined with each other and/or substituted for each other within the scope of the present disclosure. For example, the technical ideas or matters described in the above-described embodiments, examples, or modifications may be appropriately combined.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application-specific integrated circuit (ASIC), digital signal processor (DSP), field-programmable gate array (FPGA), and conventional circuit components arranged to perform the recited functions.

What is claimed is:

1. A medication support device comprising:

a container including an opening and at least one support portion on a bottom face of the container, the container configured to store a plurality of medicine packs stacked on top of each other in a vertical direction, the at least one support portion connected to at least one horizontal surface of the container, the opening defined by the at least one support portion;

a pickup device configured to pick up a specific one of the plurality of medicine packs through the opening on the bottom face of the container;

a conveyor configured to convey the specific one of the plurality of medicine packs picked up by the pickup device;

a medicine dispenser configured to arrange the specific one of the plurality of medicine packs conveyed by the conveyor; and a separator configured to make the specific one of the plurality of medicine packs picked up by the pickup device separate from the pickup device, wherein a width of the opening on the bottom face of the container in a given direction is narrower than a width of the plurality of medicine packs in the given direction, and both ends of the plurality of medicine packs in the given direction are at positions outside both ends of the opening in the given direction when the plurality of medicine packs are stored in the container.

2. The medication support device according to claim 1, wherein the separator is further configured to partially serve as a medicine pack controller configured to control a position and a posture of one of the plurality of medicine packs picked up by the pickup device.

3. The medication support device according to claim 1, wherein the separator is further configured to act on the specific one of the plurality of medicine packs before suction holding of one of the plurality of medicine packs by a suction device is released.

4. The medication support device according to claim 1, further comprising:

a sensor around the separator, the sensor configured to detect a presence of any one of the plurality of medicine packs; and the separator is further configured to perform separating operation based on detection information obtained by the sensor after suction holding of one of the plurality of medicine packs by a suction device is released.

5. The medication support device according to claim 1, wherein the plurality of medicine packs include:

a plurality of medicine packages in each of which a plurality of medicines are packed; and a plurality of bound medicine packages in which the plurality of medicine packages are stacked on top of each other in layers and bound together.

6. The medication support device according to claim 1, wherein the pickup device includes:

a suction device configured to suction one of the plurality of medicine packs in a downward direction through the opening on the bottom face of the container;

a suction-device driver configured to drive the suction device; and a suction-device guide configured to move the suction device.

7. The medication support device according to claim 1, wherein the pickup device comprises:

a medicine pack controller configured to control a position and a posture of the specific one of the plurality of medicine packs picked up by the pickup device.

8. The medication support device according to claim 1, wherein the separator is further configured to act on an area around a contact portion between a suction device and the specific one of the plurality of medicine packs picked up by the pickup device.

9. The medication support device according to claim 8, wherein the separator is further configured to act on an area above a center of the contact portion between the suction device and the specific one of the plurality of medicine packs picked up by the pickup device.

10. The medication support device according to claim 6, wherein the separator is further configured to operate together with an operation of the suction-device driver.

11. A medication support device comprising:

a container configured to store a plurality of medicine packs;

a pickup device configured to pick up a specific one of the plurality of medicine packs from the container, the pickup device including a rotation axis and a guide, the guide including at least one guide groove;

a conveyor configured to convey the specific one of the plurality of medicine packs picked up by the pickup device;

a medicine dispenser configured to arrange the specific one of the plurality of medicine packs conveyed by the conveyor; and a separator configured to make the specific one of the plurality of medicine packs picked up by the pickup device separate from the pickup device, wherein the pickup device is further configured to place the specific one of the plurality of medicine packs in the medicine dispenser with a vertical posture different from that of a horizontal posture of the specific one of the plurality of medicine packs while it was stored in the container by rotating around the rotation axis and moving along the at least one guide groove to the horizontal posture.

12. The medication support device according to claim 11, wherein the separator is further configured to partially serve as a medicine pack controller configured to control a position and the posture of the specific one of the plurality of medicine packs picked up by the pickup device.

13. The medication support device according to claim 11, wherein the separator is further configured to act on the specific one of the plurality of medicine packs before suction holding of one of the plurality of medicine packs by a suction device is released.

14. The medication support device according to claim 11, further comprising:

a sensor around the separator, the sensor configured to detect a presence of any one of the plurality of medicine packs; and the separator is further configured to perform separating operation based on detection information obtained by the sensor after suction holding of one of the plurality of medicine packs by a suction device is released.

15. The medication support device according to claim 11, wherein the plurality of medicine packs include:

a plurality of medicine packages in each of which a plurality of medicines are packed; and a plurality of bound medicine packages in which the plurality of medicine packages are stacked on top of each other in layers and bound together.

16. The medication support device according to claim 11, wherein the pickup device includes:

a suction device configured to suction one of the plurality of medicine packs from the container;

a suction-device driver configured to drive the suction device; and a suction-device guide configured to move the suction device.

17. The medication support device according to claim 11, wherein the pickup device comprises:

a medicine pack controller configured to control a position and the posture of the specific one of the plurality of medicine packs picked up by the pickup device.

18. The medication support device according to claim 11, wherein the separator is further configured to act on an area around a contact portion between a suction device and the specific one of the plurality of medicine packs picked up by the pickup device.

19. The medication support device according to claim 4, wherein the separator is further configured to act on an area above a center of the contact portion between the suction device and the specific one of the plurality of medicine packs picked up by the pickup device.

20. The medication support device according to claim 16, wherein the separator is further configured to operate together with an operation of the suction-device driver.

* * * * *